United States Patent [19]
Johnson, Jr. et al.

[11] Patent Number: 5,739,307
[45] Date of Patent: Apr. 14, 1998

[54] POLYNUCLEOTIDE ENCODING NEURTURIN NEUROTROPHIC FACTOR

[75] Inventors: Eugene M. Johnson, Jr.; Jeffrey D. Milbrandt; Paul T. Kotzbauer; Patricia A. Lampe, all of St. Louis, Mo.

[73] Assignee: Washington University, St. Louis, Mo.

[21] Appl. No.: 519,777

[22] Filed: Aug. 28, 1995

[51] Int. Cl.$^6$ .......................... C12N 15/16; C12N 15/63; C12P 21/00

[52] U.S. Cl. .................. 536/23.51; 435/69.1; 435/320.1; 435/325; 435/348; 435/252.3; 536/24.31

[58] Field of Search .......................... 536/23.1; 530/399; 435/69.1, 320.1, 240.2, 325, 348, 252.3, 24.31, 6

[56] References Cited

U.S. PATENT DOCUMENTS

| | | | |
|---|---|---|---|
| 5,011,914 | 4/1991 | Collins et al. | 530/399 |
| 5,141,856 | 8/1992 | Collins et al. | 435/69.1 |
| 5,235,043 | 8/1993 | Collins et al. | 530/399 |
| 5,260,417 | 11/1993 | Grant et al. | 530/351 |

FOREIGN PATENT DOCUMENTS

WO 93/06116  4/1993  WIPO.
WO 95/06662  3/1995  WIPO.

OTHER PUBLICATIONS

Stratagene Catalog (1994) pp. 154–159.
Trupp et al. (1995), Peripheral Expression and Biological Activities of GDNF, a New Neurotrophic Factor for Avian and Mammalian Peripheral Neurons, *J. Cell. Bio.* 130:137–48.
Kearns et al.(1995), GDNF Protects Nigrao Dopamine Neurons Against 6-Hydroxydopamine in vivo, *Brain Research* 672:104–11.
Bowenkamp et al. (1995), Glial Cell Line–Derived Neurotrophic Factor Supports Survival of Injured Midbrain Dopaminergic Neurons, *J. Comp. Neuro.* 355:479–89.
Buj–Bello et al. (1995), GDNF is an Age-Specfic Survival Factor for Sensory and Autonomic Neurons, *Neuron* 15:821–8.
Levi–Montalcini et al. (1951), Selective Growth Stimulating Effects of Mouse Sarcoma on the Sensory and Sympathetic Nervous System of the Chick Embryo, *J. Exp. Zool.* 116:321–61.
Liebrock et al. (1989), Molecular Cloning and Expression of Brain–Derived Neurotrophic Factor, *Nature* 341:149–52.
Klein (1994), Role of Neurotrophins in Mouse Neuronal Development, *FASEB J* 8:738–44.
Lin et al. (1989), Purification, Cloning, and Expression of Ciliary Neurotrophic Factor (CNTF), *Science* 246: 1023–5.
Cheng et al. (1991), NGF and bFGF Protect Rat Hippocampal and Human Cortical Neurons Against Hypoglycemic Damage by Stabilizing Calcium Homeostasis, *Neuron* 1: 1031–41.
Kotzbauer et al. (1994), Postnatal Development of Survival Responsiveness in at Sympathetic Neurons to Leukemia Inhibitory Factor and Ciliary Neurotrophic Factor, *Neuron* 12: 763:73.
Lin et al. (1993), GDNF : A Glial Cell Line–Derived Neurotrophic Factor for Midbrain Dopaminergic Neurons, *Science* 260:1130–2.
Henderson et al. (1994), GDNF: A Potent Survival Factor for Motoneurons Present in Peripheral Nerve and Muscle, *Science* 266: 1062–4.
Yan et al. (1995), In Vivol Neurotrophic Effects of GDNF on Neonatal and Adult Facial Motor Neurons, *Nature* 373:341–4.
Opponenheim et al. (1995), Developing Motor Neurons Rescued from Programmed and Axotomy–Induced Cell Death by GDNF, *Nature* 373: 344–6.
Kingsley (1994), the TGF–β Superfamily: New Members, New Receptors, and New Genetic Tests of Function in Different Organisms, *Genes and Dev* 8:133–46.
Tuszynski et al. (1994), Neurotrophic Factors and Diseases of the Nervous System, *Ann Neurol* 35:S9–S12.

*Primary Examiner*—Stephen Walsh
*Assistant Examiner*—Michael D. Pak
*Attorney, Agent, or Firm*—Howell & Haferkamp, L.C.

[57] ABSTRACT

A novel growth factor, neurturin, is disclosed. The human and mouse amino acid sequences have been identified. Human and mouse neurturin genomic DNA sequences have been cloned and sequences and the respective cDNA sequences identified. The subcloning into vectors and the preparation of cells stably transformed with the vectors is also disclosed. In addition, methods for treating degenerative conditions using neurturin, methods for detecting gene alterations and methods for detecting and monitoring patient levels of neurturin are provided. Methods for identifying additional members of the neurturin-GDNF family of growth factors are also provided.

37 Claims, 13 Drawing Sheets

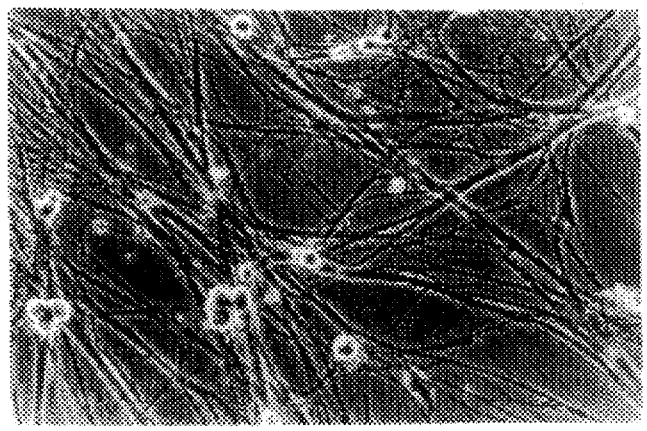
Figure 3a NGF

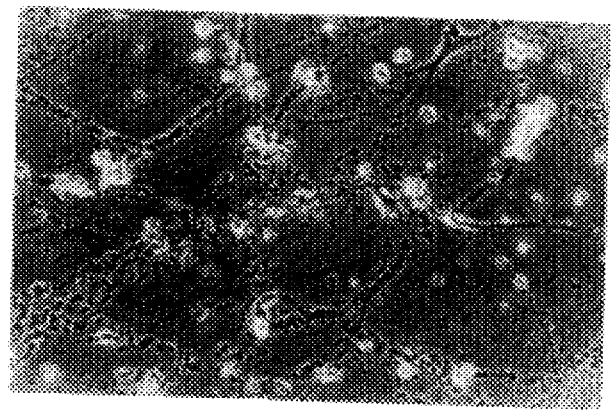
Figure 3b Anti-NGF

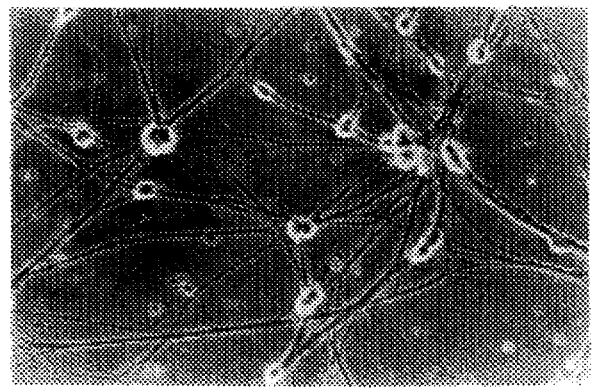
Figure 3c Anti-NGF
+
Neurturin

```
  1   S P D K Q M A V L P R R E R N R Q A A A A N P E N S R G K G   hGDNF
  1   S P D K Q A A A L P R R E R N R Q A A A A S P E N S R G K G   mGDNF
  1   S P D K Q A A A L P R R E R N R Q A A A A S P E N S R G K G   rGDNF
  1   - - - - - - - - - - - - - - - - - - - - - - - - - - - - - -   hNTN
  1   - - - - - - - - - - - - - - - - - - - - - - - - - - - - - -   mNTN

31   R R G Q R G K N R G C V L T A I H L N V T D L G L G Y E T K   hGDNF
 31   R R G Q R G K N R G C V L T A I H L N V T D L G L G Y E T K   mGDNF
 31   R R G Q R G K N R G C V L T A I H L N V T D L G L G Y E T K   rGDNF
  1   - - - A R L G A R P C G L R E L E V R V S E L G L G Y A S D   hNTN
  1   - - - - - - P G A R P C G L R E L E V R V S E L G L G Y T S D   mNTN

61   E E L I F R Y C S G S C D A A E T T Y D K I L K N L S R N R   hGDNF
 61   E E L I F R Y C S G S C E S A E T M Y D K I L K N L S R S R   mGDNF
 61   E E L I F R Y C S G S C E A A E T M Y D K I L K N L S R S R   rGDNF
 28   E T V L F R Y C A G A C E A A A R V Y D L G L R R L R Q R R   hNTN
 26   E T V L F R Y C A G A C E A A I R I Y D L G L R R L R Q R R   mNTN

91   R L V S D K V - G Q A C C R P I A F D D D L S F L D D N L V   hGDNF
 91   R L T S D K V - G Q A C C R P V A F D D D L S F L D D N L V   mGDNF
 91   R L T S D K V - G Q A C C R P V A F D D D L S F L D D N L V   rGDNF
 58   R L R R E R V R A Q P C C R P T A Y E D E V S F L D A H S R   hNTN
 56   R V R R E R A R A H P C C R P T A Y E D E V S F L D V H S R   mNTN

120   Y H I L R K H S A K R C G C I .   hGDNF
120   Y H I L R K H S A K R C G C I .   mGDNF
120   Y H I L R K H S A K R C G C I .   rGDNF
 88   Y H T V H E L S A R E C A C V .   hNTN
 86   Y H T L Q E L S A R E C A C V .   mNTN
```

Figure 5

```
ATGCAGCGCTGGAAGGCGGCGGCCTTGGCCTCAGTGCTCTGCAGCTCCGTGCTGTCCATC  60
Met Gln Arg Trp Lys Ala Ala Ala Leu Ala Ser Val Leu Cys Ser Ser Val Leu Ser Ile

TGGATGTGTCGAGAGGGCCTGCTTCTCAGCCACCGCCTCGGACCTGCGCTGGTCCCCCTG  120
Trp Met Cys Arg Glu Gly Leu Leu Leu Ser His Arg Leu Gly Pro Ala Leu Val Pro Leu

CACCGCCTGCCTCGAACCCTGGACGCCCGGATTGCCCGCCTGGCCCAGTACCGTGCACTC  180
His Arg Leu Pro Arg Thr Leu Asp Ala Arg Ile Ala Arg Leu Ala Gln Tyr Arg Ala Leu

CTGCAGGGGGCCCCGGATGCGATGGAGCTGCGCGAGCTGACGCCCTGGGCTGGGCGGCCC  240
Leu Gln Gly Ala Pro Asp Ala Met Glu Leu Arg Glu Leu Thr Pro Trp Ala Gly Arg Pro

CCAGGTCCGCGCCGTCGGGCGGGGCCCCGGCGGCGGCGCGCGCGTGCGCGGTTGGGGGCG  300
Pro Gly Pro Arg Arg Arg Ala Gly Pro Arg Arg Arg Arg Ala Arg Ala Arg Leu Gly Ala

CGGCCTTGCGGGCTGCGCGAGCTGGAGGTGCGCGTGAGCGAGCTGGGCCTGGGCTACGCG  360
Arg Pro Cys Gly Leu Arg Glu Leu Glu Val Arg Val Ser Glu Leu Gly Leu Gly Tyr Ala

TCCGACGAGACGGTGCTGTTCCGCTACTGCGCAGGCGCCTGCGAGGCTGCCGCGCGCGTC  420
Ser Asp Glu Thr Val Leu Phe Arg Tyr Cys Ala Gly Ala Cys Glu Ala Ala Ala Arg Val

TACGACCTCGGGCTGCGACGACTGCGCCAGCGGCGGCGCCTGCGGCGGGAGCGGGTGCGC  480
Tyr Asp Leu Gly Leu Arg Arg Leu Arg Gln Arg Arg Arg Leu Arg Arg Glu Arg Val Arg

GCGCAGCCCTGCTGCCGCCCGACGGCCTACGAGGACGAGGTGTCCTTCCTGGACGCGCAC  540
Ala Gln Pro Cys Cys Arg Pro Thr Ala Tyr Glu Asp Glu Val Ser Phe Leu Asp Ala His

AGCCGCTACCACACGGTGCACGAGCTGTCGGCGCGCGAGTGCGCCTGCGTGTGA  594
Ser Arg Tyr His Thr Val His Glu Leu Ser Ala Arg Glu Cys Ala Cys Val  *
```

Figure 7

ATGAGGCGCTGGAAGGCAGCGGCCCTGGTGTCGCTCATCTGCAGCTCCCTGCTATCTGTC 60
Met Arg Arg Trp Lys Ala Ala Ala Leu Val Ser Leu Ile Cys Ser Ser Leu Leu Ser Val

TGGATGTGCCAGGAGGGTCTGCTCTTGGGCCACCGCCTGGGACCCGCGCTTGCCCCGCTA 120
Trp Met Cys Gln Glu Gly Leu Leu Leu Gly His Arg Leu Gly Pro Ala Leu Ala Pro Leu

CGACGCCCTCCACGCACCCTGGACGCCCGCATCGCCCGCCTGGCCCAGTATCGCGCTCTG 180
Arg Arg Pro Pro Arg Thr Leu Asp Ala Arg Ile Ala Arg Leu Ala Gln Tyr Arg Ala Leu

CTCCAGGGCGCCCCGACGCGGTGGAGCTTCGAGAACTTTCTCCCTGGGCTGCCCGCATC 240
Leu Gln Gly Ala Pro Asp Ala Val Glu Leu Arg Glu Leu Ser Pro Trp Ala Ala Arg Ile

CCGGGACCGCGCCGTCGAGCGGGTCCCCGGCGTCGGCGGGCGCGGCCGGGGGCTCGGCCT 300
Pro Gly Pro Arg Arg Arg Ala Gly Pro Arg Arg Arg Arg Ala Arg Pro Gly Ala Arg Pro

TGTGGGCTGCGCGAGCTCGAGGTGCGCGTGAGCGAGCTGGGCCTGGGCTACACGTCGGAT 360
Cys Gly Leu Arg Glu Leu Glu Val Arg Val Ser Glu Leu Gly Leu Gly Tyr Thr Ser Asp

GAGACCGTGCTGTTCCGCTACTGCGCAGGCGCGTGCGAGGCGGCCATCCGCATCTACGAC 420
Glu Thr Val Leu Phe Arg Tyr Cys Ala Gly Ala Cys Glu Ala Ala Ile Arg Ile Tyr Asp

CTGGGCCTTCGGCGCCTGCGCCAGCGGAGGCGCGTGCGCAGAGAGCGGGCGCGGGCGCAC 480
Leu Gly Leu Arg Arg Leu Arg Gln Arg Arg Arg Val Arg Arg Glu Arg Ala Arg Ala His

CCGTGTTGTCGCCCGACGGCCTATGAGGACGAGGTGTCCTTCCTGGACGTGCACAGCCGC 540
Pro Cys Cys Arg Pro Thr Ala Tyr Glu Asp Glu Val Ser Phe Leu Asp Val His Ser Arg

TACCACACGCTGCAAGAGCTGTCGGCGCGGGAGTGCGCGTGCGTGTGA 588
Tyr His Thr Leu Gln Glu Leu Ser Ala Arg Glu Cys Ala Cys Val •

Figure 8

```
GGAGGGAGAGCGCGCGGTGGTTTCGTCCGTGTGCCCCGCGCCCGGCGC           -301
TCCTCGCGTGGCCCCGCGTCCTGAGCGCGCTCCAGCCTCCCACGCGCC           -251
ACCCCGGGGTTCACTGAGCCCGGCGAGCCCGGGGAAGACAGAGAAAGAGA         -201
GGCCAGGGGGGGAACCCCATGGCCCGGCCCGTGTCCCGCACCCTGTGCGG         -151
TGGCCTCCTCCGGCACGGGGTCCCCGGGTCGCCTCCGGTCCCCGCGATCC         -101
GGATGGCGCACGCAGTGGCTGGGGCCGGGCCGGGCTCGGGTGGTCGGAGG          -51
AGTCACCACTGACCGGGTCATCTGGAGCCCGTGGCAGGCCGAGGCCCAGG           -1
ATGAGGCGCTGGAAGGCAGCGGCCCTGGTGTCGCTCATCTGCAGCTCCCT           50
GCTATCTGTCTGGATGTGCCAGGAGGGTCTGCTCTTGGGCCACCGCCTGG          100
GACCCGCGCTTGCCCCGCTACGACGCCCTCCACGCACCCTGGACGCCCGC          150
ATCGCCCGCCTGGCCCAGTATCGCGCTCTGCTCCAGGGCGCCCCCGACGC          200
GGTGGAGCTTCGAGAACTTTCTCCCTGGGCTGCCCGCATCCCGGGACCGC          250
GCCGTCGAGCGGGTCCCCGGCGTCGGCGGGCGCGGCCGGGGGCTCGGCCT          300
TGTGGGCTGCGCGAGCTCGAGGTGCGCGTGAGCGAGCTGGGCCTGGGCTA          350
CACGTCGGATGAGACCGTGCTGTTCCGCTACTGCGCAGGCGCGTGCGAGG          400
CGGCCATCCGCATCTACGACCTGGGCCTTCGGCGCCTGCGCCAGCGGAGG          450
CGCGTGCGCAGAGAGCGGGCGCGGGCGCACCCGTGTTGTCGCCCGACGGC          500
CTATGAGGACGAGGTGTCCTTCCTGGACGTGCACAGCCGCTACCACACGC          550
TGCAAGAGCTGTCGGCGCGGGAGTGCGCGTGCGTGTGATGCTACCTCACG          600
CCCCCCGACCTGCGAAAGGGCCCTCCCTGCCGACCCTCGCTGAGAACTGA          650
CTTCACATAAAGTGTGGGAACTCCC                                   675
```

Figure 9

POLYNUCLEOTIDE ENCODING NEURTURIN NEUROTROPHIC FACTOR

REFERENCE TO GOVERNMENT GRANT

This invention was made with government support under Grant Numbers NS24679 and CA53524. The government has certain rights in this invention.

BACKGROUND OF THE INVENTION (1) Field of the Invention

This invention relates generally to trophic or growth factors and, more particularly, to the novel growth factor, neurturin.

(2) Description of the Related Art

The development and maintenance of tissues in complex organisms requires precise control over the processes of cell proliferation, differentiation, survival and function. A major mechanism whereby these processes are controlled is through the actions of polypeptides known as "growth factors". These structurally diverse molecules act through specific cell surface receptors to produce these actions.

In recent years it has become apparent that growth factors fall into classes, i.e. families or superfamilies based upon the similarities in their amino acid sequences. Examples of such families that have been identified include the fibroblast growth factor family, the neurotrophin family and the transforming growth factor-beta (TGF-β) family.

Of particular importance are those growth factors, termed "neurotrophic factors", that promote the differentiation, growth and survival of neurons and reside in the nervous system or in innervated tissues. Nerve growth factor (NGF) was the first neurotrophic factor to be identified and characterized (Levi-Montalcini et al., *J. Exp. Zool.* 116:321, 1951 which is incorporated by reference). NGF exists as a non-covalently bound homodimer. This factor promotes the survival and growth of sympathetic, neural crest-derived sensory, and basal forebrain cholinergic neurons. In sympathetic neurons this substance produces neurite outgrowth in vitro and increased axonal and dendritic growth in vivo. Early indications as to the physiological roles of NGF were obtained from in vivo studies involving the administration of neutralizing antibodies (Levi-Montalcini and Booker, *Proc Nat'l Acad Sci* 46:384–391, 1960; Johnson et al. *Science* 210:916–918, 1980 which are incorporated by reference), and these studies have been confirmed by analyzing transgenic mice lacking NGF via gene targeting (Crowley et al., *Cell* 76:1001–12, 1994 which is incorporated by reference). NGF has effects on cognition and neuronal plasticity, and can promote the survival of neurons that have suffered damage due to a variety of mechanical, chemical, viral, and immunological insults (Snider and Johnson, *Ann Neurol* 26:489–506, 1989; Hefti, *J Neurobiol* 25:1418–35, 1994 which are incorporated by reference). NGF also is known to extensively interact with the endocrine system and in immune and inflammatory processes. (Reviewed in Scully and Otten, *Cell Biol Int* 19:459–469, 1995; Otten and Gadient, Int. *J. Devl Neurosci* 13:147–151, 1995 which are incorporated by reference). For example, NGF promotes the survival of mast cells. (Horigome et al. *J Biol. Chem* 269:2695–2707, 1994 which is incorporated by reference).

It became apparent that NGF was the prototype of a family of neurotrophic factors upon the discovery and cloning of brain-derived neurotrophic factor (BDNF) (Liebrock et al. *Nature* 341:149–152, 1989 which is incorporated by reference), which was the second member of this family to be discovered. The relationship of BDNF to NGF, is evidenced in the conservation of all six cysteines that form the three internal disulfides of the NGF monomer (Barde, *Prog Growth Factor Res* 2:237–248, 1990 which is incorporated by reference). By utilizing the information provided by BDNF of the highly conserved portions of two factors, additional members (NT-3, NT-4/5) of this neurotrophin family were rapidly found by several groups (Klein, *FASEB J* 8:738–44, 1994 which is incorporated by reference). Information concerning their distribution and activities, and the physiologic consequences of their deficiencies (via gene targeting), has greatly increased our knowledge of neuronal development (for reviews, see Jelsma et al., *Curr Opin Neurobiol* 4:717–25, 1995; Lindsay et al., *Trends Neurosci* 17:182–90, 1994; and Johnson et al., *Curr Biol* 4:662–5, 1994 which are incorporated by reference). For instance, it is now clear that the various neurotrophins act on largely non-overlapping neuronal populations (e.g. motor neurons, sub-populations of sensory neurons), and regulate their survival and metabolism in ways similar to those originally described for NGF. Their identification has also led to refinements in the neurotrophic hypothesis, as evidence has accumulated that neurons can switch their neurotrophin survival requirements during maturation (for review, see Davies, *Curr Biol* 4:273–6, 1994 which is incorporated by reference).

Recently, the understanding of the mechanisms of signal transduction for neurotrophic factors has been advanced by the identification of receptors for the NGF family of neurotrophic factors. The tyrosine kinase receptor, trkA, identified as the NGF receptor and the closely related receptors trkB, which mediates signaling of BDNF and NT-4/5, and trkC, which mediates effects of NT-3, have allowed dissection of the signal transduction pathways utilized by these neurotrophins (for review, see (Tuszynski et al., *Ann Neurol* 35:S9–S12, 1994 which is incorporated by reference). Signaling by NGF involves proteins which interact directly with the phosphorylated trkA receptor (e.g. Shc, PLCγ1, PI-3 kinase), other trkA substrates like SNT (Rabin et al., *Mol Cell Biol* 13:2203–13, 1995 which is incorporated by reference), and downstream kinase effectors (e.g. ras, raf1, MEK and MAP kinase). In some cases, particular components have been linked to specific actions of NGF, such as Shc and PLCγ1 requirement for neurite outgrowth (Loeb et al., *J Biol Chem* 269:8901–10, 1994; Stephens et al., *Neuron* 12:691–705, 1994 which is incorporated by reference) and PI-3 kinase requirement for survival (Yao and Cooper, *Science* 267:2003–6, 1995 which is incorporated by reference).

In addition to the discovery of molecules related to NGF, structurally unrelated neurotrophic factors have also been recently identified. These include factors originally isolated based upon a "neurotrophic action" such as ciliary neurotrophic factor (CNTF) (Lin et al., *Science* 246:1023–5, 1989 which is incorporated by reference) along with others originally isolated as a result of non-neuronal activities (e.g. fibroblast growth factors (Cheng and Mattson *Neuron* 1:1031–41,1991 which is incorporated by reference), IGF-I (Kanje et al, *Brain Res* 486:396–398, 1989 which is incorporated by reference) leukemia inhibitory factor (Kotzbauer et al, *Neuron* 12:763–773, 1994 which is incorporated by reference).

Glial-derived neurotrophic factor (GDNF), is one such neurotrophic factor structurally unrelated to NGF. GDNF was, thus, a unique factor, which, up until now, was not known to be a member of any subfamily of factors. The discovery, purification and cloning of GDNF resulted from a search for factors crucial to the survival of midbrain dopaminergic neurons, which degenerate in Parkinson's disease. GDNF was purified from rat B49 glial cell conditioned media (Lin et al., *Science* 260:1130–2, 1993 which is incorporated by reference). Sequence analysis revealed it to be a distant member of the superfamily of transforming growth factor β (TGF-β) factors, having approximately 20% identity based primarily on the characteristic alignment of the 7 cysteine residues (Lin et al., *Science* 260:1130–2, 1993 which is incorporated by reference). Thus, GDNF could possibly have represented a new subfamily within the TGF-β superfamily.

GDNF, like other members of the TGF-β superfamily, has a precursor molecule, with a signal sequence and variably sized pro-region, that is generally cleaved at an RXXR site to release the 134 amino acid mature protein, GDNF. Thus, GDNF is synthesized as a precursor protein.

Subsequent processing results in a mature glycosylated homodimer of approximately 35–40 kD. Six of the seven cysteines form intrachain disulfide bonds and connect hydrogen-bonded β-sheets to make a rigid structure called a cystine knot (McDonald et al., *Cell* 73:421–4, 1993 which is incorporated by reference), a structure which, interestingly, is also characteristic of the neurotrophins. The remaining cysteine forms a disulfide bond with another monomer to form the biologically active hetero- and homodimers. This structure may account for the strong resistance of GDNF to denaturants such as sodium dodecyl sulfate (SDS), heat and pH extremes.

Recombinant GDNF produced in bacteria specifically promotes the survival and morphological differentiation of dopaminergic neurons in midbrain neuronal cultures (Lin et al., *Science* 260:1130–2, 1993 which is incorporated by reference). These initial in vitro experiments have now been extended to in vivo models which demonstrate that GDNF has potent protective and regenerative effects on MPTP- or axotomy-induced lesions of dopaminergic neurons in adult rodent brain (Tomac et al., *Nature* 373:335–9, 1995 and Beck et al., *Nature* 373:339–41, 1995 which is incorporated by reference). GDNF promotes the survival in vitro of nodose sensory and parasympathetic neurons, and can rescue chicken sympathetic neurons from NGF deprivation-induced death, but this requires much higher doses than are necessary for its effects on dopaminergic neurons (Ebendal et al., *J Neurosci Res* 40:276–84, 1995 which is incorporated by reference). Significantly, GDNF is retrogradely transported by motor neurons and is known to promote the survival of motor neurons inasmuch as animals treated with GDNF suffer much less motor neuron loss in response to lesions than untreated animals or those treated with other trophic factors such as CNTF, BDNF, NT-3 or NT-4/5 (Henderson et al., *Science* 266:1062–4, 1994; Yan et al., *Nature* 373:341–4, 1995; and Oppenheim et al., *Nature* 373:344–6, 1995 which are incorporated by reference). Overall, GDNF was a more potent factor for promoting the survival of motor neurons than the other factors, and it was the only factor that prevented neuronal atrophy in response to these lesions, thereby positioning it as a promising therapeutic agent for motor neuron diseases.

Neuronal degeneration and death occur during development, during senescence, and as a consequence of pathological events throughout life. It is now generally believed that neurotrophic factors regulate many aspects of neuronal function, including survival and development in fetal life, and structural integrity and plasticity in adulthood. Since both acute nervous system injuries as well as chronic neurodegenerative diseases are characterized by structural damage and, possibly, by disease-induced apoptosis, it is likely that neurotrophic factors play some role in these afflictions. Indeed, a considerable body of evidence suggests that neurotrophic factors may be valuable therapeutic agents for treatment of these neurodegenerative conditions, which are perhaps the most socially and economically destructive diseases now afflicting our society. Nevertheless, because different neurotrophic factors can act preferentially through different receptors and on different neuronal cell types, there remains a continuing need for the identification of new members of neurotrophic factor families for use in the diagnosis and treatment of a variety of acute and chronic diseases of the nervous system.

SUMMARY OF THE INVENTION

Briefly, therefore, the present invention is directed to the identification and isolation of substantially purified factors that promote the survival and growth of neurons. Accordingly, the inventors herein have succeeded in discovering a novel protein growth factor referenced herein as neurturin. This growth factor is believed to show at least 85% sequence identity among homologous sequences from different mammalian species although sequence homology may be as low as 65% in non-mammalian species such as avian species. Neurturin proteins identified herein include the human sequence as set forth in SEQ ID NO:1 (FIG. 5; FIG. 7, amino acid residues 96 through 197) and the mouse sequence as set forth in SEQ ID NO:2 (FIG. 5; FIG. 8, amino acid residues 96 through 195).

Neurturin has been identified and obtained from conditioned medium of the Chinese hamster ovary cells, DG44CHO-pHSP-NGFI-B cells, hereinafter referenced as CHO cells and the factor as isolated from these cells has an apparent molecular weight of approximately 20–30 kD as determined by sodium dodecyl sulfate-polyacrylamide gel electrophoresis (SDS-PAGE) under non-reducing conditions and an $EC_{50}$ in a superior cervical ganglion survival assay of less than about 10 ng/ml. The protein isolated from Chinese hamster ovary cells is believed to be a homodimeric protein whose monomers have an apparent molecular weight of approximately 10–15 kD.

Neurturin, can also be identified on the basis of fragments obtained following partial digestion of the factor isolated from CHO cell conditioned medium wherein some of the amino acid residues were not at the time known with certainty. Such fragments include an N-terminal fragment, Ser-Gly-Ala-Arg-Pro-Xaa-Gly-Leu-Arg-Glu-Leu-Glu-Val-Ser-Val-Ser where Xaa was an unknown amino acid (SEQ ID NO:3) and internal amino acid fragments, $Xaa_1$-Cys-Ala-Gly-Ala-$Xaa_2$-Glu-Ala-Ala-Val where $Xaa_1$ was unknown amino acid, $Xaa_2$ was Ser or Cys (SEQ ID NO:4), $Xaa_1$-$Xaa_2$-Val-Glu-Ala-Lys-Pro-Cys-Cys-Gly-Pro-Thr-Ala-Tyr-Glu-Asp-$Xaa_3$-Val-Ser-Phe-Leu-Ser-Val where $Xaa_1$ and $Xaa_2$ were unknown, $Xaa_3$ was Gln or Glu (SEQ ID NO:5) and Tyr-His-Thr-Leu-Gln-Glu-Leu-Ser-Ala-Arg (SEQ ID NO:6).

A pre-pro form of neurturin is cleaved to form the mature protein and the human pre-pro form containing the pre-pro region and the mature neurturin sequence for human is as set forth in SEQ ID NO:7 (FIG. 7, amino acid residues 1 through 197). The mouse pre-pro form is as set forth in SEQ ID NO:8 (FIG. 8, amino acid residues 1 through 195).

The present invention also provides nucleotide sequences that encode the human neurturin as set forth in the amino acid sequence of SEQ ID NO:1 and the mouse neurturin as set forth in the amino acid sequence of SEQ ID NO:2. The human sequence is further identified as being encoded by the nucleotide sequence of SEQ ID NO:9 (FIG. 7, nucleic acid 286 through nucleic acid 591) and the mouse sequence is further identified as being encoded by the nucleotide sequence of SEQ ID NO:10 (FIG. 8, nucleic acid 286 through nucleic acid 585). Also provided are the nucleotide sequences that encode the human pre-pro neurturin as set forth in the amino acid sequence of SEQ ID NO:7 and the mouse pre-pro neurturin as set forth in the amino acid sequence of SEQ ID NO:8. The human pre-pro neurturin sequence is further identified as being encoded by the nucleotide sequence of SEQ ID NO:11 (FIG. 7, nucleic acid 1 through nucleic acid 591) and the mouse pre-pro neurturin sequence is further identified as being encoded by the nucleotide sequence of SEQ ID NO:12 (FIG. 8, nucleic acid 1 through nucleic acid 585).

Expression vectors and stably transformed cells are also provided. The transformed cells can be used in a method for producing neurturin.

In another embodiment, the present invention provides a method for preventing or treating neuronal degeneration comprising administering to a patient in need thereof a therapeutically effective amount of neurturin. A patient may also be treated by implanting transformed cells which express neurturin or a DNA sequence which encodes neurturin into a patient, or cells cultured and expanded by growth in neurturin.

The present invention also provides compositions and methods for detecting neurturin. One method is based upon neurturin antibodies and other methods are based upon detecting neurturin mRNA using recombinant DNA techniques.

Among the several advantages found to be achieved by the present invention, therefore, may be noted the provision of a new growth factor, neurturin, which can maintain and prevent the atrophy, degeneration or death of certain cells, in particular neurons; the provision of other members of the neurturin-GDNF family of growth factors by making available new methods capable of obtaining said other family members; the provision of methods for obtaining neurturin by recombinant techniques and by isolation from cells; the provision of methods for preventing or treating diseases producing cellular degeneration and, particularly neuronal degeneration; the provision of methods that can detect and monitor neurturin levels in a patient; and the provision of methods that can detect alterations in the neurturin gene.

BRIEF DESCRIPTION OF THE DRAWINGS

FIG. 3 illustrates the ability of neurturin to maintain survival of superior cervical ganglionic cells in culture showing (a) positive control cells maintained with nerve growth factor (NGF) (b) negative control cells treated with anti-NGF antibodies showing diminished survival and (c) cells treated with anti-NGF and neurturin (approximately 3 ng/ml) showing survival of neurons;

FIG. 5 illustrates the homology of the amino acid sequences for the mature growth factors, human neurturin (hNTN SEQ ID NO:1), mouse neurturin (mNTN SEQ ID NO:2), rat GDNF (rGDNF SEQ ID NO:78), mouse GDNF (mGDNF SEQ ID NO:77) and human GDNF (hGDNF SEQ ID NO:76) with identical amino acid residues enclosed in boxes;

FIG. 7 illustrates the cDNA and encoded amino acid sequence of human pre-pro neurturin (SEQ ID NO:11) showing the pre- region from nucleic acid 1 through 57 (SEQ ID NO:17), the pro- region from nucleic acid 58 through 285 (SEQ ID NO:20), human neurturin from nucleic acid 286 through 591 (SEQ ID NO:9) and the splice-site between nucleic acids 169 and 170 which defines the coding sequence portion of two exons from nucleic acids 1 through 169 (SEQ ID NO:27) and 170 through 594 (SEQ ID NO:28);

FIG. 8 illustrates the cDNA and encoded amino acid sequence of mouse pre-pro neurturin (SEQ ID NO:12) showing the pre- region from nucleic acid 1 through 57 (SEQ ID NO:18), the pro- region from nucleic acid 58 through 285 (SEQ ID NO:21), mouse neurturin from nucleic acid 286 through 585 (SEQ ID NO:10) and the splice site between nucleic acids 169 and 170 which defines the coding sequence portion of two exons from nucleic acids 1 through 169 (SEQ ID NO:29) and 170 through 588 (SEQ ID NO:30);

FIG. 9 illustrates the mouse cDNA sequence containing a 5' non-coding region (SEQ ID NO:13) and a 3' non-coding region (SEQ ID NO:14) each of which are contiguous to the coding region of pre-pro neurturin.

DESCRIPTION OF THE PREFERRED EMBODIMENTS

Figure 1:
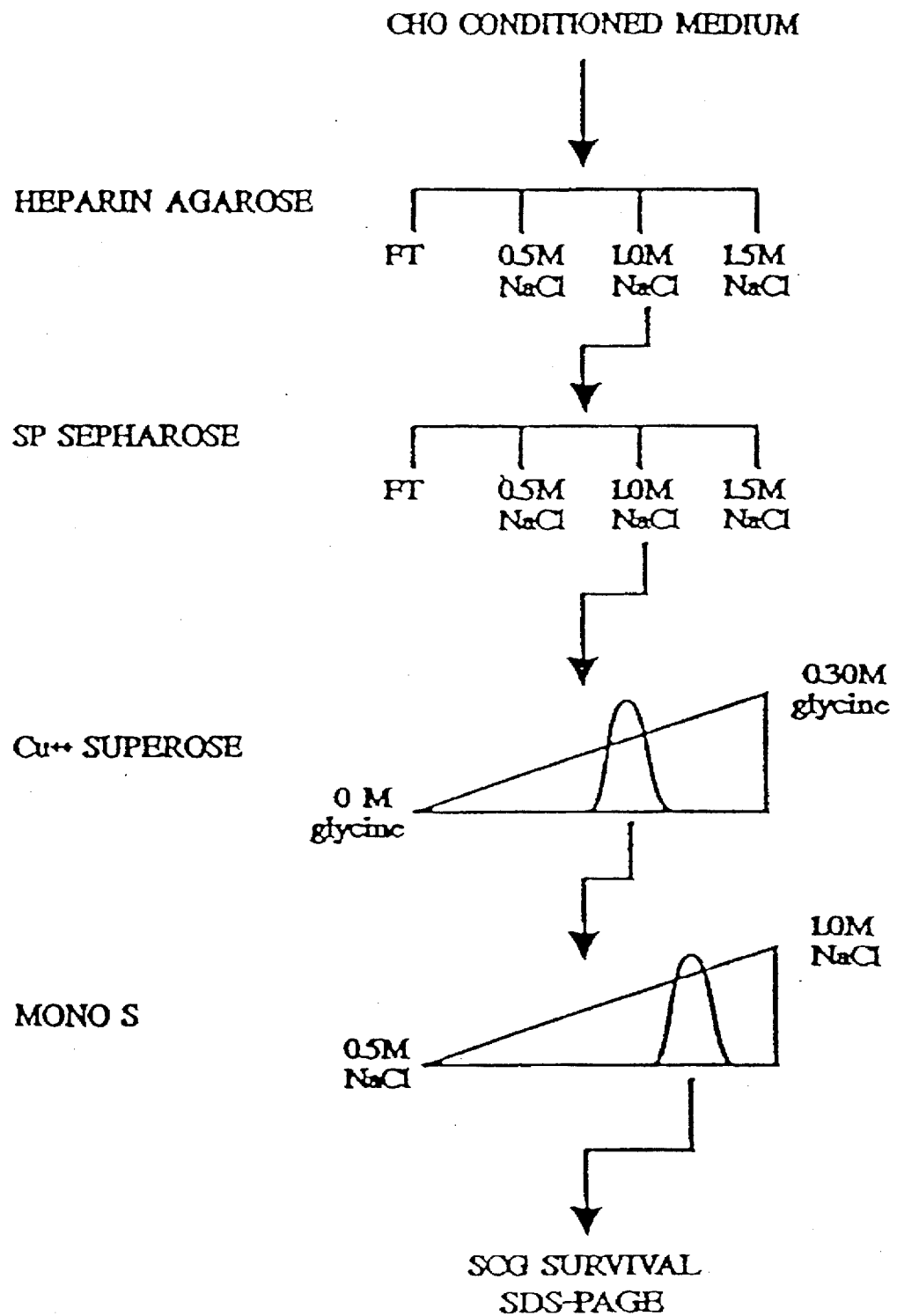
FIG. 1 illustrates the purification scheme for preparing neurturin from CHO cells.

The present invention is based upon the identification, isolation and sequencing of a new growth factor, neurturin. Surprisingly, this substance has been discovered to be able to promote cell survival and, in particular, the survival of neurons. Prior to this invention, neurturin was unknown and had not been identified as a discrete biologically active substance nor had it been isolated in pure form.

The inventors herein have succeeded in discovering and isolating neurturin from conditioned medium for CHO cells. The initial neuronal survival promoting activity was identified by the inventors in a partially purified preparation of this CHO-conditioned medium. Preparation of conditioned medium for a given cell line is well known in the art (for example, see Reid, in *Methods in Enzymology* Vol. LVIII, *Cell Culture*, Jakoby and Pastan, Eds., Academic Press, San Diego, pp 161–164, 1979; Freshney, Culture of Animal Cells in *A Manual of Basic Technique*, 2d Ed., Wiley-Liss, NY, p. 84, 1987 which are incorporated by reference). Thus, although in the present work CHO cells were cultured and the conditioned medium used to identify and to obtain neurturin in purified form, one skilled in the art will readily appreciate that any cell that expresses neurturin can be used as a source. Some of the cells that express neurturin are identified below in Example 9 and the inventors herein believe that any of the cells identified as expressing neurturin can be used to obtain conditioned medium from which neurturin can be isolated.

In the isolation of neurturin from the CHO cell conditioned medium, an initial crude conditioned medium can be obtained by centrifugation and/or filtration to remove cellular debris. For further purification, one skilled in the art will readily appreciate that any of a number of methods known in the art can be used to isolate and purify neurturin from a biological sample such as affinity chromatography, ion exchange chromatography, preparative electrophoresis or the like wherein the methods are used either individually or in combination.

The cell survival promoting effect of neurturin can be assessed in any suitable system for assessing cell survival. The inventors herein believe that neurturin can promote survival in a variety of different tissues based upon what is known for other growth factors and upon the observation that neurturin is expressed in a number of tissues in which it is believed to have a survival promoting effect. In the work reported herein, neuronal activity was assessed using a sympathetic neuronal survival assay (sympathetic cervical ganglia, SCG) which has been extensively characterized (Martin et al, *J Cell Biol* 106:829–844, 1989; Deckwerth and Johnson, *J Cell Biol* 123:1207–1222, 1993 which are incorporated by reference) (see FIG. 3). We also show the survival promoting effects of neurturin on sensory neurons (See FIG. 10).

The SCG assay involved, in brief, the culturing of cells obtained from superior cervical ganglia of rat embryo for 5 days at 37° C. in medium containing nerve growth factor (NGF). The medium was then exchanged with a medium containing no NGF and containing anti-NGF antiserum. Removal of NGF results normally in death of the neurons in 24–72 hours. Neuronal survival was visually assessed under a microscope on days 7–8. Maximum neuronal survival criteria included lack of degeneration of both neuronal cell bodies and neurites. Cell body degeneration was indicated when the neuronal cell body was reduced in size, showed irregular membrane swellings, contained vacuoles, or had lost refractility. A field of neurites was scored as showing signs of disintegration when swellings and blebs appeared along the neurite bundles. Survival was determined by comparison with neurons grown in the presence of NGF (positive control) or in the absence of NGF with NGF antisera (negative control).

Activity was quantitated by calculation of a "survival unit". The total survival units in a sample were defined as the minimal volume of an aliquot of the sample which produced maximal survival divided into the total volume of that sample. For example, a volume of 600 ml was eluted from the heparin agarose column and from this eluate, 12.5 µl was the minimum volume that promoted maximal volume. Thus, the survival units in the eluate from the heparin agarose column was 48,000. Specific activity was calculated as the survival units divided by the mg total protein. The intrinsic activity of neurturin is expressed herein in concentration units of pg/ml or pM promoting maximal or half-maximal survival. As shown in FIG. 5, a concentration-response curve of purified neurturin protein indicates that the intrinsic activity of neurturin expressed as an $EC_{50}$ is approximately 1.5 ng/ml or approximately 50 pM and an $EC_{100}$ is approximately 3 ng/ml or approximately 100 pM.

Figure 4:
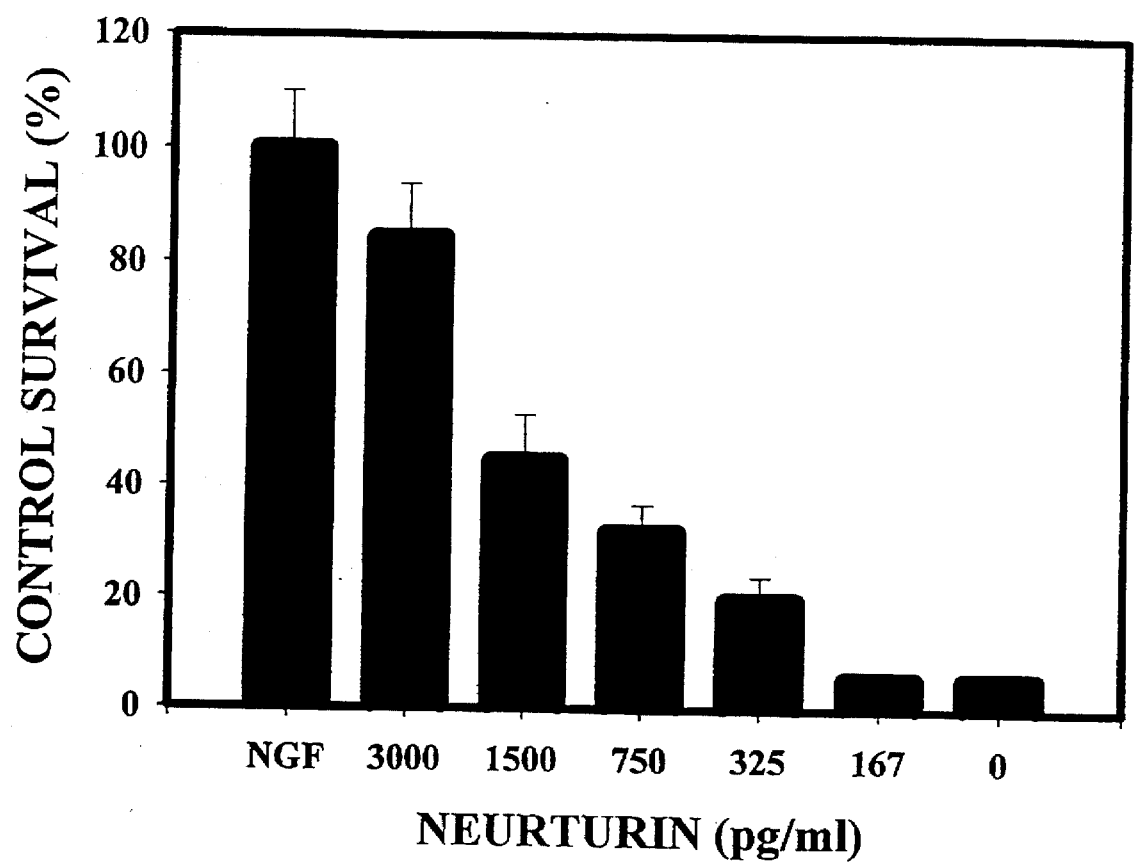
FIG. 4 illustrates the concentration-response effect of neurturin in the superior cervical ganglion survival assay.

Survival units were determined in an assay using approximately 1200 neurons in a 0.5 ml culture assay and a culture period of 48 hours following addition of the fraction. Survival was assessed visually after the 48 hours. Intrinsic activity as shown in FIG. 4 was determined in an assay using approximately 2700 neurons and a culture period of 72 hours. Survival was assessed by fixing the neurons and counting the number of surviving neurons. Because the stability, as assessed by half-life of activity, for neurturin decreases as the number of neurons increases, the intrinsic activity measurement would be expected to be lower than that predicted by Specific Activity determinations. The intrinsic activity measurement would also be expected to be lower than that predicted by specific activity because the survival was measured after 72 hours instead of 48 hours.

The purification of neurturin is described in detail in Example 1 below. The conditioned medium starting material was prepared from a derivative of DG44 Chinese hamster ovary cells, DG44CHO-pHSP-NGFI-B (Day et al, *J Biol Chem* 265:15253–15260, 1990 which is incorporated by reference). The inventors herein have also isolated neurturin in partially purified form from conditioned medium of other derivatives of DG44 Chinese hamster ovary cells and these other cells could be used equally as well as the DG44CHO-pHSP-NGFI-B cells as could the parent DG44 Chinese hamster ovary Cells, ovary cells from other species and cells from other tissues such as those known to express neurturin (See example 9). In preparing the conditioned medium, cells were placed in serum free medium for 2 days at which time conditioned medium is collected and the medium replenished. This cycle was repeated to yield 5 harvests of conditioned medium from each batch of CHO cells. The collected media was centrifuged to remove cellular debris.

The first step in purification of neurturin from the CHO cell conditioned medium involved the introduction of the conditioned medium onto a heparin agarose column and the elution of partially purified neurturin therefrom. This step resulted in an 111 fold increase in the specific activity and purification of the protein. The buffer used to apply the medium to the column contains 0.5M NaCl. At this concentration of NaCl the neurturin binds to the heparin agarose matrix. The inventors herein believe that based upon their isoelectric points, LIF and CNTF would either not bind to the heparin agarose matrix or be washed away from the matrix with buffer containing 0.5M NaCl. Thus, this step would be expected to isolate neurturin from growth factors such as LIF and CNTF. After washing the column, neurturin was eluted from the column using 1.0M NaCl.

For further purification, the eluted material was then diluted and introduced into a column containing SP SEPHAROSE® High Performance ion exchange resin (Pharmacia, Piscataway, N.J.). Material eluted from this column was further purified using fast protein liquid chromatography (FPLC) on a Chelating Superose HR 10/2 column charged with $Cu^{++}$ (Pharmacia, Piscataway, N.J.). Eluted fractions from the $Cu^{++}$ superose column were introduced into a Mono S HR 5/5 cation exchange column (Pharmacia, Piscataway, N.J.) for further FPLC purification. The composition of the proteins in the Mono S fractions were analyzed using non-reducing SDS-PAGE and silver staining.

Fractions collected from the columns at each stage of purification were assayed for biological activity using the neuronal survival assay and for protein content using the dye binding method of Bradford (*Anal Biochem* 72:248–254, 1976 which is incorporated by reference) with a Bio-Rad protein assay dye reagent (Bio-Rad Laboratories, Inc., Hercules, Calif.). The progressive purification using the above steps is shown in table 1.

TABLE 1

|  | Protein[a] (mg) | Activity[b] (units) | Specific Activity[d] (units/mg) | Yield (%) | Purification (fold) |
|---|---|---|---|---|---|
| Conditioned Medium | 5000 | 48000[c] | 9.6 | — | — |
| Heparin Agarose | 45 | 48000 | 1068 | 100 | 111 |
| SP Sepharose | 5.3 | 48000 | 9058 | 100 | 943 |
| Cu++ Superose | 0.31 | 30000 | 96700 | 62 | 10070 |
| Mono S | 0.004 | 15000 | 3750000 | 31 | 390000 |

[a]mg protein was determined using the dye binding method of Bradford (Anal Biochem 72:248, 1976).
[b]The total activity units or survival units in a sample were defined as the minimal volume of an aliquot of the sample which produced maximal survival divided into the total volume of that sample.
[c]Activity for Conditioned Medium was derived from the assumption that 100% of the activity was recovered in the heparin agarose fraction because the activity of conditioned medium was too low to be directly assayed.
[d]Specific Activity was the Activity units divided by the mg total protein.

The results of this analysis along with the results of the neuronal survival assay of fractions revealed that a protein having an apparent molecular weight of about 25 kD co-purified with the sympathetic neuron survival activity.

The purified material isolated from CHO cell conditioned medium was used to determine partial amino acid sequences of the protein in CHO cell conditioned medium and subsequently as a basis for determining the sequences in different species. The N-terminal amino acid sequence was determined using an automated protein/peptide sequencer and the first 16 amino acids were considered to be, with uncertainty as to position 6, Ser-Gly-Ala-Arg-Pro-Xaa-Gly-Leu-Arg-Glu-Leu-Glu-Val-Ser-Val-Ser where Xaa was an unknown amino acid (SEQ ID NO:3). Internal amino acid fragments were obtained from the purified material following digestion with protease enzymes and the sequences determined. Three internal fragments thus obtained were (1) with uncertainty as to positions 1, 2 and 6, $Xaa_1$-Cys-Ala-Gly-Ala-$Xaa_2$-Glu-Ala-Ala-Val where $Xaa_1$ was unknown amino acid, $Xaa_2$ was Ser or Cys (SEQ ID NO:4); (2) with uncertainty as to positions 1, 2, 4, 10, 17 and 22, $Xaa_1$-$Xaa_2$-Val-Glu-Ala-Lys-Pro-Cys-Cys-Gly-Pro-Thr-Ala-Tyr-Glu-Asp-$Xaa_3$-Val-Ser-Phe-Leu-Ser-Val where $Xaa_1$ and $Xaa_2$ were unknown, $Xaa_3$ was Gln or Glu (SEQ ID NO:5) and (3) Tyr-His-Thr-Leu-Gln-Glu-Leu-Ser-Ala-Arg (SEQ ID NO:6). Based upon these partial amino acid sequences, DNA probes and primers can be made and used to obtain cDNA clones from different species based upon high sequence conservation between mammalian species. The human cDNA and inferred amino acid sequence is shown in FIG. 7 and the mouse cDNA and inferred amino acid sequence is shown in FIG. 8.

The cDNA clone from mouse was 1.0 kb having an open reading frame of 585 nucleotides (SEQ ID NO:12) encoding the mouse pre-pro neurturin protein (SEQ ID NO:8, FIG. 8). In addition, non-coding regions have been identified at both the 5' and 3' ends of the coding region as shown in FIG. 9. (SEQ ID NO:13, 5' non-coding region, nucleic acids −348 through −1; SEQ ID NO:14, 3' non-coding region, nucleic acids 589 through 675). The mouse neurturin sequence can be used to obtain PCR primers for use in identifying homologs from other species. A human 192 nucleotide fragment from human genomic DNA was amplified by this method and further used to screen a human genomic library to obtain clones containing the human neurturin genomic locus. The human cDNA sequence was deduced from the sequencing of these clones. (FIG. 7, cDNA sequence of human pre-pro neurturin).

Reference to neurturin herein is intended to be construed to include growth factors of any origin which are substantially homologous to and which are biologically equivalent to the neurturin characterized and described herein. Such substantially homologous growth factors may be native to any tissue or species and, similarly, biological activity can be characterized in any of a number of biological assay systems. Reference to pre-pro neurturin herein is intended to be construed to include pre-pro growth factors containing a pre- or leader or signal sequence region, a pro- sequence region and neurturin as defined herein.

The terms "biologically equivalent" are intended to mean that the compositions of the present invention are capable of demonstrating some or all of the same growth properties in a similar fashion, not necessarily to the same degree as the neurturin isolated from the CHO cell conditioned medium herein or recombinantly produced human or mouse neurturin.

By "substantially homologous" it is meant that the degree of homology of human and mouse neurturin to neurturin from any species is greater than that between neurturin and any previously reported member of the TGF-β superfamily or GDNF (For discussion of homology of TGF-β superfamily members see Kingsley, *Genes and Dev* 8:133–46, 1994 which is incorporated by reference).

Sequence identity or percent identity is intended to mean the percentage of same residues between two sequences, referenced to human neurturin when determining percent identity with non-human neurturin, referenced to neurturin when determining percent identity with non-neurturin growth factors and referenced to human GDNF when determining percent identity of non-neurturin growth factors with GDNF, when the two sequences are aligned using the Clustlal method (Higgins et al, *Cabios* 8:189–191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment= 10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of Protein Sequence and Structure*, Dayhoff, Ed., NBRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human neurturin when determining percent conservation with non-human neurturin, referenced to neurturin when determining percent conservation with non-neurturin growth factors, and referenced to human GDNF when determining percent conservation to non-neurturin growth factors with GDNF. Conservative amino acid changes satisfying this requirement are: R-K; E-D, Y-F, L-M; V-I, Q-H. The calculations of identity (I) and conservation (C) between mature human and mature mouse neurturin (hNTN and mNTN, respectively) and between each of these and mature human, rat and mouse GDNF (hGDNF, rGDNF and mGDNF, respectively) are shown in table 2.

TABLE 2

| COMPARISON | % IDENTITY | % CONSERVATION |
|---|---|---|
| hNTN v. mNTN | 90 | 93 |
| hNTN v. rGDNF | 44 | 53 |
| hNTN v. mGDNF | 43 | 52 |
| hNTN v. hGDNF | 43 | 53 |
| mNTN v. rGDNF | 42 | 52 |
| mNTN v. mGDNF | 41 | 51 |
| mNTN v. hGDNF | 41 | 52 |

The degree of homology between the mature mouse and human neurturin proteins is about 90% sequence identity and all neurturin homologs of non-human mammalian species are believed to similarly have at least about 85% sequence identity with human neurturin. For non-mammalian species such as avian species, it is believed that the degree of homology with neurturin is at least about 65% identity. By way of comparison, the variations between family members of the neurturin-GDNF family of growth factors can be seen by comparing neurturin and GDNF. Human and mouse neurturin have about 40% sequence identity and about 50% sequence conservation with human, mouse and rat GDNF. It is believed that the different family members similarly have a sequence identity of about 40% of that of neurturin and about 40% of that of GDNF and within a range of about 30% to about 85% identity with neurturin and within a range of about 30% to about 85% sequence identity with GDNF. Thus, a given non-neurturin and non-GDNF family member from one species would be expected to show lesser sequence identity with neurturin and with GDNF from the same species than the sequence identity between human neurturin and neurturin from a non-human mammalian species, but greater sequence identity than that between human neurturin and any other known member of the TGF-β superfamily member except GDNF (Kingsley, supra). In the case of pre-pro neurturin, homologs of pre-pro neurturin in non-human mammalian species can be identified by virtue of the neurturin portion of the amino acid sequence having at least about 85% sequence identity with human neurturin and homologs of pre-pro neurturin in non-mammalian species can be identified by virtue of the neurturin portion of the amino acid sequence having at least about 65% identity with human neurturin.

Neurturin can also include hybrid and modified forms of neurturin including fusion proteins and neurturin fragments and hybrid and modified forms in which certain amino acids have been deleted or replaced and modifications such as where one or more amino acids have been changed to a modified amino acid or unusual amino acid and modifications such as glycosolations so long as the hybrid or modified form retains the biological activity of neurturin. By retaining the biological activity, it is meant that neuronal survival is promoted, although not necessarily at the same level of potency as that of the neurturin isolated from CHO cell conditioned medium or that of the recombinantly produced human or mouse neurturin.

Also included within the meaning of substantially homologous is any neurturin which may be isolated by virtue of cross-reactivity with antibodies to the neurturin described herein or whose encoding nucleotide sequences including genomic DNA, mRNA or cDNA may be isolated through hybridization with the complementary sequence of genomic or subgenomic nucleotide sequences or cDNA of the neurturin herein or fragments thereof. It will also be appreciated by one skilled in the art that degenerate DNA sequences can encode human neurturin and these are also intended to be included within the present invention as are allelic variants of neurturin.

In the case of pre-pro neurturin, alternatively spliced protein products resulting from an intron located in the coding sequence of the pro region may exist. The intron is believed to exist in the genomic sequence at a position corresponding to that between nucleic acids 169 and 170 of the cDNA which, in turn, corresponds to a position within amino acid 57 in both the mouse and human pre-pro neurturin sequences (see FIGS. 7 and 8). Thus, alternative splicing at this position might produce a sequence that differs from that identified herein for human and mouse pre-pro neurturin (SEQ ID NO:11 and SEQ ID NO:12, respectively) at the identified amino acid site by addition and/or deletion of one or more amino acids. Any and all alternatively spliced pre-pro neurturin proteins are intended to be included within the terms pre-pro neurturin as used herein.

Although it is not intended that the inventors herein be bound by any theory, it is thought that the human and mouse proteins identified herein as well as homologOs from other tissues and species may exist as dimers in their biologically active form in a manner consistent with what is known for other factors of the TGF-β superfamily.

In addition to homodimers, the monomeric units of the dimers of neurturin can be used to construct stable growth factor heterodimers or heteromultimers comprising at least one monomer unit derived from neurturin. This can be done by dissociating a homodimer of neurturin into its component monomeric units and reassociating in the presence of a monomeric unit of a second homodimeric growth factor. This second homodimeric growth factor can be selected from a variety of growth factors including GDNF or a member of the NGF family such as NGF, BDNF, NT-3 and NT-4/5 or a member of the TGF-β superfamily, or a vascular endothelial growth factor or a member of the CNTF/LIF family or the like.

Growth factors are thought to act at specific receptors. For example, the receptors for TGF-β and activins have been identified and make up a family of Ser/Thr kinase transmembrane proteins (Kingsley, Genes and Dev 8:133–146, 1994; Bexk et al Nature 373:339–341, 1995 which are incorporated by reference). In the NGF family, NGF binds to the TrkA receptor in peripheral sensory and sympathetic neurons and in basal forebrain neurons; BDNF and NT-4/5 bind to trkB receptors; and NT-3 binds primarily to trkC receptors that possess a distinct distribution within the CNS (Tuszynski et al., Ann Neurol 35:S9–S12, 1994). The inventors herein believe that GDNF, neurturin and as yet unknown members of this family of growth factors act through specific receptors having distinct distributions as has been shown for other growth factor families. Thus, by forming heterodimers or heteromultimers of neurturin and one or more other growth factors, the resultant growth factor would be expected to be able to bind to at least two distinct receptor types preferentially having a different tissue distribution. The resultant heterodimers or heteromultimers would be expected to show an enlarged spectrum of cells upon which it could act or provide greater potency. It is also possible that the heterodimer or heteromultimer might provide synergistic effects not seen with homodimers or homomultimers. For example, the combination of factors from different classes has been shown to promote long-term survival of oligodendrocytes whereas single factors or combinations of factors within the same class promoted short-term survival (Barres et al., *Development* 118:283–295, 1993).

Heterodimers can be formed by a number of methods. For example, homodimers can be mixed and subjected to conditions in which dissociation/unfolding occurs, such as in the presence of a dissociation/unfolding agent, followed by subjection to conditions which allow monomer reassociation and formation of heterodimers. Dissociation/unfolding agents include any agent known to promote the dissociation of proteins. Such agents include, but are not limited to, guanidine hydrochloride, urea, potassium thiocyanate, pH lowering agents such as buffered HCl solutions, and polar, water miscible organic solvents such as acetonitrile or alcohols such as propanol or isopropanol. In addition, for homodimers linked covalently by disulfide bonds as is the case with TGF-β family members, reducing agents such as dithiothreitol and β-mercaptoethanol can be used for dissociation/unfolding and for reassociation/refolding.

Heterodimers can also be made by transfecting a cell with two or more factors such that the transformed cell produces heterodimers as has been done with neurotrophin. (Heymach and Schooter, *J Biol Chem* 270:12297–12304, 1995).

Another method of forming heterodimers is by combining neurturin homodimers and a homodimer from a second growth factor and incubating the mixture at 37° C.

When heterodimers are produced from homodimers, the heterodimers may then be separated from homodimers using methods available to those skilled in the art such as, for example, by elution from preparative, non-denaturing polyacrylamide gels. Alternatively, heterodimers may be purified using high pressure cation exchange chromatography such as with a Mono S cation exchange column or by sequential immunoaffinity columns.

It is well known in the art that many proteins are synthesized within a cell with a signal sequence at the N-terminus of the mature protein sequence and the protein carrying such a leader sequence is referred to as a preprotein. The preportion of the protein is cleaved during cellular processing of the protein. In addition to a pre- leader sequence, many proteins contain a distinct pro sequence that describes a region on a protein that is a stable precursor of the mature protein. Proteins synthesized with both pre- and pro- regions are referred to as preproproteins. In view of the processing events known to occur with other TGF-β family members as well as the sequences determined herein, the inventors believe that the form of neurturin protein as synthesized within a cell is the pre-pro neurturin. The pre-pro neurturin is believed to contain an N-terminal 19 amino acid signal sequence (human pre- signal sequence, SEQ ID NO:15, FIG. 7, amino acids 1 through 19 encoded by SEQ ID NO:17, FIG. 7, nucleic acids 1 through 57; mouse pre- signal sequence, SEQ ID NO:16, FIG. 8, amino acids 1 through 19, encoded by SEQ ID NO:18, FIG. 8, nucleic acids 1 through 57). It is known that the full length of a leader sequence is not necessarily required for the sequence to act as a signal sequence and, therefore, within the definition of pre- region of neurturin is included fragments thereof, usually N-terminal fragments, that retain the property of being able to act as a signal sequence, that is to facilitate co-translational insertion into the membranes of one or more cellular organelles such as endoplasmic reticulum, mitochondria, golgi, plasma membrane and the like.

The signal sequence is followed by a pro-domain which contains an RXXR proteolytic processing site immediately before the N-terminal amino acid sequence for the mature neurturin. (human pro- region sequence, SEQ ID NO:19, FIG. 7, amino acids 20 through 95 encoded by the nucleic acid sequence SEQ ID NO:20, FIG. 7 nucleic acids 58 through 285; mouse pro- region sequence, SEQ ID NO:22, FIG. 8, amino acids 19 through 95 encoded by nucleic acid sequence SEQ ID NO:21, FIG. 8, nucleic acids 58 through 285).

The pre- and pro- regions together comprise a pre-pro sequence identified as the human pre-pro sequence (SEQ ID NO:23, FIG. 7, amino acids 1 through 95 encoded by SEQ ID NO:25, nucleic acids 1 through 285) and the mouse pre-pro sequence (SEQ ID NO:24, FIG. 8, amino acids 1 through 95 encoded by SEQ ID NO:26, nucleic acids 1 through 285). The pre- region sequences and pro-region sequences as well as the pre-pro region sequences can be identified and obtained for non-human mammalian species and for non-mammalian species by virtue of the sequences being contained within the pre-pro neurturin as defined herein.

Using the above landmarks, the mature, secreted neurturin molecule is predicted to be approximately 11.5 kD which is likely to form a disulfide linked homodimer of approximately 23 kD by analogy to other members of the TGF-β family. The predicted approximately 23 kD protein is consistent with the 25 kD protein purified from CHO cell conditioned media being a homodimer. The inventors herein have detected an approximately 11.5 kD protein from conditioned medium of Chinese hamster ovary cells transfected with the neurturin expression vector (pCMV-NTN-3-1) using SDS-PAGE under reducing conditions and this protein is thought to be the monomer.

The nucleotide sequences of pre- and/or pro- regions can also be used to construct chimeric genes with the coding sequences of other growth factors or proteins and, similarly, chimeric genes can be constructed from the coding sequence of neurturin coupled to sequences encoding pre- and/or pro-regions from genes for other growth factors or proteins. (Booth et al., *Gene* 146:303–8, 1994; Ibanez, *Gene* 146:303–8, 1994; Storici et al., *FEBS Letters* 337:303–7, 1994; Sha et al *J Cell Biol* 114:827–839, 1991 which are incorporated by reference). Such chimeric proteins can exhibit altered production or expression of the active protein species.

A preferred neurturin of the present invention has been identified and isolated in purified form from medium conditioned by CHO cells. Also preferred is neurturin prepared by recombinant DNA technology. By "pure form" or "purified form" or "substantially purified form" it is meant that a neurturin composition is substantially free of other proteins which are not neurturin.

Recombinant human neurturin may be made by expressing the DNA sequences encoding neurturin in a suitable transformed host cell. Using methods well known in the art, the DNA encoding neurturin may be linked to an expression vector, transformed into a host cell and conditions established that are suitable for expression of neurturin by the transformed cell.

Any suitable expression vector may be employed to produce recombinant human neurturin such as, for example, the mammalian expression vector pCB6 (Brewer, *Meth Cell Biol* 43:233–245, 1994) or the *E. coli* pET expression vectors, specifically, pET-30a (Studier et al., *Methods Enzymol* 185:60–89, 1990 which is incorporated by reference)

both of which were used herein. Other suitable expression vectors for expression in mammalian and bacterial cells are known in the art as are expression vectors for use in yeast or insect cells. Baculovirus expression systems can also be employed.

Neurturin may be expressed in the monomeric units or such monomeric form may be produced by preparation under reducing conditions. In such instances refolding and renaturation can be accomplished using one of the agents noted above that is known to promote dissociation/ association of proteins. For example, the monomeric form can be incubated with dithiothreitol followed by incubation with oxidized glutathione disodium salt followed by incubation with a buffer containing a refolding agent such as urea.

By analogy with the N-terminal sequence and internal fragments of the neurturin purified from CHO cell conditioned medium, the mature mouse sequence was deduced and from this the mature human form was predicted using the sequence from the human gene. The amino acid sequence of the mature human form is as shown in FIG. 5 (hNTN, SEQ ID NO:1). The material purified from CHO cell conditioned medium is considered to be mature neurturin and may exist as a dimer or other multimer and may be glycosylated or chemically modified in other ways. As noted above, the mouse and human nucleic acid sequences suggest that neurturin is initially translated as a pre-pro polypeptide and that proteolytic processing of the signal sequence and the "pro" portion of this molecule results in the mature sequence, referenced herein as "mature neurturin", as obtained from medium condition by CHO cells and as exists in human and in non-human species in homologous form. The present invention, therefore, includes any and all "mature neurturin" sequences from human and non-human species and any and all pre-pro neurturin polypeptides that may be translated from the neurturin gene.

It is believed that the coding sequence for the pre-pro-neurturin polypeptide begins at the first ATG codon encoding methionine at the 5' end of the clone (position 1 in FIG. 9) which is positioned in the same reading frame as the sequence encoding the amino acid sequences obtained from the purified neurturin. Downstream from the first codon is the largest open reading frame containing the coding sequence for the pre- and pro-regions followed by the coding sequence for the mature mouse neurturin.

Sequence analysis of the murine neurturin genomic clones identified a 0.5 kb intron located between nucleotide 169 and 170 of the pre-pro neurturin from the cDNA clones. This intron is located in the coding sequence of the pro- region of the pre-pro-neurturin protein. Thus, it is believed that the mouse nuerturin gene contains at least two exons, one of which contains the coding sequences upstream from the splice site and the other contains the coding sequence downstream (FIG. 8, SEQ ID NO:29, SEQ ID NO:30). It is known that the gene for GDNF contains an intron located at an analogous position and an alternately spliced form of GDNF has been detected by RT-PCR experiments (Suter-Crazzolara and Unsicker, *Neuroreport* 5:2486-2488, 1994 which is incorporated by reference). This alternate form results from the use of a splice site in the second coding exon located 78 bp 3' to the original splice site reported. The alternately spliced form encodes a GDNF protein with a deletion of 26 amino acids relative to the originally reported form. The two forms are expressed in different ratios in different tissues. We have not detected alternately spliced forms of neurturin in RT-PCR and RACE experiments using mouse P1 brain and P1 liver cDNAs. The possibility exists, however, that alternate splice sites in the neurturin gene may be utilized in different tissues.

The coding sequence of the human neurturin cDNA has been deduced from the sequence of the human neurturin genomic clones. The coding sequence of the human cDNA, like that of the mouse cDNA, is interrupted by an intron between nucleotides 169 and 170 of the coding sequence. Thus, the human neurturin gene is believed to contain at least two exons, one of which contains the coding sequence upstream from the splice site and the other contains the coding sequence downstream (FIG. 7, SEQ ID NO:27, SEQ ID NO:28). The splice sites at the intron-exon junctions of the human and mouse genes have been conserved.

From the deduced amino acid sequence of human neurturin, the earlier predicted N-terminal sequence lies between positions 286 and 339 and the predicted internal sequences lie between positions 385 and 417, positions 474 and 533, and positions 547 and 576. The TGA stop codon at positions 592-594 terminate the open reading frame.

The predicted length of the purified pre-pro neurturin is 197 amino acid residues for the human pre-pro neurturin (SEQ ID NO:7) and 195 amino acid residues for the mouse pre-pro neurturin (SEQ ID NO:8). The predicted molecular weight of this polypeptide is 22.2 kD for mouse and 22.4 kd for human. The predicted length of the purified neurturin is 100 amino acid residues and its predicted monomeric molecular weight is 11.5 kD. There are no N-linked glycosolation sites, however, potential O-linked glycosolation sites occur at amino acid residues in positions 18, 26, 80, 86 and 95 in human neurturin. Glycosylation at any one or combination of these sites would increase the molecular weight of the molecule.

Different possible cleavage sites may be present in the pre-pro-neurturin sequence. The amino acid sequence of the mature mouse neurturin (FIG. 5, SEQ ID NO:2) is predicted from alignment with the N-terminal amino acid sequence of the purified chinese hamster neurturin. A four residue RRAR cleavage site (amino acids 92-95) is found immediately before the predicted N-terminal amino acid of mature mouse neurturin. This RRAR sequence fits the RXXR consensus sequence at which members of the TGF-β superfamily are usually cleaved. This putative RRAR cleavage sequence is conserved in human neurturin. However, the mature human neurturin is predicted to have a two amino acid N-terminal extension relative to mature mouse neurturin when cleaved at this sequence. Since neurturin contains other sequences which fit the RXXR consensus (for example the sequence RRRR at amino acids 90-93) and the specificities of proteases involved in this cleavage are not completely understood, the possibility exists that in some situations, neurturin is cleaved at sites other than the above RRAR sequence, and the mature neurturin protein may have a variable number of amino acids preceding the cysteine residue at position 101 in the mouse sequence (pre-pro protein) and position 103 in the human sequence. Such alternate cleavage sites could be utilized differently among different organisms and among different tissues of the same organism. The N-terminal amino acids preceding the first of the seven conserved cysteines in the mature forms of members of the TGF-β family vary greatly in both length and sequence. Furthermore, insertion of a ten amino acid sequence two residues upstream of the first conserved cysteine does not affect the known biological activities of one family member, dorsalin (Basler, K., Edlund, T., Jessell, T. M., and Yamada, T., (1993) Cell 73:687-702). Thus neurturin proteins which contain sequences of different lengths preceding the cysteine 101 in mouse and cysteine 103 in human would be likely to retain their biological activity.

The inventors herein believe that at a minimum the sequence of neurturin that will show biological activity will contain the sequence beginning at cysteine 103 and ending at cysteine 196 for human neurturin (FIG. 7, SEQ ID NO:31) and beginning at cysteine 101 and ending at cysteine 194 for mouse neurturin (FIG. 7, SEQ ID NO:32). Thus, within the scope of the present invention are amino acid sequences containing SEQ ID NO:31 and amino acid sequences containing SEQ ID NO:32 and nucleic acid sequences encoding these amino acid sequences.

The present invention includes nucleic acid sequences including sequences that encode human and mouse neurturin (FIG. 5). Also included within the scope of this invention are sequences that are substantially the same as the nucleic acid sequences encoding neurturin. Such substantially the same sequences may, for example, be substituted with codons more readily expressed in a given host cell such as *E. coli* according to well known and standard procedures. Such modified nucleic acid sequences would be included within the scope of this invention.

Specific nucleic acid sequences can be modified by those skilled in the art and, thus, all nucleic acid sequences which encode for the amino acid sequences of pre-pro neurturin or the pre- region or the pro- region or neurturin can likewise be so modified. The present invention thus also includes nucleic acid sequence which will hybridize with all such nucleic acid sequences—or complements of the nucleic acid sequences where appropriate—and encode for a polypeptide having cell survival promoting activity. The present invention also includes nucleic acid sequences which encode for polypeptides that have neuronal survival promoting activity and that are recognized by antibodies that bind to neurturin.

The present invention also encompasses vectors comprising expression regulatory elements operably linked to any of the nucleic acid sequences included within the scope of the invention. This invention also includes host cells—of any variety—that have been transformed with vectors comprising expression regulatory elements operably linked to any of the nucleic acid sequences included within the scope of the present invention.

Methods are also provided herein for producing neurturin. Preparation can be by isolation from conditioned medium from a variety of cell types so long as the cell type produces neurturin. A second and preferred method involves utilization of recombinant methods by isolating a nucleic acid sequence encoding neurturin, cloning the sequence along with appropriate regulatory sequences into suitable vectors and cell types, and expressing the sequence to produce neurturin.

A mammalian gene family comprised of four neurotrophic factors has been identified including nerve growth factor (NGF), brain derived neurotrophic factor (BDGF), neurotrophin-3 (NT-3), and neurotrophin-4/5 (NT-4/5). These factors share approximately 60 percent nucleic acid sequence homology (Tuszynski and Gage, *Ann Neurol* 35:S9-S12, 1994 which is incorporated by reference). The neurturin protein displays no significant homology to the NGF family of neurotrophic factors. Neurturin shares less than about 20% homology with the TGF-β superfamily of growth factors. However, neurturin shows approximately 40% sequence identity with GDNF. In particular, the positions of the seven cysteine residues present in both neurturin and GDNF are exactly conserved. The inventors herein believe that other unidentified genes may exist that encode proteins that have substantial amino acid sequence homology to neurturin and GDNF and which function as growth factors selective for the same or different tissues and the same or different biological activities. A different spectrum of activity with respect to tissues affected and/or response elicited could result from preferential activation of different receptors by different family members as is known to occur with members of the NGF family of neurotrophic factors (Tuszynski and Gage, 1994, supra).

As a consequence of members of a particular gene family showing substantial conservation of amino acid sequence among the protein products of the family members, there is considerable conservation of sequences at the DNA level. This forms the basis for a new approach for identifying other members of the gene family to which GDNF and neurturin belong. The method used for such identification is cross-hybridization using nucleic acid probes derived from one family member to form a stable hybrid duplex molecule with nucleic acid sequence from different members of the gene family or to amplify nucleic acid sequences from different family members. (see for example, Kaisho et al. *FEBS Letters* 266:187-191, 1990 which is incorporated by reference). The sequence from the different family member may not be identical to the probe, but will, nevertheless be sufficiently related to the probe sequence to hybridize with the probe. Alternatively, PCR using primers from one family member can be used to identify additional family members.

The above approaches have not heretofore been successful in identifying other gene family members because only one family member, GDNF was known. With the identification of neurturin herein, however, unique new probes and primers can be made that contain sequences from the conserved regions of this gene family. In particular, three conserved regions have been identified herein which can be used as a basis for constructing new probes and primers. The new probes and primers made available from the present work make possible this powerful new approach which can now successfully identify other gene family members. Using this new approach, one may screen for genes related to GDNF and neurturin in sequence homology by preparing DNA or RNA probes based upon the conserved regions in the GDNF and neurturin molecules. Therefore, one embodiment of the present invention comprises probes and primers that are unique to or derived from a nucleotide sequence encoding such conserved regions and a method for identifying further members of the GDNF-neurturin gene family. Conserved region amino acid sequences include Val-Xaa$_1$-Xaa$_2$-Leu-Gly-Leu-Gly-Tyr in which Xaa$_1$ is Ser or Thr and Xaa$_2$ is Glu or Asp (SEQ ID NO:33); Glu-Xaa$_1$-Xaa$_2$-Xaa$_3$-Phe-Arg-Tyr-Cys-Xaa$_4$-Gly-Xaa$_5$-Cys-Xaa$_6$-Xaa$_7$-Ala in which Xaa$_1$ is Thr or Glu, Xaa$_2$ is Val or Leu, Xaa$_3$ is Leu or Ile, Xaa$_4$ is Ala or Ser, Xaa$_5$ is Ala or Ser, Xaa$_6$ is Glu or Asp and Xaa$_7$ is Ala or Ser (SEQ ID NO:34); and Cys-Cys-Arg-Pro-Xaa$_1$-Ala-Xaa$_2$-Xaa$_3$-Asp-Xaa$_4$-Xaa$_5$-Ser-Phe-Leu-Asp in which Xaa$_1$ is Thr or Val or Ile, Xaa$_5$ is Tyr or Phe, Xaa$_3$ is Glu or Asp, Xaa$_4$ is Glu or Asp and Xaa$_5$ is Val or Leu (SEQ ID NO:35). Nucleotide sequences containing a coding sequence for the above conserved sequences or fragments of the above conserved sequences can be used as probes. Exemplary probe and primer sequences include nucleic acid sequences encoding amino acid sequences, SEQ ID NO:33, SEQ ID NO:36, SEQ ID NO:37, SEQ ID NO:38, SEQ ID NO 39, SEQ ID NO:40 and SEQ ID NO:41 and, in particular, nucleic acid sequences, SEQ ID NOS:42, SEQ ID NOS:43, SEQ ID NOS:44, SEQ ID NOS:45, SEQ ID NOS:46, SEQ ID NOS:47, and SEQ ID NOS:48.

Hybridization using the new probes from conserved regions of the nucleic acid sequences would be performed under reduced stringency conditions. Factors involved in determining stringency conditions are well known in the art (for example, see Sambrook et al., *Molecular Cloning*, 2nd Ed., 1989 which is incorporated by reference). Sources of nucleic acid for screening would include genomic DNA libraries from mammalian species or cDNA libraries constructed using RNA obtained from mammalian cells cloned into any suitable vector.

PCR primers would be utilized under PCR conditions of reduced annealing temperature which would allow amplification of sequences from gene family members other than GDNF and neurturin. Sources of nucleic acid for screening would include genomic DNA libraries from mammalian species cloned into any suitable vector, cDNA transcribed from RNA obtained from mammalian cells, and genomic DNA from mammalian species.

DNA sequences identified on the basis of hybridization or PCR assays would be sequenced and compared to GDNF and neurturin. The DNA sequences encoding the entire sequence of the novel factor would then be obtained in the same manner as described herein. Genomic DNA or libraries of genomic clones can also be used as templates because the intron/exon structures of GDNF and neurturin are conserved and coding sequences of the mature proteins are not interrupted by introns.

Although neurturin has been purified on the basis of its ability to promote the survival of a particular neuronal type, this factor will act on other neuronal cell types as well. For example, neurturin is shown herein to promote the survival of nodose sensory ganglia neurons (see Example 3). Neurturin is also likely to promote the survival of non-neuronal cells. Indeed, all the growth factors isolated to date have been shown to act on many different cell types (for example see, Scully and Otten, *Cell Biol Int* 19:459–469, 1005; Hefti, *Neurotrophic Factor Therapy* 25:1418–1435, 1994 which are incorporated by reference). It is known that NGF acts on sympathetic neurons, several types of sensory neurons and certain populations of CNS neurons. GDNF, which is more closely related to neurturin, has been shown to act on dopaminergic, sympathetic, motor and several sensory neurons (Henderson et al. supra, 1994; Miles et al, *J Cell Biol* 130:137–148, 1995; Yan et al, *Nature* 373:341–344, 1995; Lin et al, *Science* 260:1130–1132, 1993; Trupp et al, *J Cell Biol* 130:137–148, 1995; Martin et al *Brain Res* 683:172–178, 1995; Bowenkamp st al *J Comp Neurol* 355:479–489, 1995 which are incorporated by reference). Thus, it is likely that in addition to peripheral sympathetic and sensory neurons, neurturin can act on a wide variety of central and peripheral neuronal cell types.

It is also likely that neurturin will act on non-neuronal cells to promote their survival, growth or function. This expectation is based upon the activity of known growth factors. Although NGF is the prototypical neurotrophic factor, this growth factor also acts upon mast cells to increase the number of mast cells when injected into newborn rats (Aloe, *J Neuroimmunol* 18:1–12, 1988). In addition, mast cells express the trk receptor and respond to NGF such that NGF is a mast cell secretogogue and survival promoting factor (Horigome et al., *J Biol Chem* 269:2695–2707, 1994 which is incorporated by reference). Moreover, members of the TGF-β superfamily act on many cell types of different function and embryologic origin.

The inventors herein have identified several non-neuronal tissues in which neurturin is expressed including blood, bone marrow, neonatal liver and mast cells. This suggests a role for neurturin in hematopoiesis, inflammation and allergy.

Neurotrophic factors of the NGF family are thought to act through factor-specific high affinity receptors (Tuszynski and Gage, 1994, supra). Only particular portions of the protein acting at a receptor site are required for binding to the receptor. Such particular portions or discrete fragments can serve as an agonist where the substance activates the receptor to elicit the promoting action on cell survival and growth and antagonists to neurturin where they bind to, but do not activate, the receptor or promote survival and growth. Such portions or fragments that are agonists and those that are antagonists are also within the scope of the present invention.

Synthetic, pan-growth factors can also be constructed by combining the active domains of neurturin with the active domains of one or more other growth factors. (For example, see Ilag et al., *Proc Nat'l Acad Sci* 92:607–611, 1995 which is incorporated by reference). These pan-growth factors would be expected to have the combined activities of neurturin and the one or more other growth factors. As such they are believed to be potent and multispecific growth factors that are useful in the treatment of a wide spectrum of degenerative diseases and conditions including conditions that can be treated by any and all of the parent factors from which the active domains were obtained. Such pan-growth factors might also provide synergistic effects beyond the activities of the parent factors (Barres et al., supra).

The present invention also includes therapeutic or pharmaceutical compositions comprising neurturin in an effective amount for treating patients with cellular degeneration and a method comprising administering a therapeutically effective amount of neurturin. These compositions and methods are useful for treating a number of degenerative diseases. Where the cellular degeneration involves neuronal degeneration, the diseases include, but are not limited to peripheral neuropathy, amyotrophic lateral sclerosis, Alzheimer's disease, Parkinson's disease, Huntington's disease, ischemic stroke, acute brain injury, acute spinal chord injury, nervous system tumors, multiple sclerosis, peripheral nerve trauma or injury, exposure to neurotoxins, metabolic diseases such as diabetes or renal dysfunctions and damage caused by infectious agents. Where the cellular degeneration involves bone marrow cell degeneration, the diseases include, but are not limited to disorders of insufficient blood cells such as, for example, leukopenias including eosinopenia and/or basopenia, lymphopenia, monocytopenia, neutropenia, anemias, thrombocytopenia as well as an insufficiency of stem cells for any of the above. The above cells and tissues can also be treated for depressed function.

The compositions and methods herein can also be useful to prevent degeneration and/or promote survival in other non-neuronal tissues as well. One skilled in the art can readily determine using a variety of assays known in the art for identifying whether neurturin would be useful in promoting survival or functioning in a particular cell type.

In certain circumstances, it may be desirable to modulate or decrease the amount of neurturin expressed. Thus, in another aspect of the present invention, neurturin anti-sense oligonucleotides can be made and a method utilized for diminishing the level of expression of neurturin by a cell comprising administering one or more neurturin anti-sense oligonucleotides. By neurturin anti-sense oligonucleotides reference is made to oligonucleotides that have a nucleotide sequence that interacts through base pairing with a specific complementary nucleic acid sequence involved in the expression of neurturin such that the expression of neurturin is reduced. Preferably, the specific nucleic acid sequence involved in the expression of neurturin is a genomic DNA molecule or mRNA molecule that encodes neurturin. This genomic DNA molecule can comprise regulatory regions of the neurturin gene, the pre- or pro- portions of the neurturin gene or the coding sequence for mature neurturin protein. The term complementary to a nucleotide sequence in the context of neurturin antisense oligonucleotides and methods therefor means sufficiently complementary to such a sequence as to allow hybridization to that sequence in a cell, i.e., under physiological conditions. The neurturin antisense oligonucleotides preferably comprise a sequence containing from about 8 to about 100 nucleotides and more preferably the neurturin antisense oligonucleotides comprise from about 15 to about 30 nucleotides. The neurturin antisense oligonucleotides can also contain a variety of modifications that confer resistance to nucleolytic degradation such as, for example, modified internucleoside linkages (Uhlmann and Peyman, *Chemical Reviews* 90:543–548, 1990; Schneider and Banner, *Tetrahedron Lett* 31:335, 1990 which are incorporated by reference), modified nucleic acid bases and/or sugars and the like.

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation. For treating tissues in the central nervous system, administration can be by injection or infusion into the cerebrospinal fluid (CSF). When it is intended that neurturin be administered to cells in the central nervous system, administration can be with one or more agents capable of promoting penetration of neurturin across the blood-brain barrier.

Neurturin can also be linked or conjugated with agents that provide desirable pharmaceutical or pharmacodynamic properties. For example, neurturin can be coupled to any substance known in the art to promote penetration or transport across the blood-brain barrier such as an antibody to the transferrin receptor, and administered by intravenous injection. (See for example, Friden et al., *Science* 259:373–377, 1993 which is incorporated by reference). Furthermore, neurturin can be stably linked to a polymer such as polyethylene glycol to obtain desirable properties of solubility, stability, half-life and other pharmaceutically advantageous properties. (See for example Davis et al. *Enzyme Eng* 4:169–73, 1978; Burnham, *Am J Hosp Pharm* 51:210–218, 1994 which are incorporated by reference).

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Neurturin can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing neurturin are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, neurturin may be therapeutically administered by implanting into patients vectors or cells capable of producing a biologically-active form of neurturin or a precursor of neurturin, i.e. a molecule that can be readily converted to a biological-active form of neurturin by the body. In one approach cells that secrete neurturin may be encapsulated into semipermeable membranes for implantation into a patient. The cells can be cells that normally express neurturin or a precursor thereof or the cells can be transformed to express neurturin or a precursor thereof. It is preferred that the cell be of human origin and that the neurturin be human neurturin when the patient is human. However, the formulations and methods herein can be used for veterinary as well as human applications and the term "patient" as used herein is intended to include human and veterinary patients.

Cells can be grown ex vivo for use in transplantation or engraftment into patients (Muench et al., *Leuk & Lymph*

16:1-11, 1994 which is incorporated by reference). In another embodiment of the present invention, neurturin is used to promote the ex vivo expansion of a cells for transplantation or engraftment. Current methods have used bioreactor culture systems containing factors such as erythropoietin, colony stimulating factors, stem cell factor, and interleukins to expand hematopoietic progenitor cells for erythrocytes, monocytes, neutrophils, and lymphocytes (Verfaillie, *Stem Cells* 12:466–476, 1994 which is incorporated by reference). These stem cells can be isolated from the marrow of human donors, from human peripheral blood, or from umbilical cord blood cells. The expanded blood cells are used to treat patients who lack these cells as a result of specific disease conditions or as a result of high dose chemotherapy for treatment of malignancy (George, *Stem Cells* 12 (Suppl 1):249–255, 1994 which is incorporated by reference). In the case of cell transplant after chemotherapy, autologous transplants can be performed by removing bone marrow cells before chemotherapy, expanding the cells ex vivo using methods that also function to purge malignant cells, and transplanting the expanded cells back into the patient following chemotherapy (for review see Rummel and Van Zant, *J Hematotherapy* 3:213–218, 1994 which is incorporated by reference). Since neurturin is expressed in the developing animal in blood, bone marrow and liver, tissues where proliferation and differentiation of progenitor cells occur, it is believed that neurturin can function to regulate the proliferation of hematopoietic stem cells and the differentiation of mature hematopoietic cells. Thus, the addition of neurturin to culture systems used for ex vivo expansion of cells could stimulate the rate at which certain populations of cells multiply or differentiate, and improve the effectiveness of these expansion systems in generating cells needed for transplant.

It is also believed that neurturin can be used for the ex vivo expansion of precursor cells in the nervous system. Transplant or engraftment of cells is currently being explored as a therapy for diseases in which certain populations of neurons are lost due to degeneration such as, for example, in parkinson's disease (Bjorklund, *Curr Opin Neurobiol* 2:683–689, 1992 which is incorporated by reference). Neuronal precursor cells can be obtained from animal or human donors or from human fetal tissue and then expanded in culture using neurturin or other growth factors. These cells can then be engrafted into patients where they would function to replace some of the cells lost due to degeneration. Because neurotrophins have been shown to be capable of stimulating the survival and proliferation of neuronal precursors cells such as, for example, NT-3 stimulation of sympathetic neuroblast cells (Birren et al., *Develop* 119:597–610, 1993 which is incorporated by reference), neurturin could also function in similar ways during the development of the nervous system and could be useful in the ex vivo expansion of neuronal cells.

In a number of circumstances it would be desirable to determine the levels of neurturin in a patient. The identification of neurturin along with the present report showing that neurturin is expressed by a number of tissues provides the basis for the conclusion that the presence of neurturin serves a normal physiologic function related to cell growth and survival. Indeed, other neurotrophic factors are known to play a role in the function of neuronal and non-neuronal tissues. (For review see Scully and Otten, *Cell Biol Int* 19:459–469, 1995; Otten and Gadient, *Int J Devl Neurosciences* 13:147–151, 1995 which are incorporated by reference). Endogenously produced neurturin may also play a role in certain disease conditions, particularly where there is cellular degeneration such as in neurodegenerative conditions or diseases. Other neurotrophic factors are known to change during disease conditions. For example, in multiple sclerosis, levels of NGF protein in the cerebrospinal fluid are increased during acute phases of the disease (Bracci-Laudiero et al., *Neuroscience Lett* 147:9–12, 1992 which is incorporated by reference) and in systemic lupus erythematosus there is a correlation between inflammatory episodes and NGF levels in sera (Bracci-Laudiero et al. *NeuroReport* 4:563–565, 1993 which is incorporated by reference).

Given that neurturin is expressed in blood cells, bone marrow and mast cells, it is likely that the level of neurturin may be altered in a variety of conditions and that quantification of neurturin levels would provide clinically useful information. Furthermore, in the treatment of degenerative conditions, compositions containing neurturin can be administered and it would likely be desirable to achieve certain target levels of neurturin in sera, in cerebrospinal fluid or in any desired tissue compartment. It would, therefore, be advantageous to be able to monitor the levels of neurturin in a patient. Accordingly, the present invention also provides methods for detecting the presence of neurturin in a sample from a patient.

The term "detection" as used herein in the context of detecting the presence of neurturin in a patient is intended to include the determining of the amount of neurturin or the ability to express an amount of neurturin in a patient, the distinguishing of neurturin from other growth factors, the estimation of prognosis in terms of probable outcome of a degenerative disease and prospect for recovery, the monitoring of the neurturin levels over a period of time as a measure of status of the condition, and the monitoring of neurturin levels for determining a preferred therapeutic regimen for the patient.

To detect the presence of neurturin in a patient, a sample is obtained from the patient. The sample can be a tissue biopsy sample or a sample of blood, plasma, serum, CSF or the like. Neurturin is expressed in a wide variety of tissues as shown in example 9. Samples for detecting neurturin can be taken from any of these tissues. When assessing peripheral levels of neurturin, it is preferred that the sample be a sample of blood, plasma or serum. When assessing the levels of neurturin in the central nervous system a preferred sample is a sample obtained from cerebrospinal fluid.

In some instances it is desirable to determine whether the neurturin gene is intact in the patient or in a tissue or cell line within the patient. By an intact neurturin gene it is meant that there are no alterations in the gene such as point mutations, deletions, insertions, chromosomal breakage, chromosomal rearrangements and the like wherein such alteration might alter production of neurturin or alter its biological activity, stability or the like to lead to disease processes or susceptibility to cellular degenerative conditions. Thus, in one embodiment of the present invention a method is provided for detecting and characterizing any alterations in the neurturin gene. The method comprises providing an oligonucleotide that contains the neurturin cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the neurturin gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact neurturin gene or a neurturin gene abnormality.

Hybridization to the neurturin gene would involve denaturing the chromosomal DNA to obtain a single-stranded DNA; contacting the single-stranded DNA with a gene probe associated with the neurturin gene sequence; and identifying the hybridized DNA-probe to detect chromosomal DNA containing at least a portion of the human neurturin gene.

The term "probe" as used herein refers to a structure comprised of a polynucleotide which forms a hybrid structure with a target sequence, due to complementarity of probe sequence with a sequence in the target region. Oligomers suitable for use as probes may contain a minimum of about 8–12 contiguous nucleotides which are complementary to the targeted sequence and preferably a minimum of about 20.

The neurturin gene probes of the present invention can be DNA or RNA oligonucleotides and can be made by any method known in the art such as, for example, excision, transcription or chemical synthesis. Probes may be labelled with any detectable label known in the art such as, for example, radioactive or fluorescent labels or enzymatic marker. Labeling of the probe can be accomplished by any method known in the art such as by PCR, random priming, end labelling, nick translation or the like. One skilled in the art will also recognize that other methods not employing a labelled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25°–45° C., more preferably at 32°–40° C. and more preferably at 37°–38° C. The time required for hybridization is from about 0.25 to about 96 hours, more preferably from about one to about 72 hours, and most preferably from about 4 to about 24 hours.

Neurturin gene abnormalities can also be detected by using the PCR method and primers that flank or lie within the neurturin gene. The PCR method is well known in the art. Briefly, this method is performed using two oligonucleotide primers which are capable of hybridizing to the nucleic acid sequences flanking a target sequence that lies within a neurturin gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising neurturin or pre-pro neurturin or a fragment thereof is then directly sequenced and analyzed by comparison of the sequence with the sequences disclosed herein to identify alterations which might change activity or expression levels or the like.

In another embodiment a method for detecting neurturin is provided based upon an analysis of tissue expressing the neurturin gene. Certain tissues such as those identified below in example 9 have been found to express the neurturin gene. The method comprises hybridizing a polynucleotide to mRNA from a sample of tissues that normally express the neurturin gene. The sample is obtained from a patient suspected of having an abnormality in the neurturin gene or in the neurturin gene of particular cells. The polynucleotide comprises SEQ ID NO:11 or a derivative thereof or a fragment thereof.

To detect the presence of mRNA encoding neurturin protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a DNA sequence serving as a probe to form hybrid duplexes. The use of a labeled probes as discussed above allows detection of the resulting duplex.

When using the cDNA encoding neurturin protein or a derivative of the cDNA as a probe, high stringency conditions can be used in order to prevent false positives, that is the hybridization and apparent detection of neurturin nucleotide sequences when in fact an intact and functioning neurturin gene is not present. When using sequences derived from the neurturin cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook, et al., 1989, supra).

Figure 6:
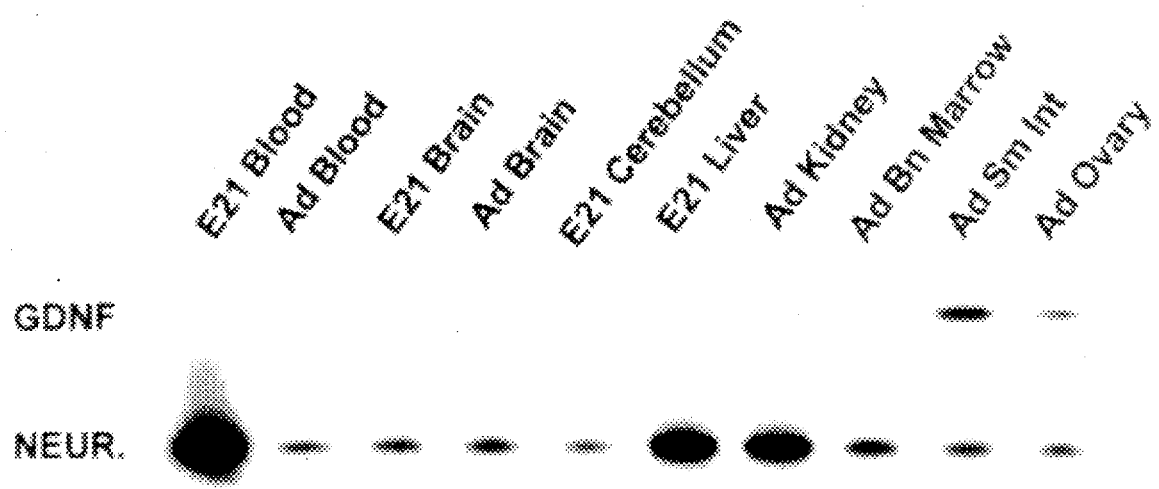
FIG. 6 illustrates the tissue distribution of neurturin mRNA and the mRNA for GDNF using RT/PCR analysis on RNA samples obtained from embryonic day 21 (E21) and adult rats.

In order to increase the sensitivity of the detection in a sample of mRNA encoding the neurturin protein, the technique of reverse transcription/polymerization chain reaction (RT/PCR) can be used to amplify cDNA transcribed from mRNA encoding the neurturin protein. The method of RT/PCR is well known in the art (see example 9 and FIG. 6 below).

The RT/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and neurturin specific primers. (Belyavsky et al, *Nucl Acid Res* 17:2919–2932, 1989; Krug and Berger, *Methods in Enzymology*, Academic Press, N.Y., Vol.152, pp. 316–325, 1987 which are incorporated by reference).

The polymerase chain reaction method is performed as described above using two oligonucleotide primers that are substantially complementary to the two flanking regions of the DNA segment to be amplified.

Following amplification, the PCR product is then electrophoresed and detected by ethidium bromide staining or by phosphoimaging.

The present invention further provides for methods to detect the presence of the neurturin protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology*, Sites and Terr, eds., Appleton & Lange, Norwalk, Conn. pp 217–262, 1991 which is incorporated by reference). Preferred are binder-ligand immunoassay methods including reacting antibodies with an epitope or epitopes of the neurturin protein and competitively displacing a labeled neurturin protein or derivative thereof.

As used herein, a derivative of the neurturin protein is intended to include a polypeptide in which certain amino acids have been deleted or replaced or changed to modified or unusual amino acids wherein the neurturin derivative is biologically equivalent to neurturin and wherein the polypeptide derivative cross-reacts with antibodies raised against the neurturin protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, enzyme-linked immunosorbent assay (ELISA), fluorescent immunoassays and the like.

Polyclonal or monoclonal antibodies to the neurturin protein or an epitope thereof can be made for use in immunoassays by any of a number of methods known in the art. By epitope reference is made to an antigenic determinant of a polypeptide. An epitope could comprise 3 amino acids in a spacial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse (See Example 10).

Oligopeptides can be selected as candidates for the production of an antibody to the neurturin protein based upon the oligopeptides lying in hydrophilic regions, which are thus likely to be exposed in the mature protein.

Antibodies to neurturin can also be raised against oligopeptides that include one or more of the conserved regions identified herein such that the antibody can cross-react with other family members. Such antibodies can be used to identify and isolate the other family members.

Methods for preparation of the neurturin protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J Am Chem Soc* 85:2149, 1963 which is incorporated by reference) or the FMOC strategy on a Rapid Automated Multiple Peptide Synthesis system (DuPont Company, Wilmington, Del.) (Caprino and Han, *J Org Chem* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified neurturin protein usually by ELISA or by bioassay based upon the ability to block the action of neurturin on neurons or other cells. When using avian species, e.g. chicken, turkey and the like, the antibody can be isolated from the yolk of the egg. Monoclonal antibodies can prepared after the method of Milstein and Kohler by fusing splenocytes from immunized mice with continuously replicating tumor cells such as myeloma or lymphoma cells. (Milstein and Kohler *Nature* 256:495–497, 1975; Gulfre and Milstein, *Methods in Enzymology: Immunochemical Techniques* 73:1–46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an over expression of the protein. Thus, another aspect of the present invention provides for a method for preventing or treating diseases involving over expression of the neurturin protein by treatment of patient with specific antibodies to the neurturin protein.

Specific antibodies, either polyclonal or monoclonal, to the neurturin protein can be produced by any suitable method known in the art as discussed above. For example, murine or human monoclonal antibodies can be produced by hybridoma technology or, alternatively, the neurturin protein, or an immunologically active fragment thereof, or an anti-idiotypic antibody, or fragment thereof can be administered to an animal to elicit the production of antibodies capable of recognizing and binding to the neurturin protein. Such antibodies can be from any class of antibodies including, but not limited to IgG, IgA, IgM, IgD, and IgE or in the case of avian species, IgY and from any subclass of antibodies.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the isolation and purification of neurturin from CHO cell conditioned medium.
Preparation of CHO cell conditioned medium A derivative of DG44 Chinese hamster ovary cells, DG44CHO-pHSP-NGFI-B (CHO) cells, was used (Day et al, *J Biol Chem* 265:15253–15260, 1990 which is incorporated by reference). As noted above, the inventors have also obtained neurturin in partially purified form from other derivatives of DG44 Chinese hamster ovary cells. The CHO cells were maintained in 20 ml medium containing minimum essential medium (MEM) alpha (Gibco-BRL No. 12561, Gaithersburg, Md.) containing 10% fetal calf serum (Hyclone Laboratories, Logan, Utah), 2 mM 1-glutamine, 100 U/ml penicillin, 100 µg/ml streptomycin and 25 nM methotrexate using 150 cm² flasks (Corning Inc., Corning N.Y.). For passage and expansion, medium from a confluent flask was aspirated; the cells were washed with 10 ml phosphate buffered saline (PBS) containing in g/l, 0.144 $KH_2PO_4$, 0.795 $Na_2HPO_4$ and 9.00 NaCl; and the flask was then incubated for 2-3 minutes with 2 ml 0.25% trypsin in PBS. Cells were then knocked off the flask surface, 8 ml of medium were added and cells were triturated several times with a pipette. The cells were split 1:5 or 1:10, incubated at 37° C. under an atmosphere of 5% $CO_2$ in air and grown to confluence for 3-4 days.

The cell culture was then expanded into 850 cm² roller bottles (Becton Dickinson, Bedford, Mass.). A confluent 150 cm² flask was trypsinized and seeded into one roller bottle containing 240 ml of the above modified MEM medium without methotrexate. The pH was maintained either by blanketing the medium with 5% $CO_2$ in air or by preparing the medium with 25 mM HEPES pH 7.4 (Sigma, St. Louis, Mo.). The roller bottles were rotated at 0.8-1.0 revolutions per minute. Cells reached confluence in 4 days.

For collecting conditioned medium, serum-free CHO cell (SF-CHO) medium was used. SF-CHO was prepared using 1:1 DME/F12 base medium, which was prepared by mixing 1:1 (v/v) DMEM (Gibco-BRL product No. 11965, Gibco-BRL, Gaithersburg, Md.) with Ham's F12 (Gibco-BRL product No. 11765). The final SF-CHO medium contained 15 mM HEPES pH 7.4 (Sigma, St. Louis, Mo.), 0.5 mg/ml bovine serum albumin (BSA, Sigma, St. Louis Mo.), 25 µg/ml heparin, (Sigma, St. Louis, Mo.), 1×insulin-transferrin-selenite supplement (bovine insulin, 5 µg/ml; human transferrin, 5 µg/ml; sodium selenite, 5 ng/ml; Sigma, St. Louis, Mo.), 2 mM 1-glutamine, 100 U/ml penicillin, and 100 µg/ml streptomycin. The medium from the confluent roller bottles was removed and the cells washed once with 30 ml SF-CHO medium to remove serum proteins. Cells were then incubated at 37° C. for 16-24 hrs in 80 ml SF-CHO medium to further remove serum proteins. The 80 ml medium was removed and discarded. A volume of 120 ml of SF-CHO medium was added to the flask and the cells incubated at 37° C. Every 48 hrs thereafter, 120 ml was collected and replaced with the same volume of SF-CHO medium.

Collected media was pooled and centrifuged at 4° C. in polypropylene conical tubes to remove cellular debris and the supernatant stored at −70° C. Media was collected 5 times over 10 days to yield a total of approximately 600 ml conditioned medium per roller bottle.

Fractions collected from the columns at each stage of purification were assayed for biological activity using the neuronal survival assay and for protein content by the dye binding assay of Bradford (*Anal Biochem* 72:248 et seq., 1976 which is incorporated by reference). The total mg of protein in the starting volume, typically 50 liters, of conditioned medium was determined.

Superior Cervical Ganglion Survival Assay

The neurotrophic activity of CHO conditioned medium starting material and at various stages of purification was assessed using the superior cervical ganglion survival assay system previously reported (Martin, et al *J of Cell Biology* 106:829-844; Deckwerth and Johnson, *J Cell Bio* 123:1207-1225, 1993 which are incorporated by reference). Primary cultures of sympathetic neurons from superior cervical ganglion (SCG) were prepared by dissecting tissue from Day 20-21 rat embryo (E20-E21). The SCG's were placed in Leibovitz's L15 with 1-glutamine medium (Cat #11415-053 Gibco-BRL, Gaithersburg, Md.), digested for 30 minutes with 1 mg/ml collagenase (Cat #4188 Worthington Biochemical, Freehold, N.J.) in Leibovitz's L15 medium at 37° C., followed by a 30 minute digestion in trypsin-lyophilized & irradiated (Type TRLVMF Cat #4454 Worthington Biochemical, Freehold, N.J.) which was resuspended in modified Hanks' Balanced Salt Solution (Cat #H-8389 Sigma Chemical Co., St. Louis, Mo.). The digestion was stopped using AM50 which contains Minimum Essential Medium with Earle's salts and without 1-glutamine (Cat #11090-016 Gibco-BRL), 10% fetal calf serum (Cat #1115 Hyclone Laboratories, Logan, Utah), 5 mM 1-glutamine (Cat #G5763 Sigma Chemical Co., St. Louis, Mo.), 20 µM FuDr (F-0503 Sigma Chemical Co., St. Louis, Mo.), 20 µM Uridine (Cat #3003 Sigma Chemical Co., St. Louis, Mo.), 100 U/ml penicillin, 100 µg/ml Streptomycin, and 50 ng/ml 2.5 S NGF. The cells were dissociated into a suspension of single cells using a silanized and flame-polished Pasteur piper. After filtration of the suspension through a nitex filter (size 3-20/14, Tetko Inc., Elmsford, N.Y.), the cells were placed in AM50 medium as above and preplated on a 100 mm Falcon or Primaria culture dish (Becton Dickinson Labware, Lincoln Park, N.J.) to reduce the number of non-neuronal cells. After 2 hours, the medium containing the unattached neuronal cells was removed from these dishes and triturated again through a silanized and flame-polished Pasteur pipet. The single cell suspension was plated on 24-well tissue culture plates (Costar, Wilmington, Mass.) that have been previously coated with a double layer of collagen, one layer of collagen that had been ammoniated and a second layer of collagen that had been air dried. They were allowed to attach for 30 minutes to 2 hours. A specific number of viable cells, usually about 1200 to about 3000 total cells per well, or a specific percentage of the ganglion, usually 25% of the cells obtained per ganglion were plated into each well. When cell counts were to be performed they were placed in the 24-well dishes as stated above or alternatively, on 2-well chamber slides (Nunc, Naperville, Ill.). Cultures were then incubated for 5-6 days at 37° in AM50 medium in a 5% $CO_2$/95% air atmosphere. The death of the cultured neurons was induced by exchanging the medium with medium without NGF and with 0.05% goat anti-NGF (final titer in the wells is 1:10). This NGF-deprivation results in death of the neurons over a period of 24-72 hours. Aliquots of partially purified or purified factor, or appropriate controls, were added to the cultures at the time of NGF removal to determine the ability to prevent the neuronal death.

Evaluation of the ability of column fraction, gel eluates, or purified factor to prevent neuronal death was by visual inspection of cultures under phase contrast microscopy. Viable neurons remained phase bright with intact neurites, whereas dead neurons were shrunken, phase dark, had irregular membranes and neurites were fragmented (FIG. 3). Where precise quantitation of neuronal survival was required, the cultures were fixed in 4% paraformaldehyde or 10% Formalin in PBS, and stained with crystal violet solution, (Huntoon Formula Harleco E.M. Diagnostics Systems, Gibbstown, N.J.). When using 24 well dishes, 1 µl crystal violet solution was added to each well containing 10% formalin and the cells were counted using a phase contrast microscope. If the 2-well chamber slides were used, the cultures were fixed, stained with crystal violet, destained with water, dehydrated in increasing ethanol concentrations to toluene, and mounted in a toluene-based mounting solution. Neurons were scored as viable if they had a clear nucleolus and nuclei and were clearly stained with crystal violet.

The neuronal death at 72 hours in shown in FIG. 3B. Also shown are (A) the positive control cells maintained with nerve growth factor and (C) the cells treated with anti-NGF and neurturin (approximately 3 ng/ml) showing survival of neurons.

Activity was quantitated by calculation of a "survival unit". The total survival units in a sample were defined as the minimal volume of an aliquot of the sample which produced maximal survival divided into the total volume of that sample. Specific activity was calculated as the survival units divided by the mg total protein.

Survival units were determined in an assay using approximately 1200 viable neurons in a 0.5 ml culture assay and a culture period of 48 hours following addition of the fraction. Survival was assessed visually after the 48 hours. Intrinsic activity as shown in FIG. 4 was determined in an assay using approximately 2700 neurons and a culture period of 72 hours. Survival was assessed by fixing the neurons and counting the number of surviving neurons. Because the stability, as assessed by half-life of activity, for neurturin decreases as the number of neurons increases, the intrinsic activity measurement would be expected to be lower than that predicted by Specific Activity determinations. The intrinsic activity measurement would also be expected to be lower than that predicted by specific activity because the survival was measured after 72 hours instead of 48 hours.

To ensure the reproducibility of these activity unit assays, it was necessary to plate the primary neuronal cultures at reproducible cell densities, as the stability of the activity decreases significantly with increasing neuronal density. The range of cell densities was from about 1200 to about 2700 cells per well. The presence of soluble heparin in the assay medium had no effect on the short-term (~3 days) stability of the survival activity.

Purification of Neurturin

Pooled conditioned medium was filtered through 0.2 μl pore bottle-top filters (cellulose acetate membrane, Corning Inc., Corning, N.Y.). Typically 50 liters of conditioned medium was used and processed in 25 liter batches. Each 25 liter batch was introduced at a rate of 20 ml/min onto a 5×5 cm column containing 100 ml heparin-agarose (Sigma, St. Louis, Mo.) equilibrated with 25 mM HEPES, pH 7.4 buffer with 150 mM NaCl. The column was then washed with approximately 1000 ml 25 mM HEPES, pH 7.4 buffer containing 0.5M NaCl at 20 ml/min and the activity was then eluted with 25 mM HEPES, pH 7.4 buffer containing 1.0M NaCl. After switching to the 1.0M NaCL elution buffer, the first 50 ml of buffer was discarded and, thereafter, one 300 ml fraction was collected.

Pooled material eluted from the Heparin-agarose column was then diluted 1:1 (v/v) with 25 mM HEPES, pH 7.4 buffer containing 0.04% TWEEN 20 to a NaCl concentration of 0.5M and introduced into a 1.5 cm×9 cm column containing 16 ml SP SEPHAROSE® High Performance ion exchange resin (Pharmacia, Piscataway, N.J.) equilibrated in 25 mM HEPES 7.4 containing 0.5M NaCl and 0.02% TWEEN 20. The column was then washed with 160 ml 25 mM HEPES, pH 7.4 buffer containing 0.5M NaCl and 0.02% TWEEN 20 and the activity was eluted with 25 mM HEPES, pH 7.4 buffer containing 1.0M NaCl and 0.02% TWEEN 20 at a flow rate of 2 ml/min. One 50 ml fraction was collected after the first 7 ml of eluate from the column.

Material eluted from the SP SEPHAROSE® column was fractionated using fast protein liquid chromatography (FPLC) on a Chelating Superose HR 10/2 column charged with $Cu^{++}$ (Pharmacia, Piscataway, N.J.). The column had been prepared by washing with 10 ml water, charging with 3 ml of 2.5 mg/ml $CuSO_4 \cdot 5H_2O$, washing with 10 ml water, and equilibrating with 10 ml of 25 mM HEPES pH 7.4 buffer containing 1.0M NaCl and 0.02% TWEEN 20. The eluate was introduced into the column in 25 mM HEPES, pH 7.4 buffer containing 1.0M NaCl at a rate of 1.0 ml/min. The bound proteins were eluted with a linear gradient of increasing glycine concentration (0–300 mM) in 25 mM HEPES, pH 7.4 buffer containing 1.0M NaCl at a rate of 1.0 ml/min. The gradient was produced by a Pharmacia FPLC system using an LCC-500 controller and P-500 pumps to establish a 0–300 mM glycine gradient in 40 ml at 1.0 ml/min, thus increasing the gradient by 7.5 mM glucine per min. One ml fractions were collected and assayed for SCG survival promotion. Peak activity was observed in fractions 17–20, i.e. 17–20 min or ml from the start of the gradient.

Absorbance measurements at 280 nM by an in-line UV monitor indicated that most proteins eluted prior to the survival activity in fractions 17–20. Thus, significant purification was achieved at this step. A 25 kD band co-purified with the survival activity.

The combined eluted fractions from the $Cu^{++}$ superose column were diluted to 0.45M NaCl using 25 mM HEPES pH 7.4 buffer containing 0.02% TWEEN 20 and introduced into a Mono S HR 5/5 cation exchange column (Pharmacia, Piscataway, N.J.) for further FPLC purification. The column had been equilibrated with 25 mM HEPES pH 7.4 buffer containing 0.45M NaCl containing 0.02% TWEEN 20. Bound proteins were eluted with a linear gradient of increasing NaCl concentration (0.45–1.0M). The gradient was produced as described above from 0.45M–1.0M NaCl in 35 mls at 1.0 ml/min, thus increasing concentration at 0.0157M per ml or min. Thirteen 1.0 ml fractions (fractions 1–13) were collected followed by 44 0.5 ml fractions (fractions 14–53). Peak activity in SCG assay was in fractions 26–29. Each fraction was assayed in the SCG survival assay over a range of volumes of from 0.1 to 1.0 μl per 0.5 ml culture medium.

Figure 2A:
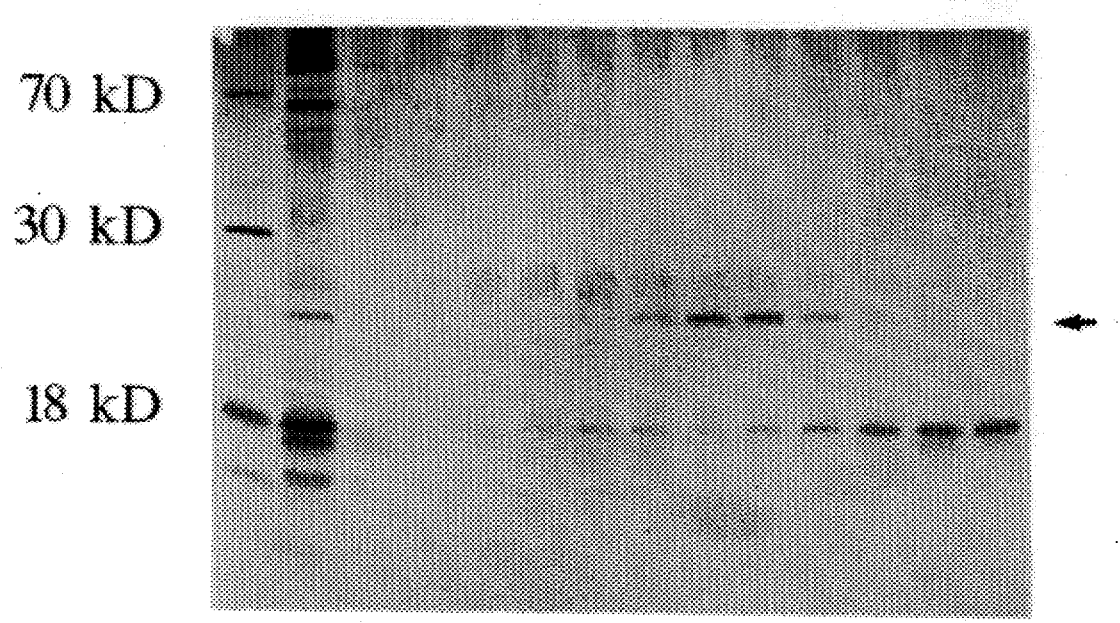
FIG. 2 illustrates the characterization of fractions eluted from Mono S column in purifying neurturin showing (a) electrophoresis of each fraction on a SDS-polyacrylamide gel and visualization of the proteins by silver stain and (b) the neurotrophic activity present in each fraction in the superior cervical ganglion survival assay.
Figure 2B:
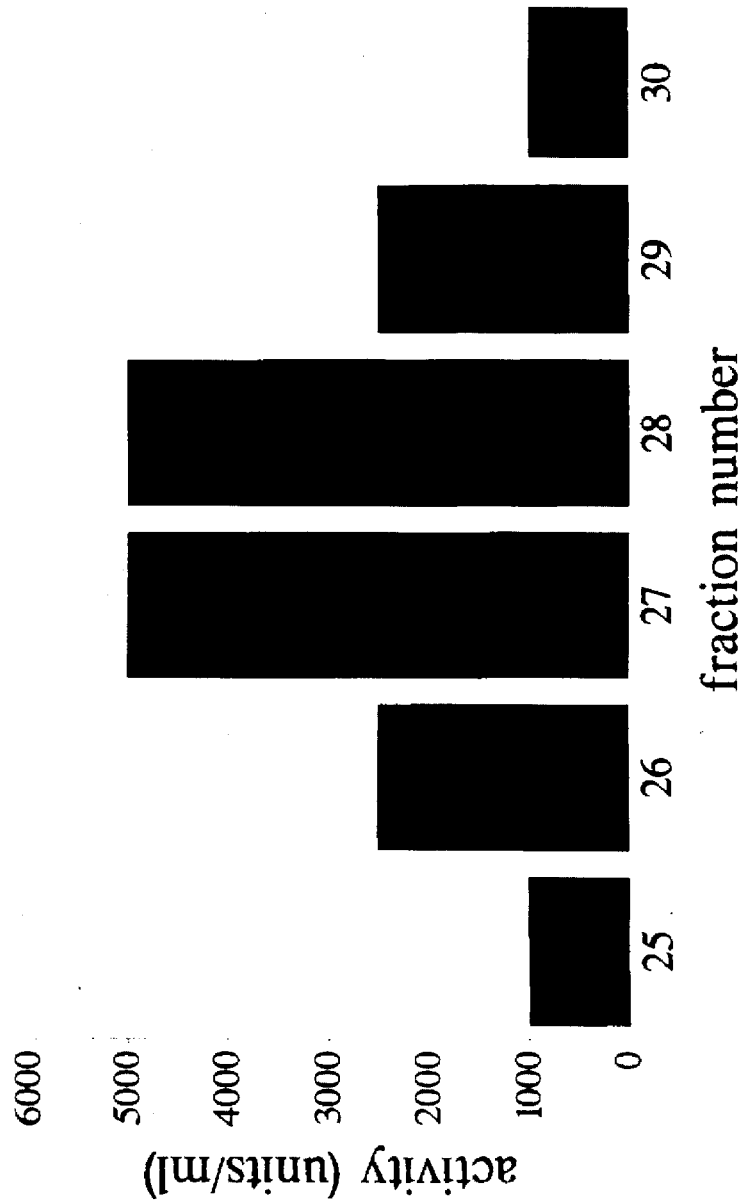

One percent (5 μl) of each fraction was loaded onto a non-reducing, 14% SDS polyacrylamide gel and electrophoresed for 750 V-hr at 25° C. Proteins were visualized by silver stain. The results are shown in FIG. 2. Markers shown in lane M on the gel represent 20 ng of Bovine serum albumin, carbonic anhydrase, B-lactoglobulin, and lysozyme in the order of descending molecular weight.

A 25 kD band appeared in fractions 25–30, a 28 kD protein elutes earlier in the gradient and an 18 kD elutes later in the gradient. FIG. 2 illustrates the survival activity in each of the fractions. The survival activity is noted to correspond with the presence and apparent intensity of the 25 kD protein in fractions 25–30.

To demonstrate that the 25 kD band was responsible for survival promoting activity, the 25 kD protein was eluted from the polyacrylamide gel after electrophoresis and assayed for survival activity in the SCG assay. After electrophoresis of 150 μl of the SP SEPHAROSE® 1.0M NaCl fraction in one lane of a non-reducing 14% SDS-polyacrylamide gel as above, the lane was cut into 12 slices and each slice was crushed and eluted by diffusion with rocking in buffer containing 25 mM HEPES, pH 7.4, 0.5M NaCl, 0.02% Tween-20 for 18 hr at 25° C. BSA was added to the eluate to a final concentration of 200 μg/ml and the eluate was filtered through a 0.45 micron filter to remove acrylamide gel fragments. The filtrate was then added to a SP SEPHAROSE® column to concentrate and purify the sample. Before eluting the sample, the column was washed once in 400 μl 25 mM HEPES, pH 7.4 buffer containing 0.5M NaCl, 0.02% Tween-20 and 200 μg BSA per ml and once in 400 µl 25 mM HEPES, pH 7.4 buffer containing 0.02% Tween-20 and 200 µg BSA per ml. The column was then washed again in 400 µl of 25 mM HEPES, pH 7.4 buffer containing 0.5M NaCl, 0.02% TWEEN 20 and 200 ug BSA per ml. The sample was eluted with 25 mM HEPES, pH 7.4 buffer containing 1.0M NaCl, 0.02% Tween-20 and 200 µg BSA per ml. Samples were then analyzed for survival activity. Only the slice corresponding to the 25 kD band showed evidence of survival activity. The 25 kD protein purified from CHO cell conditioned media is believed to be a homodimer.

The yield from the purification above was typically 1–1.5 µg from 50 liters of CHO cell conditioned medium. Overall recovery is estimated to be 10–30%, resulting in a purification of approximately 390,000 fold.

EXAMPLE 2

This example illustrates the characterization of neurturin and several members of the TGF-β family of growth factors in the SCG assay and the lack of cross reactivity of anti-GDNF antibodies with neurturin.

The SCG assay of the purified protein indicated that the factor is maximally active at a concentration of approximately 3 ng/ml or approximately 100 pM and the $EC_{50}$ was approximately 1.5 ng/ml or approximately 50 pM in the expected range for a diffusible peptide growth factor (FIG. 4).

Several members of the TGF-β family influence neuropeptide gene expression in sympathetic neurons, while others promote survival of different neuronal populations. Neurturin, which is a distant member of this family of proteins, is capable of promoting virtually complete survival of sympathetic neurons for 3 days. In addition, further culturing of the SCG cells revealed that neurturin could continue to maintain these neurons for at least 10 days after withdrawal of NGF.

We tested several other members of the TGF-β family for their ability to promote survival in the SCG assay including TGF-β1, activin, BMP-2, BMP-4, BMP-6 and GDNF. Of these factors, only GDNF had survival promoting activity, however, the activity of GDNF was much less potent than neurturin in this activity showing an $EC_{50}$ of 2–4 nM in the 3-day survival assay. The GDNF tested in this assay was rhGDNF produced in *E. Coli* obtained from Prepro Tech, Inc., Rocky Hill, N.J. The duration of action of GDNF was also less than that of neurturin inasmuch as the ability of GDNF (50 ng/ml) to maintain survival longer than 3 days was substantially diminished. These experiments suggest the possibility that GDNF is a weak agonist for the neurturin receptor. Furthermore, the inability of activin and BMP-2 to promote survival, in contrast to their strong induction of transmitter-related gene expression in these neurons (Fann and Paterson, *Int J Dev Neurosci* 13:317–330, 1995; Fann and Patterson, *J Neurochem* 61:1349–1355, 1993) suggests that they signal through alternate receptors or signal transduction pathways.

To determine the cross-reactivity of anti-GDNF antibodies with partially purified neurturin, SCG neurons, that had been dissected and plated as described in Example 1 were treated on Day 6 with 1 ng/ml, 3 ng/ml, 10 ng/ml, or 30 ng/ml GDNF (Prepro Tech, Inc, Rocky Hill, N.J.) in the presence of anti-NGF alone, or in the presence of anti-NGF and anti-GDNF (goat IgG antibody to *E. coli*-derived rhGDNF, R & D Systems, Minneapolis, Minn). A partially purified 1.0M SP Sepharose fraction of neurturin was used in the assay at the approximate concentrations of 375 pg/ml, 750 pg/ml, 1.5 ng/ml and 3 ng/ml. This fraction was tested in the presence of anti-NGF alone, and in the presence of anti-NGF and anti-GDNF. The anti-GDNF antibody blocked the survival promoting activity of GDNF at a concentration up to 30 ng/ml, but did not block the survival promoting activity of neurturin.

EXAMPLE 3

This example illustrates the effect of neurturin on sensory neurons in a nodose ganglion survival assay.

CHO cell conditioned media that had been partially purified on the SP Sepharose column was assayed for neurotrophic activity on sensory neurons using nodose ganglia. The survival assay is a modification of that previously reported above for superior cervical ganglia. Primary dissociated cultures of nodose ganglia were prepared by dissecting tissue from E18 Sprague Dawley rat pups. The nodose ganglia were placed in Leibovitz's L15 with 2 mM 1-glutamine (Cat#11415-023, GIBCO-BRL, Gaithersburg, Md.) as the tissues was dissected, digested for 30 min with 1 mg/ml collagenase (Cat#4188, Worthington Biochemical, Freehold, N.J.) in Leibovitz's L15 medium at 37° C., followed by 30 min digestion in trypsin (lyophilized and irradiated, type TRLVMF, Cat #4454 Worthington Biochemical, Freehold, N.J.), and resuspension to a final concentration of 0.25% in modified Hank's Balanced Salt Solution (Cat#H8389, Sigma Chemical Co., St. Louis, Mo.). The digestion was stopped using AMO-BDNF100, a medium containing Minimum Essential Medium with Earle's salts and without 1-glutamine (#11090-016 GIBCO-BRL), 10% fetal Calf Serum (Cat#1115, Hyclone Laboratories, Logan, Utah), 2 mM 1-glutamine (Cat#G5763 Sigma Chemical Co., St. Louis, Mo.), 20 µM FuDr (F-0503, Sigma Chemical Co.), 20 µM Uridine (Cat #3003, Sigma Chemical Co., St. Louis, Mo.) 100 U/ml penicillin, 100 µg/ml Streptomycin, and 100 ng Brain Derived Neurotropic Factor (BDNF, Amgen, Thousand Oaks, Calif.). The cells were dissociated into a suspension of single cells using a silanized and flame-polished Pasteur pipet in the AMO-BDNF100 medium, and preplated on a 100 mm Falcon or Primaria culture dish (Becton Dickinson Labware, Lincoln Park, N.J.) to remove non-neuronal cells. After 2 hours, the medium containing the unattached neuronal cells was removed from these dishes and triturated again through a silanized and flame-polished Pasteur piper. The single cell suspension was plated on 24-well tissue culture plates (Costar, Wilmington, Mass.) that have been previously coated with a double layer of collagen, one layer of which had been ammoniated and a second layer that had been air dried. Ganglia from ten E18 rat embryos were dissociated into 2.5 mls of media and 100 µl of this suspension was added to each well. The cells were allowed to attach for 30 min in a 37° C. incubator with 5% $CO_2$/95% air. The wells were fed with AMO-BDNF100 media overnight.

The next day the cells were washed 3 times for 20 min each time with AMO medium containing no BDNF. The wells were fed with 0.5 ml of this media alone or this media containing either 50 ng/ml NGF, 100 ng/ml BDNF (Amgen, Thousand Oaks, Calif.), 100 ng/ml GDNF (Prepro Tech, Inc., Rocky Hill, N.J.) or 3 ng/ml Neurturin. The cells were incubated at 37° C. in a 5% $CO_2$/95% air incubator for 3 days, fixed with 10% formalin, stained with crystal violet (1 µl/ml 10% formalin) and counted. Survival was ascertained as noted previously.

Figure 10:
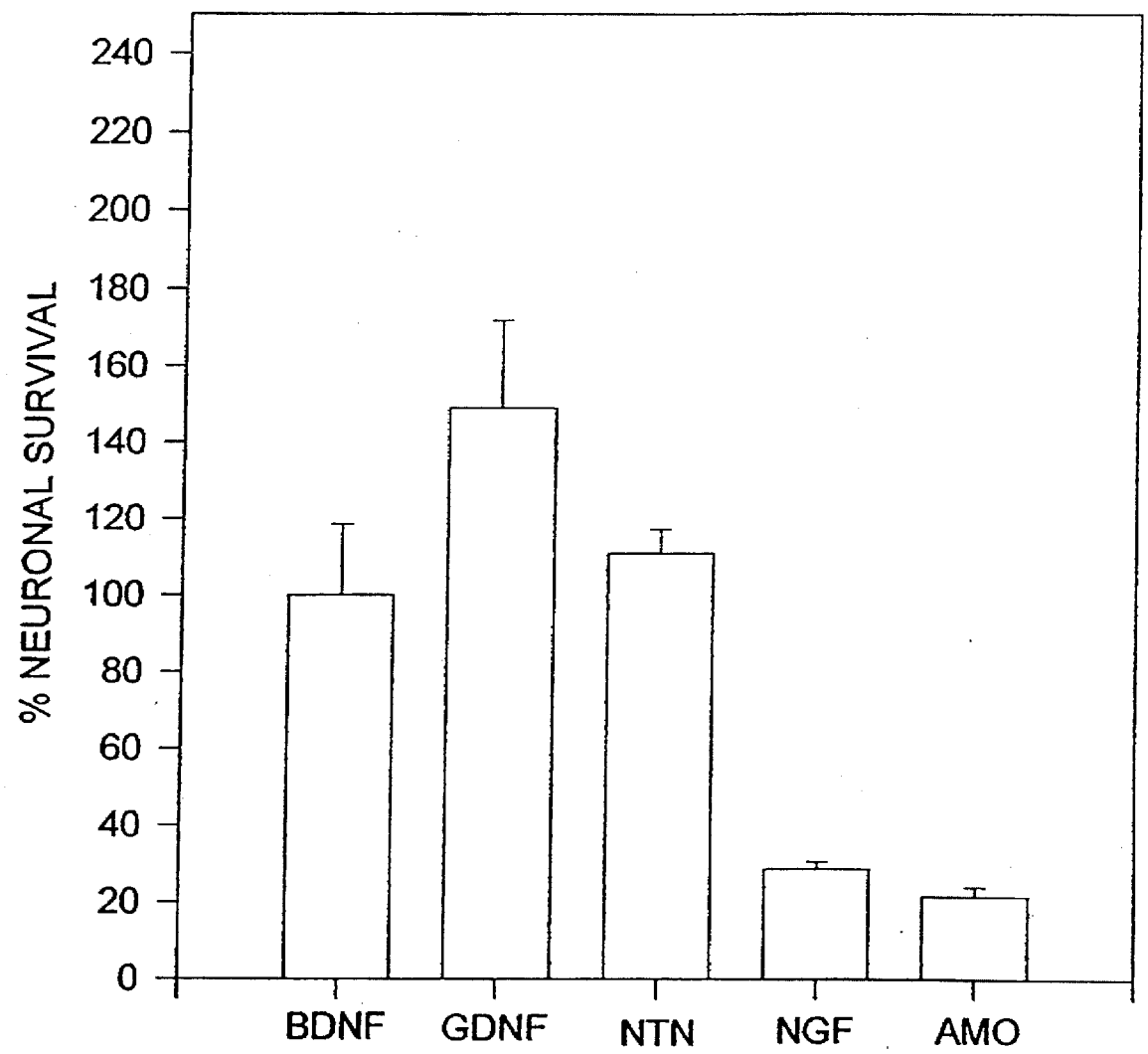
FIG. 10 illustrates the percent neuronal survival in E18 rat nodose ganglia neurons treated 24 hours post-plating for NTN, GDNF, BDNF, NGF and AMO.

The neuronal Death at 72 hours is shown in FIG. 10. Neuronal survival of nodose neurons cultured in BDNF has been previously reported (Thaler et al, *Develop Biol* 161:338–344, 1994 which is incorporated by reference). This was used as the standard for survival for these neurons and given the value of 100% survival. Nodose ganglia that had no trophic support (AMO) showed 20%–30% survival, as did neurons that were cultured in the presence of 50 ng/ml NGF. Neurons cultured in the presence of 3 ng/ml neurturin and absence of BDNF showed survival similar to those neurons cultured in the presence of BDNF (100 ng/ml). GDNF at a concentration of 100 ng/ml promoted greater survival of nodose neurons than did BDNF (100 ng/ml). Similar findings with GDNF were recently reported for sensory neurons from chicken (Ebendal, T. et al, *J Neurosci Res* 40:276–284 1995 which is incorporated by reference).

EXAMPLE 4

This example illustrates the determination of partial amino acid sequences of neurturin isolated from CHO cell conditioned medium.

To obtain N-terminal amino acid sequence from a purified preparation of approximately 1 µg of neurturin, the Mono S fractions 26–29 containing the peak of activity were concentrated to 25 µl by centrifuge ultrafiltration in a microcon-3 concentrators (Amicon, Inc., Beverley, Mass.) and loaded onto a non-reducing 14% SDS polyacrylamide gel. After electrophoretic separation, proteins were electroblotted to a PVDF membrane (Bio-Rad, Hercules, Calif.) and stained with 0.1% Coomassie Blue. The 25 kD band was excised and inserted into the reaction cartridge of an automated sequencer (Model 476, Applied Biosystems (Foster City, Calif.). Phenylthiohydantoin-amino acid (PTH-aa) recovery in the first 2–3 cycles of automated sequencing by Edman degradation indicated a sequencing yield of 4 pmoles, which was approximately 10% of the estimated amount of protein loaded on the SDS gel.

Two N-terminal sequencing runs were performed from two 50 liter purification preparations. In the first run, 1 µg of protein in 3 pooled fractions of 1.5 ml total volume were concentrated to 25 µl and electroblotted at 100V for 2 hrs at 25° C. using an electroblot buffer of 10 mM CAPS pH 11.0 buffer (Sigma, St. Louis, Mo.) containing 5% methanol. The amino acid sequence was obtained from 13 cycles of Edman degradation and the sequencing yield was 4 pmoles as above.

In the second run, 1.5 µg of protein in 4 pooled fractions of 2.0 ml total volume were concentrated to 25 µl and electroblotted at 36V for 12 hours at 4° C. using an electroblot buffer of 25 mM Tris, 192 mM glycine, 0.04% SDS and 17% MeOH. Sequencing yield was 15 pmoles and the sequence after 16 cycles was SGARPXGLRELEVSVS (SEQ ID NO:3). The sequence obtained after 16 cycles corresponded to the shorter sequence obtained in the first run. Definite assignments could not be made at 3 of the amino acid residues in the sequence (residues 1, 6 and 11 from the N-terminal). A search of protein databases did not detect any significantly homologous sequences, suggesting that the purified factor was a novel protein.

This initial N-terminal amino acid sequence data did not enable the isolation of cDNA clones using degenerate oligonucleotides as PCR primers or probes for screening libraries. To facilitate these approaches, additional protein was purified in order to obtain internal amino acid sequence from proteolytic fragments. To obtain internal amino acid sequence from neurturin, an additional 50 liters of CHO cell conditioned medium was purified using only the first 3 chromatographic steps as outlined above, except that the gradient used to elute the Cu++ Chelating Superose column was as follows: 0–60 mM glycine (4 ml), 60 mM glycine (10 ml), 60–300 mM glycine (32 ml). Fractions No. 20–23 containing neurturin were concentrated to 25 µl by ultrafiltration (Amicon microcon 3, Amicon, Beverley, Mass.) and loaded on a non-reducing SDS polyacrylamide gel. After electrophoresis, the gel was stained with Coomassie blue and the 25 kD neurturin band was excised. Neurturin was digested in the gel slice with endoproteinase Lys-C, and the eluted proteolytic fragments were purified by reverse phase HPLC. Only one peak was observed upon HPLC separation of the eluted peptides, which yielded amino acid sequence information for 23 cycles at the 1 pmole signal level using the automated sequencer, (internal fragment P2, SEQ ID NO:5).

Amino acid analysis performed on 10% of the above sample before subjecting it to digestion had indicated that 150 pmoles of protein were present in the gel slice, consisting of 7.6% lysine and 19.5% arginine. The single low level peak from the Lys-C digestion suggested that the digestion and elution of peptides were inefficient. The same gel slice was redigested with trypsin and the eluted peptides separated by HPLC. Two peaks were observed on HPLC, resulting in the elucidation of two additional 10 residue amino acid sequences (4–5 pmole signal level, internal fragment P1, SEQ ID NO:4 and internal fragment P3, SEQ ID NO:6) that were distinct from the N-terminal and previous internal amino acid sequences. The in situ digestion, elution and purification of peptides, and peptide sequencing was performed by the W. M. Keck Foundation Biotechnology Resource Laboratory at Yale University according to standard protocols for this service.

EXAMPLE 5

The following example illustrates the isolation and sequence analysis of mouse and human neurturin cDNA clones.

Degenerate oligonucleotides corresponding to various stretches of confident amino acid sequence data were synthesized and used as primers in the polymerase chain reaction (PCR) to amplify cDNA sequences from reverse transcribed mRNA. A forward primer (M1676; 5'-CCNACNGCNTAYGARGA, SEQ ID NO:50) corresponding to peptide sequence P2 $Xaa_1$-$Xaa_2$-Val-Glu-Ala-Lys-Pro-Cys-Cys-Gly-Pro-Thr-Ala-Tyr-Glu-Asp-$Xaa_3$-Val-Ser-Phe-Leu-Ser-Val where $Xaa_1$ and $Xaa_2$ were unknown, $Xaa_3$ was Gln or Glu (SEQ ID NO:5) in combination with a reverse primer (M1677; 5'-ARYTCYTGNARNGTRTGRTA (SEQ ID NO:52) corresponding to peptide sequence P3 (Tyr-His-Thr-Leu-Gln-Glu-Leu-Ser-Ala-Arg) (SEQ ID NO:6) were used to amplify a 69 nucleotide product from cDNA templates derived from E21 rat and adult mouse brain. The PCR parameters were: 94° C. for 30 sec; 55° C. for 30 sec; 72° C. for 1 min for 35 cycles. The product was subcloned into the Bluescript KS plasmid and sequenced. All nucleotide sequencing was performed using fluorescent dye terminator technology per manufacturer's instructions on an Applied Biosystems automated sequencer Model #373 (Applied Biosystems, Foster City, Calif.). Plasmid DNA for sequencing was prepared using the Wizard Miniprep kit (Promega Corp., Madison, Wis.) according to the manufacturer's instructions. The sequence of the amplified product correctly predicted amino acid sequence data internal to the PCR primers.

Primers corresponding to the amplified sequence were used in combination with the degenerate primers in the rapid amplification of cDNA ends (RACE) technique (Frohman, M. A. *Methods in Enzymology* 218:340–356, 1993) using the Marathon RACE kit (CLONTECH, Palo Alto, Calif.) per the manufacturer's instructions, except that first strand cDNA synthesis was carried out at 50° C. using Superscript II reverse transcriptase (Gibco-BRL). Briefly, a double stranded adaptor oligonucleotide was ligated to the ends of double stranded cDNA synthesized from postnatal day 1 rat brain mRNA. Using nested forward neurturin PCR primers (M1676; 5'-CCNACNGCNTAYGARGA, SEQ ID NO:50 and 1678; 5'-GACGAGGGTCCTTCCTGGACGTACACA, SEQ ID NO:53) in combination with primers to the ligated adaptor supplied in the kit (AP1, AP2), the 3' end of the neurturin cDNA was amplified by two successive PCR reactions (1st: M1676 and AP1, using 94° C. for 30 sec, 55° C. for 30 sec and 72° C. for 2 min for 35 cycles; 2nd: M1678 and AP2 using 94° C. for 30 sec and 68° C. for 2 min for 35 cycles). A 5' portion of the rat neurturin cDNA was obtained by two successive PCR reactions using the linkered cDNA as template. The 1st reaction utilized primers M1677 (SEQ ID NO:52) and AP1; using 94° C. for 30 sec; 55° C. for 30 sec; and 72° C. for 2 min for 35 cycles. The 2nd reaction used M1679 5'-TAGCGGCTGTGTACGTCCAGGAAGGACACCTCGT (SEQ ID NO:54) and AP2 at 94° C. for 30 sec and 68° C. for 2 min for 35 cycles. These reactions resulted in a truncated form of the 5' end of the neurturin cDNA, apparently the result of premature termination of the cDNA during reverse transcription. The 5' and 3' RACE products were subcloned into the plasmid Bluescript KS and sequenced. The sequence of these 3' and 5' RACE products resulted in a partial rat neurturin cDNA sequence of 220 nt. Primers (#467921 5'-CAGCGACGACGCGTGCGCAAAGAGCG, SEQ ID NO:55; and M1679 (SEQ ID NO:54) corresponding to the partial rat cDNA sequence were used (PCR parameters 94° C. for 30 sec and 68° C. for 1 min for 35 cycles) to amplify a 101 nucleotide PCR product from mouse genomic DNA which was homologous to rat neurturin cDNA sequence.

These primers were then used to obtain murine neurturin genomic clones from a mouse 129/Sv library in a P1 bacteriophage vector (library screening service of Genome Systems, Inc., St. Louis, Mo.). A 1.6 kb Nco I fragment from this P1 clone containing the neurturin gene was identified by hybridization with primer (#465782; 5'-TAYGARGACGAGGTGTCCTTCCTGGACGTACAC-AGCCGCTAYCAYAC, SEQ ID NO:56). This Nco I fragment was sequenced and found to contain a stretch of coding sequence corresponding to the N-terminal and internal amino acid sequences obtained from sequencing the active protein isolated from CHO cell conditioned media. Beginning at the N-terminal amino acid sequence of the purified protein, this nucleotide sequence encodes a 100 amino acid protein with a predicted molecular mass of 11.5 kD. A search of protein and nucleic acid databases identified neurturin as a novel protein that is approximately 40% identical to glial derived neurotrophic factor (GDNF). GDNF was purified and cloned as a factor which promotes the survival of midbrain dopaminergic neurons and is a distantly related member of the TGF-β superfamily, which now includes more than 25 different genes that possess a wide variety of proliferative and differentiative activities. Although GDNF is less than 20% identical to any other member of the TGF-β family, it contains the 7 cysteine residues which are conserved across the entire family and believed to be the basis of a conserved cysteine knot structure observed in the crystal structure determination of TGF-β2. Neurturin also contains these 7 cysteine residues, but like GDNF is less than 20% homologous to any other member of the TGF-β family. Thus, neurturin and GDNF appear to represent a subfamily of growth factors which have significantly diverged from the rest of the TGF-β superfamily.

To determine the sequence of the full length mouse neurturin cDNA, 5' and 3' RACE PCR was performed as above for the rat, using nested primers predicted from the mouse genomic sequence and cDNA from neonatal mouse brain. The 1st reaction for the 3' end used primers: M1777 5'-GCGGCCATCCGCATCTACGACCGGG (SEQ ID NO:57) and AP1 at 94° C. for 30 sec; 65° C. for 15 sec; and 68° C. for 2 min for 35 cycles. The 2nd reaction used primer #467921 (SEQ ID NO:55) and AP2 at 94° C. for 30 sec; 65° C. for 15 sec; and 68° C. for 2 min for 20 cycles. The 5' end was obtained using for the 1st reaction primer M1759, 5'-CRTAGGCCGTCGGGCGRCARCACGGGT (SEQ ID NO:58) and AP1 at 94° C. for 30 sec; 65° C. for 15 sec; and 68° C. for 2 min for 35 cycles. The 2nd reaction used primer M1785, 5'-GCGCCGAAGGCCCAGGTCGTAGATGCG (SEQ ID NO:59) and AP2 at 94° C. for 30 sec; 65° C. for 15 sec; and 68° C. for 2 min for 20 cycles. Both Sets of PCR reactions included 5% DMSO. The 5' and 3' mouse RACE products were subcloned into the plasmid Bluescript KS and sequenced. Using the sequence of RACE products, a 1.0 kb mouse neurturin cDNA sequence can be assembled. This cDNA sequence contains an open reading frame of 585 nucleotides that encodes a protein with a molecular mass of 24 kD. This full length mouse cDNA sequence is shown in FIG. 7 (SEQ ID NO:12). Consistent with the processing events known to occur for TGF-β family members, the 24 kD neurturin protein contains an amino terminal 19 amino acid signal sequence followed by a pro-domain which contains an RXXR proteolytic processing site immediately before the N-terminal amino acid sequence obtained when sequencing the protein purified from CHO cell conditioned media. Using these landmarks, the 11.5 kD mature neurturin molecule is predicted to be 11.5 kD and, by analogy to other members of the TGF-β family, is predicted to form a disulfide linked homodimer of 23 kD, consistent with the 25 kD mass of the protein purified from CHO cell conditioned media as estimated by SDS-PAGE analysis.

For isolation of human genomic clones, primers (#467524; 5'-CGCTACTGCGCAGGCGCGTGCGARGCGGC, SEQ ID NO:60 and #10005, 5'-CGCCGACAGCTCTTGCAGCGTRTGGTA, SEQ ID NO:61) predicted from the sequence of mouse neurturin were used to amplify (PCR parameters: Initial denaturation at 95° C. for 1 min 30 sec followed by 94° C. for 30 sec; 60° C. for 15 sec; and 68° C. for 60 sec for 35 cycles) a 192 nucleotide fragment from human genomic DNA. The sequence of the PCR product demonstrated that it was the human homolog of mouse neurturin. The primers were then used to screen a human genomic library constructed in the P1 vector (library screening service, Genome Systems, Inc.) and two clones containing the human neurturin genomic locus were obtained.

The same strategy was used to determine the human sequence as discussed above for the mouse sequence. An oligo (#30152, GACCTGGGCCTGGGCTACGCGTCCGACGAG, SEQ ID NO:62) was used as a probe in a Southern blot analysis to identify restriction fragments of the P1 Clones which contained the human neurturin coding sequence. These restriction fragments (Eag I, Pvu II, Hind III, Kpn I) were subcloned into the Bluescript KS plasmid and sequenced.

The results of subcloning and sequencing of human genomic fragments were as follows. The Eag I fragment was found to be approximately 6 kb in size with the 3' Eag I site located 60 bp downstream from the stop codon. The Pvu II fragment was approximately 3.5 kb in size with the 3' Pvu II site located 250 bp downstream from the stop codon. The Hind III fragment was approximately 4.8 kb in size with the 3' Hind III site located 3 kb downstream from the stop codon. The Kpn I fragment was approximately 4.2 kb in size with the 3' Kpn I site located 3.1 kb downstream from the stop codon.

The second coding exon was sequenced using these subcloned fragments. In addition, sequence was obtained from 250 bp flanking the 3' side of the second exon. The sequence was also obtained from 1000 bp flanking the 5' side of the coding exon. From these flanking sequences, forward primer 30341 (5'-CTGGCGTCCCAMCAAGGGTCTTCG-3', SEQ ID NO:71) and reverse primer 30331 (5'-GCCAGTGGTGCCGTCGAGGCGGG-3', SEQ ID NO:72) were designed so that the entire coding sequence of the second exon could be amplified by PCR.

The first coding exon was not mapped relative to the restriction sites above but was contained in the Eag I fragment. The sequence of this exon was obtained from the subcloned Eag I fragment using the mouse primer 466215 (5'-GGCCCAGGATGAGGCGCTGGAAGG-3', SEQ ID NO:73), which contains the ATG initiation codon. Further sequence of the first coding exon was obtained with reverse primer 20215 (5'-CCACTCCACTGCCTGAWATTCWACCCC-3', SEQ ID NO:74), designed from the sequence obtained with primer 466215. Forward primer 20205 (5'-CCATGTGATTATCGACCATTCGGC-3', SEQ ID NO:75) was designed from sequence obtained with primer 20215. Primers 20205 and 20215 flank the coding sequence of the first coding exon and can be used to amplify this coding sequence using PCR.

EXAMPLE 6

This example illustrates the preparation of expression vectors containing neurturin cDNA.

For expression of recombinant neurturin in mammalian cells the neurturin vector pCMV-NTN-3-1 was constructed. The 585 nucleotide open reading frame of the neurturin cDNA was amplified by PCR using a primer containing the first 27 nucleotides of the neurturin coding sequence (5'-GCGACGCGTACCATGAGGCGCTGGAAGGCAGCGG-CCCTG, SEQ ID NO:63) and a primer containing the last 5 codons and the stop codon (5'-GACGGATCCGCATCACACGCACGCGCACTC) (SEQ ID NO:64) using reverse transcribed postnatal day 1 mouse brain mRNA as template using (PCR parameters: 94° C. for 30 sec; 60° C. for 15 sec; and 68° C. for 2 min for 35 cycles and including 5% DMSO in the reaction). The PCR product was subcloned into the Eco RV site of BSKS and sequenced to verify that it contained no PCR generated mutations. The neurturin coding sequence was then excised from this vector using Mlu I (5' end) and Bam H1 (3' end) and inserted downstream of the CMV IE promoter/enhancer in the mammalian expression vector pCB6 (Brewer, C. B. *Methods in Cell Biology* 43:233–245, 1994) to produce the pCMV-NTN-3-1 vector using these sites.

For expression of recombinant protein in *E. Coli*, the mature coding region of mouse neurturin was amplified by PCR using a primer containing the first 7 codons of the mature coding sequence (5'-GACCATATGCCGGGGGCTCGGCCTTGTGG) (SEQ ID NO:65) and a primer containing the last 5 codons and the stop codon 5'-GACGGATCCGCATCACACGCACGCGCACTC (SEQ ID NO:66) using a fragment containing the murine neurturin gene as template using (PCR parameters: 94° C. for 30 sec; 60° C. for 15 sec and 68° C. for 90 sec for 25 cycles with 5%=DMSO added into the reaction). The amplified product was subcloned into the Eco RV site of BSKS, the nucleotide sequence was verified, and this fragment was then transferred to the expression vector pET-30a (Novagen, Madison, Wis.) using an Nde 1 site (5' end) and an Eco R1 site (3' end). The pET-neurturin (pET-NTN) vector codes for an initiator methionine in front of the first amino acid of the mature mouse neurturin protein predicted from the N-terminal amino acid sequence of neurturin purified from the CHO cell conditioned media.

EXAMPLE 7

This example illustrates the transient transfection of NIH3T3 cells with the neurturin expression vector pCMV-NTN-3-1 and that the product of the genomic sequence in Example 5 is biologically active.

To demonstrate that the cloned neurturin cDNA was sufficient to direct the synthesis of biologically active neurturin we transiently introduced the pCMV-NTN-3-1 plasmid into NIH3T3 cells using the lipofectamine method of transfection. NIH3T3 cells were plated at a density of 400,000 cells per well (34.6 mm diameter) in 6 well plates (Corning, Corning, N.Y.) 24 hours before transfection. DNA liposome complexes were prepared and added to the cells according to the manufacturer's protocol using 1.5 µg CMV-neurturin plasmid DNA (isolated and purified using a Qiagen (Chatsworth, Calif.) tip-500 column according to manufacturer's protocol) and 10 µl lipofectamine reagent (Gibco BRL, Gaithersburg, Md.) in 1:1 DME/F12 medium containing 5 µg/ml insulin, 5 µg/ml transferrin, and 5 ng/ml sodium selenite (Sigma, St. Louis, Mo.). Five hours after the addition of DNA liposome complexes in 1 ml medium per well, 1 ml DME medium containing 20% calf serum was added to each well. Twenty-four hours after the addition of DNA-liposome complexes, the 2 ml medium above was replaced with 1 ml DME medium containing 10% calf serum, 2 mM glutamine, 100 U/ml penicillin, 100 µ/ml streptomycin, and 25 ug/ml heparin. The cells were incubated for an additional 24 hours before the conditioned medium was harvested, centrifuged to remove cellular debris, and frozen.

As a control, NIH3T3 cells were transfected as above using 1.5 µg CMV-neo expression plasmid (containing no cDNA insert) in place of the 1.5 µg CMV-neurturin plasmid. Conditioned medium from NIH3T3 cells transfected with either control plasmid or CMV-neurturin plasmid was assayed by direct addition to the SCG culture medium at the time of NGF deprivation. Addition of 0.25 ml conditioned medium from CMV-neurturin-transfected cells promoted 70% survival of sympathetic neurons, and >90% survival could be obtained with 0.45 ml of this conditioned medium. No significant survival promoting activity was detected in the conditioned medium of control transfected NIH3T3 cells.

EXAMPLE 8

This example illustrates the preparation of Chinese hamster ovary cells stably transformed with neurturin cDNA.

DG44 cells, a Chinese hamster ovary cell derivative that is deficient in dihydrofolate reductase (DHFR) (Urlaub et al

*Cell* 3:405–412, 1983 which is incorporated by reference), were stably co-transfected with expression plasmid (pCMV-NTN-3-1) and a DHFR expression plasmid (HLD) (McArthur, and Stanners *J. Biol. Chem.* 266:6000–6005, 1991 which is incorporated by reference).

On day 1 DG44 cells were plated at $1 \times 10^6$ cells per 10 cm plate in Ham's F12 medium with 10% fetal calf serum (FCS). This density must not be exceeded or cells will overgrow before selection media is added on day 5.

On day 2 cells were transfected with a 9:1 ratio of pCMV-NTN to DHFR expression plasmid using the calcium phosphate method (10 ug DNA/10 cm plate) (Chen and Okayama, *Mol Cell Biol* 7:2745–2752, 1987 which is incorporated by reference).

On day 3 the transfected cells were washed with Ham's F12 medium and fed Ham's F12 with 10% FCS.

On day 5 the cells were washed with MEM alpha medium and fed selection medium, which is MEM alpha with 10% FCS and 400 ug/ml G418. The cells were maintained in selection media, feeding every 4 days. Colonies began to appear approximately 14 days after transfection. Colonies growing in selection media were then transferred to a 24 well plate and trypsinized the next day to disperse the cells. The cells were grown to confluence in either 24 well or 6 well plates in order to screen the cells for expression of recombinant protein. Expression of neurturin was examined in 10 clonal lines and two high expressing lines were detected using the SCG survival assay. These clonal lines were expanded and expression in these selected cell lines was amplified by selection in 50 nM methotrexate (MTX). For selection in MTX, cells were grown to 50% confluence in a 150 cm$^2$ flask in selection medium. The medium was changed to MEM alpha containing 50 nM MTX concentration (it was not necessary to use G418 during MTX amplification). After placement in 50 nM MTX, the majority of cells died and colonies of resistant cells reappeared in 1–2 weeks. At this time, the cells were trypsinized to disperse colonies and are split when cells reach confluence. Cells eventually reached the same growth rate as before. The selected cells were screened for expression of recombinant protein. A 2–3 fold increase in expression was observed after selection in 50 nM MTX. Frozen stocks were kept for cell lines obtained from the original selection and the 50 nM MTX selection. Further selection could be continued in increasing MTX until desired levels of expression are obtained.

Using the above method, we isolated cells identified as DG44CHO5-3(G418)(pCMV-NTN-3-1) and DG44CHO5-3 (50 nM MTX)(pCMV-NTN-3-1). Cells from the DG44CHO5-3(50 nM MTX)(pCMV-NTN-3-1) strain expressed levels of approximately 100 µg of biologically active protein per liter of conditioned media determined by direct assay of conditioned medium in SCG assay according to the methods in example 1.

EXAMPLE 9

This example illustrates the expression of neurturin in various tissues.

A survey of neurturin and GDNF expression was performed in rat embryonic tissues (E10, day 10 after conception), neonatal tissues (P1, Postnatal Day 1), and adult tissues (>3 mos) using semi-quantitative RT/PCR (Estus et al., *J Cell Biol* 127:1717–1727, 1994 which is incorporated by reference). The RNA samples were obtained from various tissues and PCR products were detected either by autoradiography after incorporation of $\alpha$-$^{32}$P-dCTP in the PCR and electrophoresis on a polyacrylamide gel (FIG. 6) or by ethidium bromide staining of DNA after electrophoresis on agarose gels (Tables 3 and 4). The neurturin fragment of 101 base pairs was obtained using the forward primer CAGCGACGACGCGTGCGCAAAGAGCG (SEQ ID NO:67) and reverse primer TAGCGGCTGTGTACGTC-CAGGAAGGACACCTCGT (SEQ ID NO:68) and the GDNF fragment of 194 base pairs was obtained using the forward primer AAAAATCGGGGGTGYGTCTTA (SEQ ID NO:69) and the reverse primer CATGCCTGGCCTA-CYTTGTCA (SEQ ID NO:70).

No neurturin or GDNF mRNA was detected at the earliest embryonic age (embryonic day 10, E10) surveyed.

In neonates (postnatal day 1, P1) both transcripts were expressed in many tissues although neurturin tended to show a greater expression in most tissues than did GDNF. (see table 3).

TABLE 3

|  | NEURTURIN | GDNF |
|---|---|---|
| Liver | +++ | − |
| Blood | +++ | + |
| Thymus | + | − |
| Brain | ++ | + |
| Sciatic nerve | − | + |
| Kidney | ++ | ++ |
| Spleen | ++ | + |
| Cerebellum | ++ | + |
| Heart | ++ | + |
| Bone | + | + |

As shown in Table 3, differences in the tissue distributions of neurturin and GDNF were noted. In particular, no GDNF was detected in liver and thymus where neurturin expression was detected and no neurturin was detected in sciatic nerve where GDNF was detected.

Neurturin and GDNF mRNA were detected in many tissues in the adult animal, but the tissue-specific pattern of expression for these two genes was very different. (table 4, FIG. 5).

TABLE 4

|  | NEURTURIN | GDNF |
|---|---|---|
| Liver | − | − |
| Blood | + | − |
| Thymus | + | ++ |
| Brain | + | − |
| Sciatic nerve | − | − |
| Kidney | ++ | + |
| Spleen | − | + |
| Cerebellum | − | − |
| Uterus | ++ | − |
| Bone marrow | ++ | − |
| Testis | ++ | ++ |
| Ovary | + | + |
| Placenta | + | − |
| Skeletal muscle | + | − |
| Spinal cord | + | − |
| Adrenal gland | ++ | ++ |
| Gut | + | ++ |

As shown in table 4, neurturin was found to be expressed in brain and spinal cord as well as in blood and bone marrow where no GDNF was detected. The level of expression of neurturin in brain and blood was, however, less than that detected in neonatal tissue.

43

Neurturin was also highly expressed in freshly isolated rat peritoneal mast cells, whereas GDNF showed little or no expression.

EXAMPLE 10

This example illustrates the preparation of antisera to neurturin by immunization of rabbits with a neurturin peptide.

The peptide sequence corresponding to amino acids 73–87 of the mature murine neurturin protein was synthesized and coupled to keyhole limpet hemocyanin (KLH) as described earlier (Harlow and Lane, *Antibodies: a laboratory manual*, 1988. Cold Spring Harbor Laboratory, New York, N.Y. p. 72–81 which is incorporated by reference). The KLH-coupled peptide was submitted to Caltag, Inc. and each of two rabbits were immunized. Immunization was by subcutaneous injection at 7–10 sites. The first injection was with 150 μg KLH-coupled peptide which was resuspended in 0.5 ml saline and emulsified with 0.5 ml complete Freund's adjuvant. Boost injections were begun 4 weeks after the initial injection and were performed once every 7 days as above for a total of 5 injections except that 100 μg of KLH-coupled peptide and incomplete Freund's adjuvant were used. Serum samples were collected 1 week after the fifth boost.

A pooled volume of twenty ml of serum that had been collected from both rabbits one week after the 5th injection was purified. For purification, a peptide affinity column was prepared by coupling the above peptide to cyanogen bromide activated Sepharose 4B according to the manufacturers protocol (Pharmacia Biotech). The serum was diluted 10 fold in 10 mM Tris pH 7.5 buffer and mixed by gentle rocking for 16 hours at 4° C. with 0.5 ml of peptide agarose matrix containing 5 mg of coupled peptide. The matrix was placed into a column, washed with 5 ml of 10 mM Tris pH 7.5, 150 mM NaCl, washed with 5 ml of 10 mM Tris pH 7.5 buffer containing 0.4M NaCl and eluted with 5.5 ml of 100 mM glycine pH 2.5 buffer. One tenth volume of 1.0M Tris pH 8.0 buffer was added to the eluate immediately after elution to neutralize the pH. The glycine eluate was dialyzed overnight against 10 mM Tris pH 7.5, 150 mM NaCl.

The affinity-purified antibodies were used in a western blot to demonstrate specific recognition of recombinant neurturin protein. Ten ml of conditioned medium collected from DG44CHO5-3(G418)(pCMV-NTN-3-1) cells was purified over SP Sepharose as described in Example 1 and the proteins electrophoresed on a reducing SDS-PAGE gel in the tricine buffer system (Schagger and von Jagow *Analytical Biochemistry* 166:368–379, 1987). The proteins were electroblotted to a nitrocellulose membrane in 25 mM Tris, 192 mM glycine, 0.04% SDS, 17% methanol at 4° C. for 16 hr. The membrane was incubated with the affinity-purified anti-neurturin peptide antibodies and then with horseradish peroxidase-coupled sheep anti-rabbit IgG (Harlow and Lane, supra, p. 498–510). Bound antibodies were detected with enhanced chemiluminescence (ECL kit, Amersham, Buckinghamshire, England). The anti-neurturin antibodies recognized a single, approximately 11.5 kD protein band in the conditioned medium of the DG44CHO5-3(G418)(pCMV-NTN-3-1) cells. Using these anti-neurturin antibodies, neurturin protein could be detected in 10 ml of conditioned medium from DG44CHO5-3(G418)(pCMV-NTN-3-1) cells but could not be detected in 10 ml of medium conditioned with DG44 cells that had not been transformed with the neurturin expression vector.

EXAMPLE 11

The following example illustrates the identification of additional members of the GDNF/neurturin gene subfamily.

44

The TGF-β superfamily currently contains over 25 different gene members (for review see Kingsley, *Genes and Development* 8:133–146, 1994 which is incorporated by reference). The individual family members display varying degrees of homology with each other and several subgroups within the superfamily can be defined by phylogenetic analysis using the Clustal V program (Higgins et al, *Comput Appl Biosci* 8:189–191, 1992 which is incorporated by reference) and by bootstrap analysis of phylogenetic trees (Felsenstein, *Evolution* 39:783–791, 1985 which is incorporated by reference). Neurturin is approximately 40% identical to GDNF but less than 20% identical to any other member of the TGF-β superfamily. Several sequence regions in neurturin can be identified (FIG. 5) that are highly conserved within the GDNF/neurturin subfamily but not within the TGF-β superfamily. These conserved regions are likely to characterize a subfamily containing previously unisolated genes, which can now be isolated using the conserved sequence regions identified by the discovery and sequencing of the neurturin gene. Regions of high sequence conservation between neurturin and GDNF allow the design of degenerate oligonucleotides which can be used either as probes or primers. Conserved-region amino acid sequences have been identified herein to include Val-$Xaa_1$-$Xaa_2$-Leu-Gly-Leu-Gly-Tyr in which $Xaa_1$ is Ser or Thr and $Xaa_2$ is Glu or Asp (SEQ ID NO:33); Glu-$Xaa_1$-$Xaa_2$-$Xaa_3$-Phe-Arg-Tyr-Cys-$Xaa_4$-Gly-$Xaa_5$-Cys-$Xaa_6$-$Xaa_7$-Ala in which $Xaa_1$ is Thr or Glu, $Xaa_2$ is Val or Leu, $Xaa_3$ is Leu or Ile, $Xaa_4$ is Ala or Ser, $Xaa_5$ is Ala or Ser, $Xaa_6$ is Glu or Asp and $Xaa_7$ is Ala or Ser (SEQ ID NO:34); and Cys-Cys-Arg-Pro-$Xaa_1$-Ala-$Xaa_2$-$Xaa_3$-Asp-$Xaa_4$-$Xaa_5$-Ser-Phe-Leu-Asp in which $Xaa_1$ is Thr or Val or Ile, Xaa2 is Tyr or Phe, $Xaa_3$ is Glu or Asp, $Xaa_4$ is Glu or Asp and $Xaa_5$ is val or leu (SEQ ID NO:35). Nucleotide sequences containing a coding sequence for the above conserved sequences or fragments of the above conserved sequences can be used as probes. Exemplary probe and primer sequences which can be designed from these regions are Primer 1, GTNWSN-GANYTNGGNYTNGGNTA (SEQ ID NO:42) which encodes the amino acid sequence, Val-$Xaa_1$-$Xaa_2$-Leu-Gly-Leu-Gly-Tyr where $Xaa_1$ is Ser or Thr and $Xaa_2$ is Glu or Asp (SEQ ID NO:33); Primer 2, TTYMGNTAYTGYD-SNGGNDSNTGYGANKCNGC (SEQ ID NO:43) which encodes amino acid sequence Phe-Arg-Tyr-Cys-$Xaa_1$-Gly-$Xaa_2$-Cys-$Xaa_3$-$Xaa_4$-Ala where $Xaa_1$ is Ala or Ser, $Xaa_2$ is Ala or Ser, $Xaa_3$ is Glu or Asp and $Xaa_4$ is Ser or Ala (SEQ ID NO:36); Primer 3 reverse GCNGMNTCRCANSHNC-CNSHRTANCKRAA (SEQ ID NO:44) which encodes amino acid sequence Phe-Arg-Tyr-Cys-$Xaa_1$-Gly-$Xaa_2$-Cys-$Xaa_3$-$Xaa_4$-Ala where $Xaa_1$ is Ala or Ser, $Xaa_2$ is Ala or Ser, $Xaa_3$ is Glu or Asp and $Xaa_4$ is Ser or Ala (SEQ ID NO:37); Primer 4 reverse TCRTCNTCRWANGCN-RYNGGNCKCARCA (SEQ ID NO:45) which encodes amino acid sequence amino acid sequence Cys-Cys-Arg-Pro-$Xaa_1$-Ala-$Xaa_2$-$Xaa_3$-Asp-$Xaa_4$ where $Xaa_1$ is Ile or Thr or Val, $Xaa_2$ Try or Phe, $Xaa_3$ is Glu or Asp and $Xaa_4$ is Glu or Asp (SEQ ID NO:38); Primer 5 reverse TCNAR-RAANSWNAVNTCRTCNTCRWANGC (SEQ ID NO:46) which encodes amino acid sequence Ala-$Xaa_1$-$Xaa_2$-Asp-$Xaa_3$-$Xaa_4$-Ser-Phe-Leu-Asp where $Xaa_1$ is Tyr or Phe, $Xaa_2$ Glu or Asp, $Xaa_3$ is Glu or Asp, and $Xaa_4$ is Val or Leu (SEQ ID NO:39); Primer 6 GARRMNBTNHTNTTYMGN-TAYTG (SEQ ID NO:47) which encodes amino acid sequence Glu-$Xaa_1$-$Xaa_2$-$Xaa_3$-Phe-Arg-Tyr-Cys where $Xaa_1$ is Glu or Thr, $Xaa_2$ is Leu or Val and $Xaa_3$ is Ile or Leu (SEQ ID NO:40); Primer 7 GARRMNBTNHTNTTYMGN-TAYTGYDSNGGNDSNTGHGA (SEQ ID NO:48) which encodes amino acid sequence Glu-Xaa$_1$-Xaa$_2$-Xaa$_3$-Phe-Arg-Tyr-Cys-Xaa$_4$-Gly-Xaa$_5$-Cys-Xaa$_6$ where Xaa$_1$ is Glu or Thr, Xaa$_2$ is Leu or Val, Xaa$_3$ is Ile or Leu, Xaa$_4$ is Ser or Ala, Xaa$_5$ is Ser or Ala and Xaa$_6$ is Glu or Asp (SEQ ID NO:41).

The above sequences can be used as probes for screening libraries of genomic clones or as primerrs for amplifying gene fragments from genomic DNA or libraries of genomic clones or from reverse transcribed cDNA using RNA templates from a variety of tissues. Genomic DNA or libraries of genomic clones can be used as templates because the intron/exon structures of neurturin and GDNF are conserved and coding sequences of the mature proteins are not interrupted by introns.

A degenerate oligonucleotide can be synthesized as a mixture of oligonucleotides containing all of the possible nucleotide sequences which code for the conserved amino acid sequence. To reduce the number of different oligonucleotides in a degenerate mix, an inosine base can be incorporated in the synthesis at positions where all four nucleotides are possible. The inosine base forms base pairs with each of the four normal DNA bases which are less stabilizing than AT and GC base pairs but which are also less destabilizing than mismatches between the normal bases (i.e. AG, AC, TG, TC).

To isolate family members a primer above can be end labeled with $^{32}$P using T4 polynucleotide kinase and hybridized to libraries of human genomic clones according to standard procedures.

A preferred method for isolating family member genes would be to use various combinations of the degenerate primers above as primers in the polymerase chain reaction using genomic DNA as a template. As an example primer 2 (SEQ ID NO:43) can be used with primer 4 (SEQ ID NO:45) in PCR with 1 ug of human genomic DNA and cycling parameters of 94° C. for 30 sec, 50° C. for 30 sec, and 72° C. for 60 sec. These PCR conditions are exemplary only and one skilled in the art will readily appreciate that a range of suitable conditions could be used or optimized such as different temperatures and varying salt concentrations in the buffer medium and the like. It is preferred that DMSO be added to the PCR reaction to a final concentration of 5% inasmuch as this was found to be necessary for amplification of this region of the neurturin gene. The PCR reaction, when run on an agarose gel, should contain products in the size range of 125–150 base pairs since a one amino acid gap is introduced in the neurturin sequence when aligned with GDNF, and thus family member genes might also contain a slightly variable spacing between the conserved sequences of primers 2 and 4. The PCR products in the range of 125–150 base pairs should contain multiple amplified gene products including GDNF and neurturin as well as previously unisolated family members. To identify sequences of these products, they can be gel purified and ligated into the Bluescript plasmid (Stratagene), and then transformed into the XL1-blue E. Coli host strain (Stratagene). Bacterial colonies containing individual subclones can be picked for isolation and plated on nitrocellulose filters in two replicas. Each of the replicate filters can be screened with an oligonucleotide probe for either unique GDNF or unique neurturin sequence in the amplified region. Subclones not hybridizing to either GDNF or neurturin can be sequenced and if found to encode previously unisolated family members, the sequence can be used to isolate full length cDNA clones and genomic clones as was done for neurturin (Example 5). A similar method was used to isolate new gene members (GDF-3 and GDF-9) of the TGF-β superfamily based on homology between previously identified genes (McPherron *J Biol Chem* 268:3444–3449, 1993 which is incorporated by reference).

The inventors herein believe that the most preferred way to isolate family member genes may be to apply the above PCR procedure as a screening method to isolate individual family member genomic clones from a library. This is because there is only one exon for the coding region of both mature neurturin and GDNF. If, for example, the above PCR reaction with primers 2 and 4 generates products of the appropriate size using human genomic DNA as template, the same reaction can be performed using, as template, pools of genomic clones in the P1 vector according to methods well known in the art, for example that used for isolating neurturin human genomic clones (Example 5). Pools containing the neurturin gene in this library have previously been identified and GDNF containing pools can be readily identified by screening with GDNF specific primers. Thus non-neurturin, non-GDNF pools which generate a product of the correct size using the degenerate primers will be readily recognized as previously unisolated family members. The PCR products generated from these pools can be sequenced directly using the automated sequencer and genomic clones can be isolated by further subdivision and screening of the pooled clones as a standard service offered by Genome Systems, Inc.

Deposit of Strain. the following strain is on deposit under the terms of the Budapest Treaty, with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit, or for the enforceable life of the U.S. patent, whichever is longer. Should a culture become nonviable or be inadvertently destroyed, or, in the case of plasmid-containing strains, lose its plasmid, it will be replaced with a viable culture. The deposited materials mentioned herein are intended for convenience only, and are not required to practice the present invention in view of the description herein, and in addition, these materials are incorporated herein by reference.

| Strain | Deposit Date | ATCC No. |
| --- | --- | --- |
| DG44CHO-pHSP-NGFI-B | August 25, 1995 | ATCC Deposit Number CRL 11977 |

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. An isolated and purified polynucleotide or a polynucleotide complementary thereto wherein said polynucleotide comprises a nucleotide sequence encoding a neurturin polypeptide that promotes survival in superior cervical ganglion cells or nodose ganglion cells and wherein said polynucleotide complementary thereto hybridizes under high stringency conditions to a SEQ ID NO:9 or SEQ ID NO:10.

2. The isolated and purified polynucleotide or polynucleotide complementary thereto according to claim 1 wherein the neurturin polypeptide comprises a human neurturin polypeptide as set forth in SEQ ID NO:1.

3. The isolated and purified polynucleotide or polynucleotide complementary thereto according to claim 2 comprising SEQ ID NO:9.

4. The isolated and purified polynucleotide or polynucleotide complementary thereto according to claim 1 wherein the neurturin polypeptide comprises a murine amino acid sequence as set forth in SEQ ID NO:2.

5. The isolated and purified polynucleotide or polynucleotide complementary thereto according to claim 4 comprising SEQ ID NO:10.

6. A vector comprising expression regulatory elements operably linked to a polynucleotide as defined in claim 1.

7. The vector of claim 6 wherein said vector is pCMV-NTN-3-1 or pET-NTN.

8. A host cell transformed with the vector of claim 7.

9. The host cell of claim 8 wherein said host cell is a mammalian cell.

10. The host cell of claim 9 wherein the host cell is a bacterial cell.

11. The host cell of claim 8 wherein said host cell is a baculovirus expression system.

12. An isolated and purified fragment of a nucleotide sequence or a sequence complementary to said fragment, wherein said fragment consists of at least 20 contiguous nucleotides, wherein said nucleotide sequence encodes a neurturin polypeptide that promotes survival in superior cervical ganglion cells or nodose ganglion cells, and wherein said sequence complementary to said fragment hybridizes under high stringency conditions to SEQ ID NO:9 or SEQ ID NO:10.

13. The isolated and purified fragment according to claim 12 wherein said neurturin polypeptide sequence is a human polypeptide sequence as set forth in SEQ ID NO:1.

14. The isolated and purified fragment according to claim 12 wherein said neurturin polypeptide sequence is a murine polypeptide sequence as set forth in SEQ ID NO:2.

15. An isolated and purified nucleic acid comprising a nucleotide sequence encoding a conservatively substituted variant of SEQ ID NO:1 or SEQ ID NO:2 wherein said variant promotes survival in superior cervical ganglion cells or nodose ganglion cells.

16. An isolated and purified polynucleotide consisting of at least 20 contiguous nucleotides or a polynucleotide complementary thereto wherein said polynucleotide complementary thereto hybridizes under high stringency conditions to SEQ ID NO:9 or SEQ ID NO:10.

17. The isolated and purified polynucleotide or polynucleotide complementary thereto according to claim 16 wherein said polynucleotide complementary thereto hybridizes under high stringency conditions to an mRNA or a genomic DNA, and wherein said mRNA or genomic DNA encodes a human or mouse neurturin amino acid sequence which promotes survival in superior cervical ganglion cells or nodose ganglion cells.

18. An isolated and purified polynucleotide or a polynucleotide complementary thereto wherein said polynucleotide comprises a nucleotide sequence encoding a neurturin polypeptide that promotes survival in superior cervical ganglion cells or nodose ganglion cells and wherein said polynucleotide complementary thereto hybridizes under high stringency conditions to a pre-pro neurturin as set forth in SEQ ID NO:11 or SEQ ID NO:12.

19. The isolated and purified polynucleotide or polynucleotide complementary thereto according to claim 18 wherein the nucleotide sequence encodes a human pre-pro neurturin amine acid sequence is as set forth in SEQ ID NO:7 or a murine pre-pro neurturin amine acid sequence as set forth in SEQ ID NO:8.

20. The isolated and purified polynucleotide or polynucleotide complementary thereto according to claim 19 comprising SEQ ID NO:11 or SEQ ID NO:12.

21. A vector comprising expression regulatory elements operably linked to a polynucleotide as defined in claim 18.

22. A host cell transformed with the vector of claim 21.

23. The host cell of claim 21 wherein said host cell is a mammalian cell, a bacterial cell or a baculovirus expression system.

24. An isolated and purified fragment of a nucleotide sequence or a sequence complementary to said fragment, wherein said fragment consists of at least 20 contiguous nucleotides, wherein said nucleotide encode a pre-pro neurturin as set forth in SEQ ID NO:7 or SEQ ID NO:8 and wherein said sequence complementary to said fragment hybridizes under high stringency conditions to SEQ ID NO:11 or SEQ ID NO:12.

25. The isolated and purified polynucleotide of claim 24 comprising a fragment of SEQ ID NO:11 or SEQ ID NO:12.

26. An isolated and purified nucleic acid comprising a nucleotide sequence encoding a conservatively substituted variant of SEQ ID NO:7 or SEQ ID NO:8.

27. An isolated and purified polynucleotide of at least 20 contiguous nucleotides wherein said polynucleotide complementary thereto hybridizes under high stringency conditions to SEQ ID NO:11 or SEQ ID NO:12.

28. The isolated and purified polynucleotide or polynucleotide complementary thereto according to claim 27 wherein said polynucleotide complementary thereto hybridizes under high stringency conditions to an mRNA or a genomic DNA, and wherein said mRNA or genomic DNA encodes a human pre-pro neurturin amino acid sequence as set forth in SEQ ID NO:7 or a murine pre-pro neurturin amino acid sequence as set forth in SEQ ID NO:8.

29. An isolated and purified polynucleotide comprising a nucleotide sequence encoding a neurturin pre- region of SEQ ID NO:15, SEQ ID NO:16.

30. The isolated and purified polynucleotide of claim 29 comprising SEQ ID NO:17 or SEQ ID NO:18.

31. An isolated and purified polynucleotide comprising a nucleotide sequence encoding a neurturin pro- region of SEQ ID NO:19, SEQ ID NO:22.

32. The isolated and purified polynucleotide of claim 31 comprising SEQ ID NO:20 or SEQ ID NO:21.

33. An isolated and purified polynucleotide comprising a nucleotide sequence encoding a neurturin pre-pro region of SEQ ID NO:23, SEQ ID NO:24.

34. The isolated and purified polynucleotide of claim 33 comprising SEQ ID NO:25 or SEQ ID NO:26.

35. A kit for detecting the presence of mRNA encoding neurturin in a sample from a patient said kit comprising a polynucleotide as defined in claim 16, packaged in a container.

36. The kit according to claim 35 wherein the polynucleotide encodes SEQ ID NO:1 or SEQ ID NO:2.

37. The kit according to claim 36 wherein the polynucleotide comprises SEQ ID NO:9 or SEQ ID NO:10.

* * * * *

SEQUENCE LISTING ( 1 ) GENERAL INFORMATION:

( i i i ) NUMBER OF SEQUENCES: 78

( 2 ) INFORMATION FOR SEQ ID NO:1:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ala  Arg  Leu  Gly  Ala  Arg  Pro  Cys  Gly  Leu  Arg  Glu  Leu  Glu  Val  Arg
 1                  5                        10                       15

Val  Ser  Glu  Leu  Gly  Leu  Gly  Tyr  Ala  Ser  Asp  Glu  Thr  Val  Leu  Phe
              20                        25                       30

Arg  Tyr  Cys  Ala  Gly  Ala  Cys  Glu  Ala  Ala  Ala  Arg  Val  Tyr  Asp  Leu
         35                        40                       45

Gly  Leu  Arg  Arg  Leu  Arg  Gln  Arg  Arg  Arg  Leu  Arg  Arg  Glu  Arg  Val
 50                            55                       60

Arg  Ala  Gln  Pro  Cys  Cys  Arg  Pro  Thr  Ala  Tyr  Glu  Asp  Glu  Val  Ser
 65                  70                        75                       80

Phe  Leu  Asp  Ala  His  Ser  Arg  Tyr  His  Thr  Val  His  Glu  Leu  Ser  Ala
              85                        90                       95

Arg  Glu  Cys  Ala  Cys  Val
              100
```

( 2 ) INFORMATION FOR SEQ ID NO:2:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro  Gly  Ala  Arg  Pro  Cys  Gly  Leu  Arg  Glu  Leu  Glu  Val  Arg  Val  Ser
 1                  5                        10                       15

Glu  Leu  Gly  Leu  Gly  Tyr  Thr  Ser  Asp  Glu  Thr  Val  Leu  Phe  Arg  Tyr
              20                        25                       30

Cys  Ala  Gly  Ala  Cys  Glu  Ala  Ala  Ile  Arg  Ile  Tyr  Asp  Leu  Gly  Leu
         35                        40                       45

Arg  Arg  Leu  Arg  Gln  Arg  Arg  Arg  Val  Arg  Arg  Glu  Arg  Ala  Arg  Ala
 50                            55                       60

His  Pro  Cys  Cys  Arg  Pro  Thr  Ala  Tyr  Glu  Asp  Glu  Val  Ser  Phe  Leu
 65                  70                        75                       80

Asp  Val  His  Ser  Arg  Tyr  His  Thr  Leu  Gln  Glu  Leu  Ser  Ala  Arg  Glu
              85                        90                       95

Cys  Ala  Cys  Val
              100
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear (  i i ) MOLECULE TYPE: peptide (  i x ) FEATURE:
      ( A ) NAME/KEY: Modified-site
      ( B ) LOCATION: 6
      ( D ) OTHER INFORMATION: /note= "ANY AMINO ACID"

(  x i ) SEQUENCE DESCRIPTION: SEQ ID NO:3:

Ser Gly Ala Arg Pro Xaa Gly Leu Arg Glu Leu Glu Val Ser Val Ser
1                   5                   10                  15

( 2 ) INFORMATION FOR SEQ ID NO:4:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "ANY AMINO ACID"

( i x ) FEATURE:
      ( A ) NAME/KEY: Modified-site
      ( B ) LOCATION: 6
      ( D ) OTHER INFORMATION: /note= "SERINE OR CYSTEINE"

(  x i ) SEQUENCE DESCRIPTION: SEQ ID NO:4:

Xaa Cys Ala Gly Ala Xaa Glu Ala Ala Val
1                   5                   10

( 2 ) INFORMATION FOR SEQ ID NO:5:

( i ) SEQUENCE CHARACTERISTICS:
      ( A ) LENGTH: 23 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "ANY AMINO ACID"

( i x ) FEATURE:
      ( A ) NAME/KEY: Modified-site
      ( B ) LOCATION: 2
      ( D ) OTHER INFORMATION: /note= "ANY AMINO ACID"

( i x ) FEATURE:
      ( A ) NAME/KEY: Modified-site
      ( B ) LOCATION: 17
      ( D ) OTHER INFORMATION: /note= "GLUTAMINE OR GLUTAMIC ACID"

(  x i ) SEQUENCE DESCRIPTION: SEQ ID NO:5:

Xaa Xaa Val Glu Ala Lys Pro Cys Cys Gly Pro Thr Ala Tyr Glu Asp
1                   5                   10                  15

Xaa Val Ser Phe Leu Ser Val
                20

( 2 ) INFORMATION FOR SEQ ID NO:6:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

Tyr His Thr Leu Gln Glu Leu Ser Ala Arg
1               5                   10

( 2 ) INFORMATION FOR SEQ ID NO:7:

( i ) SEQUENCE CHARACTERISTICS:
    ( A ) LENGTH: 197 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

Met Gln Arg Trp Lys Ala Ala Ala Leu Ala Ser Val Leu Cys Ser Ser
1               5                   10                  15

Val Leu Ser Ile Trp Met Cys Arg Glu Gly Leu Leu Leu Ser His Arg
                20                  25                  30

Leu Gly Pro Ala Leu Val Pro Leu His Arg Leu Pro Arg Thr Leu Asp
            35                  40                  45

Ala Arg Ile Ala Arg Leu Ala Gln Tyr Arg Ala Leu Leu Gln Gly Ala
        50                  55                  60

Pro Asp Ala Met Glu Leu Arg Glu Leu Thr Pro Trp Ala Gly Arg Pro
65                  70                  75                  80

Pro Gly Pro Arg Arg Arg Ala Gly Pro Arg Arg Arg Arg Ala Arg Ala
                85                  90                  95

Arg Leu Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg
            115                 120                 125

Tyr Cys Ala Gly Ala Cys Glu Ala Ala Ala Arg Val Tyr Asp Leu Gly
    130                 135                 140

Leu Arg Arg Leu Arg Gln Arg Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
            180                 185                 190

Glu Cys Ala Cys Val
            195

( 2 ) INFORMATION FOR SEQ ID NO:8:

( i ) SEQUENCE CHARACTERISTICS:
    ( A ) LENGTH: 195 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

Met Arg Arg Trp Lys Ala Ala Ala Leu Val Ser Leu Ile Cys Ser Ser
1               5                   10                  15

Leu Leu Ser Val Trp Met Cys Gln Glu Gly Leu Leu Leu Gly His Arg
                20                  25                  30

Leu Gly Pro Ala Leu Ala Pro Leu Arg Arg Pro Pro Arg Thr Leu Asp
            35                  40                  45

Ala Arg Ile Ala Arg Leu Ala Gln Tyr Arg Ala Leu Leu Gln Gly Ala
        50                  55                  60

| Pro<br>65 | Asp | Ala | Val | Glu<br>70 | Leu | Arg | Glu | Leu | Ser<br>75 | Pro | Trp | Ala | Ala | Arg<br> | Ile<br>80 |
|---|---|---|---|---|---|---|---|---|---|---|---|---|---|---|---|
| Pro | Gly | Pro | Arg | Arg<br>85 | Arg | Ala | Gly | Pro | Arg<br>90 | Arg | Arg | Arg | Ala | Arg<br>95 | Pro |
| Gly | Ala | Arg | Pro<br>100 | Cys | Gly | Leu | Arg | Leu<br>105 | Glu | Val | Arg | Val<br>110 | Ser | Glu |
| Leu | Gly | Leu<br>115 | Gly | Tyr | Thr | Ser | Asp<br>120 | Glu | Thr | Val | Leu | Phe<br>125 | Arg | Tyr | Cys |
| Ala | Gly | Ala<br>130 | Cys | Glu | Ala | Ala<br>135 | Ile | Arg | Ile | Tyr | Asp<br>140 | Leu | Gly | Leu | Arg |
| Arg<br>145 | Leu | Arg | Gln | Arg<br>150 | Arg | Arg | Val | Arg | Arg<br>155 | Glu | Arg | Ala | Arg | Ala<br> | His<br>160 |
| Pro | Cys | Cys | Arg | Pro<br>165 | Thr | Ala | Tyr | Glu | Asp<br>170 | Glu | Val | Ser | Phe | Leu<br>175 | Asp |
| Val | His | Ser | Arg<br>180 | Tyr | His | Thr | Leu | Gln<br>185 | Glu | Leu | Ser | Ala | Arg<br>190 | Glu | Cys |
| Ala | Cys | Val<br>195 | | | | | | | | | | | | | |

( 2 ) INFORMATION FOR SEQ ID NO:9:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
GCGCGGTTGG GGGCGCGGCC TTGCGGGCTG CGCGAGCTGG AGGTGCGCGT GAGCGAGCTG      60
GGCCTGGGCT ACGCGTCCGA CGAGACGGTG CTGTTCCGCT ACTGCGCAGG CGCCTGCGAG     120
GCTGCCGCGC GCGTCTACGA CCTCGGGCTG CGACGACTGC GCCAGCGGCG CGCCTGCGG      180
CGGGAGCGGG TGCGCGCGCA GCCCTGCTGC CGCCCGACGG CCTACGAGGA CGAGGTGTCC     240
TTCCTGGACG CGCACAGCCG CTACCACACG GTGCACGAGC TGTCGGCGCG CGAGTGCGCC     300
TGCGTG                                                                306
```

( 2 ) INFORMATION FOR SEQ ID NO:10:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
CCGGGGGCTC GGCCTTGTGG GCTGCGCGAG CTCGAGGTGC GCGTGAGCGA GCTGGGCCTG      60
GGCTACACGT CGGATGAGAC CGTGCTGTTC CGCTACTGCG CAGGCGCGTG CGAGGCGGCC     120
ATCCGCATCT ACGACCTGGG CCTTCGGCGC CTGCGCCAGC GGAGGCGCGT GCGCAGAGAG     180
CGGGCGCGGG CGCACCCGTG TTGTCGCCCG ACGGCCTATG AGGACGAGGT GTCCTTCCTG     240
GACGTGCACA GCCGCTACCA CACGCTGCAA GAGCTGTCGG CGCGGAGTG CGCGTGCGTG     300
```

( 2 ) INFORMATION FOR SEQ ID NO:11:

( i ) SEQUENCE CHARACTERISTICS:

(A) LENGTH: 591 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

| | | | | | | |
|---|---|---|---|---|---|---|
| ATGCAGCGCT | GGAAGGCGGC | GGCCTTGGCC | TCAGTGCTCT | GCAGCTCCGT | GCTGTCCATC | 60 |
| TGGATGTGTC | GAGAGGGCCT | GCTTCTCAGC | CACCGCCTCG | GACCTGCGCT | GGTCCCCCTG | 120 |
| CACCGCCTGC | CTCGAACCCT | GGACGCCCGG | ATTGCCCGCC | TGGCCCAGTA | CCGTGCACTC | 180 |
| CTGCAGGGGG | CCCCGGATGC | GATGGAGCTG | CGCGAGCTGA | CGCCCTGGGC | TGGGCGGCCC | 240 |
| CCAGGTCCGC | GCCGTCGGGC | GGGGCCCCGG | CGGCGGCGCG | CGCGTGCGCG | GTTGGGGGCG | 300 |
| CGGCCTTGCG | GGCTGCGCGA | GCTGGAGGTG | CGCGTGAGCG | AGCTGGGCCT | GGGCTACGCG | 360 |
| TCCGACGAGA | CGGTGCTGTT | CCGCTACTGC | GCAGGCGCCT | GCGAGGCTGC | CGCGCGCGTC | 420 |
| TACGACCTCG | GGCTGCGACG | ACTGCGCCAG | CGGCGGCGCC | TGCGGCGGGA | GCGGGTGCGC | 480 |
| GCGCAGCCCT | GCTGCCGCCC | GACGGCCTAC | GAGGACGAGG | TGTCCTTCCT | GGACGCGCAC | 540 |
| AGCCGCTACC | ACACGGTGCA | CGAGCTGTCG | GCGCGCGAGT | GCGCCTGCGT | G | 591 |

(2) INFORMATION FOR SEQ ID NO:12:

(i) SEQUENCE CHARACTERISTICS:
(A) LENGTH: 585 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

| | | | | | | |
|---|---|---|---|---|---|---|
| ATGAGGCGCT | GGAAGGCAGC | GGCCCTGGTG | TCGCTCATCT | GCAGCTCCCT | GCTATCTGTC | 60 |
| TGGATGTGCC | AGGAGGGTCT | GCTCTTGGGC | CACCGCCTGG | ACCCGCGCT | TGCCCCGCTA | 120 |
| CGACGCCCTC | CACGCACCCT | GGACGCCCGC | ATCGCCGCC | TGGCCCAGTA | TCGCGCTCTG | 180 |
| CTCCAGGGCG | CCCCCGACGC | GGTGGAGCTT | CGAGAACTTT | CTCCCTGGGC | TGCCCGCATC | 240 |
| CCGGGACCGC | GCCGTCGAGC | GGGTCCCCGG | CGTCGGCGGG | CGCGGCCGGG | GGCTCGGCCT | 300 |
| TGTGGGCTGC | GCGAGCTCGA | GGTGCGCGTG | AGCGAGCTGG | GCCTGGGCTA | CACGTCGGAT | 360 |
| GAGACCGTGC | TGTTCCGCTA | CTGCGCAGGC | GCGTGCGAGG | CGGCCATCCG | CATCTACGAC | 420 |
| CTGGGCCTTC | GGCGCCTGCG | CCAGCGGAGG | CGCGTGCGCA | GAGAGCGGGC | GCGGGCGCAC | 480 |
| CCGTGTTGTC | GCCCGACGGC | CTATGAGGAC | GAGGTGTCCT | TCCTGGACGT | GCACAGCCGC | 540 |
| TACCACACGC | TGCAAGAGCT | GTCGGCGCGG | GAGTGCGCGT | GCGTG | | 585 |

(2) INFORMATION FOR SEQ ID NO:13:

(i) SEQUENCE CHARACTERISTICS:
(A) LENGTH: 348 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

| | | | | | | |
|---|---|---|---|---|---|---|
| GGAGGGAGAG | CGCGCGGTGG | TTTCGTCCGT | GTGCCCCGCG | CCCGGCGCTC | CTCGCGTGGC | 60 |
| CCCGCGTCCT | GAGCGCGCTC | CAGCCTCCCA | CGCGCGCCAC | CCCGGGGTTC | ACTGAGCCCG | 120 |
| GCGAGCCCGG | GGAAGACAGA | GAAAGAGAGG | CCAGGGGGGG | AACCCCATGG | CCCGGCCCGT | 180 |

```
GTCCCGCACC CTGTGCGGTG GCCTCCTCCG GCACGGGGTC CCCGGGTCGC CTCCGGTCCC        240

CGCGATCCGG ATGGCGCACG CAGTGGCTGG GGCCGGGCCG GGCTCGGGTG GTCGGAGGAG        300

TCACCACTGA CCGGGTCATC TGGAGCCCGT GGCAGGCCGA GGCCCAGG                    348
```

( 2 ) INFORMATION FOR SEQ ID NO:14:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
TGCTACCTCA CGCCCCCGA CCTGCGAAAG GGCCCTCCCT GCCGACCCTC GCTGAGAACT         60

GACTTCACAT AAAGTGTGGG AACTCCC                                           87
```

( 2 ) INFORMATION FOR SEQ ID NO:15:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Met Gln Arg Trp Lys Ala Ala Ala Leu Ala Ser Val Leu Cys Ser Ser
1               5                   10                  15

Val Leu Ser
```

( 2 ) INFORMATION FOR SEQ ID NO:16:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Met Arg Arg Trp Lys Ala Ala Ala Leu Val Ser Leu Ile Cys Ser Ser
1               5                   10                  15

Leu Leu Ser
```

( 2 ) INFORMATION FOR SEQ ID NO:17:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
ATGCAGCGCT GGAAGGCGGC GGCCTTGGCC TCAGTGCTCT GCAGCTCCGT GCTGTCC          57
```

( 2 ) INFORMATION FOR SEQ ID NO:18:

( i ) SEQUENCE CHARACTERISTICS:
        ( A ) LENGTH: 57 base pairs
        ( B ) TYPE: nucleic acid
        ( C ) STRANDEDNESS: single (D) TOPOLOGY: linear (ii) MOLECULE TYPE: cDNA (xi) SEQUENCE DESCRIPTION: SEQ ID NO:18:

| ATGAGGCGCT | GGAAGGCAGC | GGCCCTGGTG | TCGCTCATCT | GCAGCTCCCT | GCTATCT | 57 |

(2) INFORMATION FOR SEQ ID NO:19:

(i) SEQUENCE CHARACTERISTICS:
        (A) LENGTH: 76 amino acids
        (B) TYPE: amino acid
        (D) TOPOLOGY: linear (ii) MOLECULE TYPE: peptide (xi) SEQUENCE DESCRIPTION: SEQ ID NO:19:

```
Ile Trp Met Cys Arg Glu Gly Leu Leu Leu Ser His Arg Leu Gly Pro
 1               5                  10                  15
Ala Leu Val Pro Leu His Arg Leu Pro Arg Thr Leu Asp Ala Arg Ile
             20                  25                  30
Ala Arg Leu Ala Gln Tyr Arg Ala Leu Leu Gln Gly Ala Pro Asp Ala
         35                  40                  45
Met Glu Leu Arg Glu Leu Thr Pro Trp Ala Gly Arg Pro Pro Gly Pro
     50                  55                  60
Arg Arg Arg Ala Gly Pro Arg Arg Arg Ala Arg
 65                 70                  75
```

(2) INFORMATION FOR SEQ ID NO:20:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

| ATCTGGATGT | GTCGAGAGGG | CCTGCTTCTC | AGCCACCGCC | TCGGACCTGC | GCTGGTCCCC | 60 |
| CTGCACCGCC | TGCCTCGAAC | CCTGGACGCC | CGGATTGCCC | GCCTGGCCCA | GTACCGTGCA | 120 |
| CTCCTGCAGG | GGGCCCCGGA | TGCGATGGAG | CTGCGCGAGC | TGACGCCCTG | GCTGGGCGG | 180 |
| CCCCCAGGTC | CGCGCCGTCG | GGCGGGGCCC | CGGCGGCGGC | GCGCGCGT | | 228 |

(2) INFORMATION FOR SEQ ID NO:21:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

| GTCTGGATGT | GCCAGGAGGG | TCTGCTCTTG | GGCCACCGCC | TGGACCCGC | GCTTGCCCCG | 60 |
| CTACGACGCC | CTCCACGCAC | CCTGGACGCC | CGCATCGCCC | GCCTGGCCCA | GTATCGCGCT | 120 |
| CTGCTCCAGG | GCGCCCCCGA | CGCGGTGGAG | CTTCGAGAAC | TTTCTCCCTG | GCTGCCCGC | 180 |
| ATCCCGGGAC | CGCGCCGTCG | AGCGGGTCCC | CGGCGTCGGC | GGGCGCGG | | 228 |

(2) INFORMATION FOR SEQ ID NO:22:

( i ) SEQUENCE CHARACTERISTICS:
    ( A ) LENGTH: 76 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:22:

```
Val Trp Met Cys Gln Glu Gly Leu Leu Leu Gly His Arg Leu Gly Pro
1               5                   10                  15
Ala Leu Ala Pro Leu Arg Arg Pro Pro Arg Thr Leu Asp Ala Arg Ile
            20                  25                  30
Ala Arg Leu Ala Gln Tyr Arg Ala Leu Leu Gln Gly Ala Pro Asp Ala
        35                  40                  45
Val Glu Leu Arg Glu Leu Ser Pro Trp Ala Ala Arg Ile Pro Gly Pro
    50                  55                  60
Arg Arg Arg Ala Gly Pro Arg Arg Arg Ala Arg
65              70                  75
```

( 2 ) INFORMATION FOR SEQ ID NO:23:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
Met Gln Arg Trp Lys Ala Ala Ala Leu Ala Ser Val Leu Cys Ser Ser
1               5                   10                  15
Val Leu Ser Ile Trp Met Cys Arg Glu Gly Leu Leu Leu Ser His Arg
            20                  25                  30
Leu Gly Pro Ala Leu Val Pro Leu His Arg Leu Pro Arg Thr Leu Asp
        35                  40                  45
Ala Arg Ile Ala Arg Leu Ala Gln Tyr Arg Ala Leu Leu Gln Gly Ala
    50                  55                  60
Pro Asp Ala Met Glu Leu Arg Glu Leu Thr Pro Trp Ala Gly Arg Pro
65              70                  75                  80
Pro Gly Pro Arg Arg Arg Ala Gly Pro Arg Arg Arg Ala Arg
                85                  90                  95
```

( 2 ) INFORMATION FOR SEQ ID NO:24:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
Met Arg Arg Trp Lys Ala Ala Ala Leu Val Ser Leu Ile Cys Ser Ser
1               5                   10                  15
Leu Leu Ser Val Trp Met Cys Gln Glu Gly Leu Leu Leu Gly His Arg
            20                  25                  30
Leu Gly Pro Ala Leu Ala Pro Leu Arg Arg Pro Pro Arg Thr Leu Asp
        35                  40                  45
Ala Arg Ile Ala Arg Leu Ala Gln Tyr Arg Ala Leu Leu Gln Gly Ala
    50                  55                  60
Pro Asp Ala Val Glu Leu Arg Glu Leu Ser Pro Trp Ala Ala Arg Ile
65              70                  75                  80
```

| Pro | Gly | Pro | Arg | Arg | Arg | Ala | Gly | Pro | Arg | Arg | Arg | Ala | Arg |
|-----|-----|-----|-----|-----|-----|-----|-----|-----|-----|-----|-----|-----|-----|
|     |     |     |     | 85  |     |     |     |     | 90  |     |     |     | 95  |

( 2 ) INFORMATION FOR SEQ ID NO:25:

( i ) SEQUENCE CHARACTERISTICS:
    ( A ) LENGTH: 285 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:25:

```
ATGCAGCGCT GGAAGGCGGC GGCCTTGGCC TCAGTGCTCT GCAGCTCCGT GCTGTCCATC      60
TGGATGTGTC GAGAGGGCCT GCTTCTCAGC CACCGCCTCG GACCTGCGCT GGTCCCCCTG     120
CACCGCCTGC CTCGAACCCT GGACGCCCGG ATTGCCCGCC TGGCCCAGTA CCGTGCACTC     180
CTGCAGGGGG CCCCGGATGC GATGGAGCTG CGCGAGCTGA CGCCCTGGGC TGGGCGGCCC     240
CCAGGTCCGC GCCGTCGGGC GGGGCCCCGG CGGCGGCGCG CGCGT                     285
```

( 2 ) INFORMATION FOR SEQ ID NO:26:

( i ) SEQUENCE CHARACTERISTICS:
    ( A ) LENGTH: 285 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:26:

```
ATGAGGCGCT GGAAGGCAGC GGCCCTGGTG TCGCTCATCT GCAGCTCCCT GCTATCTGTC      60
TGGATGTGCC AGGAGGGTCT GCTCTTGGGC CACCGCCTGG ACCCGCGCT TGCCCCGCTA     120
CGACGCCCTC CACGCACCCT GGACGCCCGC ATCGCCCGCC TGGCCCAGTA TCGCGCTCTG     180
CTCCAGGGCG CCCCCGACGC GGTGGAGCTT CGAGAACTTT CTCCCTGGGC TGCCCGCATC     240
CCGGGACCGC GCCGTCGAGC GGGTCCCCGG CGTCGGCGGG CGCGG                     285
```

( 2 ) INFORMATION FOR SEQ ID NO:27:

( i ) SEQUENCE CHARACTERISTICS:
    ( A ) LENGTH: 169 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:27:

```
ATGCAGCGCT GGAAGGCGGC GGCCTTGGCC TCAGTGCTCT GCAGCTCCGT GCTGTCCATC      60
TGGATGTGTC GAGAGGGCCT GCTTCTCAGC CACCGCCTCG GACCTGCGCT GGTCCCCCTG     120
CACCGCCTGC CTCGAACCCT GGACGCCCGG ATTGCCCGCC TGGCCCAGT                 169
```

( 2 ) INFORMATION FOR SEQ ID NO:28:

( i ) SEQUENCE CHARACTERISTICS:
    ( A ) LENGTH: 425 base pairs
    ( B ) TYPE: nucleic acid
    ( C ) STRANDEDNESS: single
    ( D ) TOPOLOGY: linear ( i i ) MOLECULE TYPE: cDNA 5,739,307

65                                                                 66

-continued ( x i ) SEQUENCE DESCRIPTION: SEQ ID NO:28:

```
ACCGTGCACT  CCTGCAGGGG  GCCCCGGATG  CGATGGAGCT  GCGCGAGCTG  ACGCCCTGGG        60
CTGGGCGGCC  CCCAGGTCCG  CGCCGTCGGG  CGGGGCCCCG  GCGGCGGCGC  GCGCGTGCGC       120
GGTTGGGGGC  GCGGCCTTGC  GGGCTGCGCG  AGCTGGAGGT  GCGCGTGAGC  GAGCTGGGCC       180
TGGGCTACGC  GTCCGACGAG  ACGGTGCTGT  TCCGCTACTG  CGCAGGCGCC  TGCGAGGCTG       240
CCGCGCGCGT  CTACGACCTC  GGGCTGCGAC  GACTGCGCCA  GCGGCGGCGC  CTGCGGCGGG       300
AGCGGGTGCG  CGCGCAGCCC  TGCTGCCGCC  CGACGGCCTA  CGAGGACGAG  GTGTCCTTCC       360
TGGACGCGCA  CAGCCGCTAC  CACACGGTGC  ACGAGCTGTC  GGCGCGCGAG  TGCGCCTGCG       420
TGTGA                                                                      425
```

( 2 ) INFORMATION FOR SEQ ID NO:29:

( i ) SEQUENCE CHARACTERISTICS:
        ( A ) LENGTH: 169 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
ATGAGGCGCT  GGAAGGCAGC  GGCCCTGGTG  TCGCTCATCT  GCAGCTCCCT  GCTATCTGTC        60
TGGATGTGCC  AGGAGGGTCT  GCTCTTGGGC  CACCGCCTGG  GACCCGCGCT  TGCCCCGCTA       120
CGACGCCCTC  CACGCACCCT  GGACGCCCGC  ATCGCCCGCC  TGGCCCAGT                    169
```

( 2 ) INFORMATION FOR SEQ ID NO:30:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
ATCGCGCTCT  GCTCCAGGGC  GCCCCGACG   CGGTGGAGCT  TCGAGAACTT  TCTCCCTGGG        60
CTGCCCGCAT  CCCGGGACCG  CGCCGTCGAG  CGGGTCCCCG  GCGTCGGCGG  GCGCGGCCGG       120
GGGCTCGGCC  TTGTGGGCTG  CGCGAGCTCG  AGGTGCGCGT  GAGCGAGCTG  GCCTGGGCT        180
ACACGTCGGA  TGAGACCGTG  CTGTTCCGCT  ACTGCGCAGG  CGCGTGCGAG  GCGGCCATCC       240
GCATCTACGA  CCTGGGCCTT  CGGCGCCTGC  GCCAGCGGAG  GCGCGTGCGC  AGAGAGCGGG       300
CGCGGGCGCA  CCCGTGTTGT  CGCCCGACGG  CCTATGAGGA  CGAGGTGTCC  TTCCTGGACG       360
TGCACAGCCG  CTACCACACG  CTGCAAGAGC  TGTCGGCGCG  GGAGTGCGCG  TGCGTGTGA        419
```

( 2 ) INFORMATION FOR SEQ ID NO:31:

( i ) SEQUENCE CHARACTERISTICS:
        ( A ) LENGTH: 94 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Cys  Gly  Leu  Arg  Glu  Leu  Glu  Val  Arg  Val  Ser  Glu  Leu  Gly  Leu  Gly
 1                  5                         10                        15

Tyr  Ala  Ser  Asp  Glu  Thr  Val  Leu  Phe  Arg  Tyr  Cys  Ala  Gly  Ala  Cys
```

```
                        20                     25                       30
     Glu  Ala  Ala  Ala  Arg  Val  Tyr  Asp  Leu  Gly  Leu  Arg  Arg  Leu  Arg  Gln
                    35                     40                     45

Arg  Arg  Arg  Leu  Arg  Arg  Glu  Arg  Val  Arg  Ala  Gln  Pro  Cys  Cys  Arg
          50                     55                     60

Pro  Thr  Ala  Tyr  Glu  Asp  Glu  Val  Ser  Phe  Leu  Asp  Ala  His  Ser  Arg
     65                     70                     75                          80

Tyr  His  Thr  Val  His  Glu  Leu  Ser  Ala  Arg  Glu  Cys  Ala  Cys
                         85                     90
```

( 2 ) INFORMATION FOR SEQ ID NO:32:

( i ) SEQUENCE CHARACTERISTICS:
        ( A ) LENGTH: 94 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
     Cys  Gly  Leu  Arg  Glu  Leu  Glu  Val  Arg  Val  Ser  Glu  Leu  Gly  Leu  Gly
     1                   5                     10                     15

Tyr  Thr  Ser  Asp  Glu  Thr  Val  Leu  Phe  Arg  Tyr  Cys  Ala  Gly  Ala  Cys
                    20                     25                     30

Glu  Ala  Ala  Ile  Arg  Ile  Tyr  Asp  Leu  Gly  Leu  Arg  Arg  Leu  Arg  Gln
                    35                     40                     45

Arg  Arg  Arg  Val  Arg  Arg  Glu  Arg  Ala  Arg  Ala  His  Pro  Cys  Cys  Arg
          50                     55                     60

Pro  Thr  Ala  Tyr  Glu  Asp  Glu  Val  Ser  Phe  Leu  Asp  Val  His  Ser  Arg
     65                     70                     75                          80

Tyr  His  Thr  Leu  Gln  Glu  Leu  Ser  Ala  Arg  Glu  Cys  Ala  Cys
                         85                     90
```

( 2 ) INFORMATION FOR SEQ ID NO:33:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note= "SERINE OR THREONINE"

( i x ) FEATURE:
        ( A ) NAME/KEY: Modified-site
        ( B ) LOCATION: 3
        ( D ) OTHER INFORMATION: /note= "GLUTAMIC ACID OR ASPARTIC ACID"

( x i ) SEQUENCE DESCRIPTION: SEQ ID NO:33:

```
     Val  Xaa  Xaa  Leu  Gly  Leu  Gly  Tyr
     1                   5
```

( 2 ) INFORMATION FOR SEQ ID NO:34:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /note= "THREONINE OR GLUTAMIC ACID"

( i x ) FEATURE:
    ( A ) NAME/KEY: Modified-site
    ( B ) LOCATION: 3
    ( D ) OTHER INFORMATION: /note= "VALINE OR LEUCINE"

( i x ) FEATURE:
    ( A ) NAME/KEY: Modified-site
    ( B ) LOCATION: 4
    ( D ) OTHER INFORMATION: /note= "LEUCINE OR ISOLEUCINE"

( i x ) FEATURE:
    ( A ) NAME/KEY: Modified-site
    ( B ) LOCATION: 9
    ( D ) OTHER INFORMATION: /note= "ALANINE OR SERINE"

( i x ) FEATURE:
    ( A ) NAME/KEY: Modified-site
    ( B ) LOCATION: 11
    ( D ) OTHER INFORMATION: /note= "ALANINE OR SERINE"

( i x ) FEATURE:
    ( A ) NAME/KEY: Modified-site
    ( B ) LOCATION: 13
    ( D ) OTHER INFORMATION: /note= "GLUTAMIC ACID OR ASPARTIC
        ACID"

( i x ) FEATURE:
    ( A ) NAME/KEY: Modified-site
    ( B ) LOCATION: 14
    ( D ) OTHER INFORMATION: /note= "ALANINE OR SERINE"

( x i ) SEQUENCE DESCRIPTION: SEQ ID NO:34:

Glu Xaa Xaa Xaa Phe Arg Tyr Cys Xaa Gly Xaa Cys Xaa Xaa Ala
1               5                   10                  15

( 2 ) INFORMATION FOR SEQ ID NO:35:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /note= "THREONINE OR VALINE OR
            ISOLEUCINE"

( i x ) FEATURE:
        ( A ) NAME/KEY: Modified-site
        ( B ) LOCATION: 7
        ( D ) OTHER INFORMATION: /note= "TYROSINE OR PHENYLALANINE"

( i x ) FEATURE:
        ( A ) NAME/KEY: Modified-site
        ( B ) LOCATION: 8
        ( D ) OTHER INFORMATION: /note= "GLUTAMIC ACID OR ASPARTIC
            ACID"

( i x ) FEATURE:
        ( A ) NAME/KEY: Modified-site
        ( B ) LOCATION: 10
        ( D ) OTHER INFORMATION: /note= "GLUTAMIC ACID OR ASPARTIC
            ACID"

( i x ) FEATURE:
        ( A ) NAME/KEY: Modified-site
        ( B ) LOCATION: 11
        ( D ) OTHER INFORMATION: /note= "VALINE OR LEUCINE"

( x i ) SEQUENCE DESCRIPTION: SEQ ID NO:35:

```
Cys Cys Arg Pro Xaa Ala Xaa Xaa Asp Xaa Xaa Ser Phe Leu Asp
1               5                   10                  15
```

( 2 ) INFORMATION FOR SEQ ID NO:36:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /note= "ALANINE OR SERINE"

( i x ) FEATURE:
        ( A ) NAME/KEY: Modified-site
        ( B ) LOCATION: 7
        ( D ) OTHER INFORMATION: /note= "ALANINE OR SERINE"

( i x ) FEATURE:
        ( A ) NAME/KEY: Modified-site
        ( B ) LOCATION: 9
        ( D ) OTHER INFORMATION: /note= "GLUTAMIC ACID OR ASPARTIC
            ACID"

( i x ) FEATURE:
        ( A ) NAME/KEY: Modified-site
        ( B ) LOCATION: 10
        ( D ) OTHER INFORMATION: /note= "SERINE OR ALANINE"

( x i ) SEQUENCE DESCRIPTION: SEQ ID NO:36:

```
Phe Arg Tyr Cys Xaa Gly Xaa Cys Xaa Xaa Ala
1               5                   10
```

( 2 ) INFORMATION FOR SEQ ID NO:37:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /note= "ALANINE OR SERINE"

( i x ) FEATURE:
        ( A ) NAME/KEY: Modified-site
        ( B ) LOCATION: 7
        ( D ) OTHER INFORMATION: /note= "ALANINE OR SERINE"

( i x ) FEATURE:
        ( A ) NAME/KEY: Modified-site
        ( B ) LOCATION: 9
        ( D ) OTHER INFORMATION: /note= "GLUTAMIC ACID OR ASPARTIC
            ACID"

( i x ) FEATURE:
        ( A ) NAME/KEY: Modified-site
        ( B ) LOCATION: 10
        ( D ) OTHER INFORMATION: /note= "SERINE OR ALANINE"

( x i ) SEQUENCE DESCRIPTION: SEQ ID NO:37:

```
Phe Arg Tyr Cys Xaa Gly Xaa Cys Xaa Xaa Ala
1               5                   10
```

( 2 ) INFORMATION FOR SEQ ID NO:38:

( i ) SEQUENCE CHARACTERISTICS:

(A) LENGTH: 10 amino acids
(B) TYPE: amino acid
(D) TOPOLOGY: linear (ii) MOLECULE TYPE: peptide (ix) FEATURE:
(A) NAME/KEY: Modified-site
(B) LOCATION: 5
(D) OTHER INFORMATION: /note= "ISOLEUCINE OR THREONINE OR VALINE"

(ix) FEATURE:
(A) NAME/KEY: Modified-site
(B) LOCATION: 7
(D) OTHER INFORMATION: /note= "TYROSINE OR PHENYLALANINE"

(ix) FEATURE:
(A) NAME/KEY: Modified-site
(B) LOCATION: 8
(D) OTHER INFORMATION: /note= "GLUTAMIC ACID OR ASPARTIC ACID"

(ix) FEATURE:
(A) NAME/KEY: Modified-site
(B) LOCATION: 10
(D) OTHER INFORMATION: /note= "GLUTAMIC ACID OR ASPARTIC ACID"

(xi) SEQUENCE DESCRIPTION: SEQ ID NO:38:

Cys Cys Arg Pro Xaa Ala Xaa Xaa Asp Xaa
1               5                   10

(2) INFORMATION FOR SEQ ID NO:39:

(i) SEQUENCE CHARACTERISTICS:
(A) LENGTH: 10 amino acids
(B) TYPE: amino acid
(D) TOPOLOGY: linear (ii) MOLECULE TYPE: peptide (ix) FEATURE:
(A) NAME/KEY: Modified-site
(B) LOCATION: 2
(D) OTHER INFORMATION: /note= "TYROSINE OR PHENYLALANINE"

(ix) FEATURE:
(A) NAME/KEY: Modified-site
(B) LOCATION: 3
(D) OTHER INFORMATION: /note= "GLUTAMIC ACID OR ASPARTIC ACID"

(ix) FEATURE:
(A) NAME/KEY: Modified-site
(B) LOCATION: 5
(D) OTHER INFORMATION: /note= "GLUTAMIC ACID OR ASPARTIC ACID"

(ix) FEATURE:
(A) NAME/KEY: Modified-site
(B) LOCATION: 6
(D) OTHER INFORMATION: /note= "VALINE OR LEUCINE"

(xi) SEQUENCE DESCRIPTION: SEQ ID NO:39:

Ala Xaa Xaa Asp Xaa Xaa Ser Phe Leu Asp
1               5                   10

(2) INFORMATION FOR SEQ ID NO:40:

(i) SEQUENCE CHARACTERISTICS:
(A) LENGTH: 8 amino acids
(B) TYPE: amino acid
(D) TOPOLOGY: linear (ii) MOLECULE TYPE: peptide ( i x ) FEATURE:
    ( A ) NAME/KEY: Modified-site
    ( B ) LOCATION: 2
    ( D ) OTHER INFORMATION: /note= "GLUTAMIC ACID OR THREONINE"

( i x ) FEATURE:
    ( A ) NAME/KEY: Modified-site
    ( B ) LOCATION: 3
    ( D ) OTHER INFORMATION: /note= "LEUCINE OR VALINE"

( i x ) FEATURE:
    ( A ) NAME/KEY: Modified-site
    ( B ) LOCATION: 4
    ( D ) OTHER INFORMATION: /note= "ISOLEUCINE OR LEUCINE"

( x i ) SEQUENCE DESCRIPTION: SEQ ID NO:40:

```
Glu  Xaa  Xaa  Xaa  Phe  Arg  Tyr  Cys
1                    5
```

( 2 ) INFORMATION FOR SEQ ID NO:41:

( i ) SEQUENCE CHARACTERISTICS:
    ( A ) LENGTH: 13 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /note= "GLUTAMIC ACID OR THREONINE"

( i x ) FEATURE:
    ( A ) NAME/KEY: Modified-site
    ( B ) LOCATION: 3
    ( D ) OTHER INFORMATION: /note= "LEUCINE OR VALINE"

( i x ) FEATURE:
    ( A ) NAME/KEY: Modified-site
    ( B ) LOCATION: 4
    ( D ) OTHER INFORMATION: /note= "ISOLEUCINE OR LEUCINE"

( i x ) FEATURE:
    ( A ) NAME/KEY: Modified-site
    ( B ) LOCATION: 9
    ( D ) OTHER INFORMATION: /note= "SERINE OR ALANINE"

( i x ) FEATURE:
    ( A ) NAME/KEY: Modified-site
    ( B ) LOCATION: 11
    ( D ) OTHER INFORMATION: /note= "SERINE OR ALANINE"

( i x ) FEATURE:
    ( A ) NAME/KEY: Modified-site
    ( B ) LOCATION: 13
    ( D ) OTHER INFORMATION: /note= "GLUTAMIC ACID OR ASPARTIC
        ACID"

( x i ) SEQUENCE DESCRIPTION: SEQ ID NO:41:

```
Glu  Xaa  Xaa  Xaa  Phe  Arg  Tyr  Cys  Xaa  Gly  Xaa  Cys  Xaa
1                    5                         10
```

( 2 ) INFORMATION FOR SEQ ID NO:42:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:42:

```
GTNWSNGANY TNGGNYTNGG NTA                                                    23
```

( 2 ) INFORMATION FOR SEQ ID NO:43:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

```
TTYMGNTAYT GYDSNGGNDS NTGYGANKCN GC                                          32
```

( 2 ) INFORMATION FOR SEQ ID NO:44:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

```
GCNGMNTCRC ANSHNCCNSH RCARTANCKR AA                                          32
```

( 2 ) INFORMATION FOR SEQ ID NO:45:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

```
TCRTCNTCRW ANGCNRYNGG NCKRCARCA                                              29
```

( 2 ) INFORMATION FOR SEQ ID NO:46:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

```
TCNARRAANS WNAVNTCRTC NTCRWANGC                                              29
```

( 2 ) INFORMATION FOR SEQ ID NO:47:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

```
GARRMNBTNH TNTTYMGNTA YTG                                                    23
```

( 2 ) INFORMATION FOR SEQ ID NO:48:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:48:

GARRMNBTNH TNTTYMGNTA YTGYDSNGGN DSNTGHGA         38

( 2 ) INFORMATION FOR SEQ ID NO:49:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

Ser Gly Ala Arg Pro Xaa Gly Leu Arg Glu Leu Glu Val Ser Val Ser
    1               5                   10                  15

( 2 ) INFORMATION FOR SEQ ID NO:50:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

CCNACNGCNT AYGARGA         17

( 2 ) INFORMATION FOR SEQ ID NO:51:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:51:

Ala Arg Ala His Pro Cys Cys Arg Pro Thr Ala Tyr Glu Asp Glu Val
    1               5                   10                  15

Ser Phe Leu Asp
                20

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

ARYTCYTGNA RNGTRTGRTA         20

( 2 ) INFORMATION FOR SEQ ID NO:53:

( i ) SEQUENCE CHARACTERISTICS:
        ( A ) LENGTH: 28 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:53:

GACGAGGTGT CCTTCCTGGA CGTACACA 28

( 2 ) INFORMATION FOR SEQ ID NO:54:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:54:

TAGCGGCTGT GTACGTCCAG GAAGGACACC TCGT 34

( 2 ) INFORMATION FOR SEQ ID NO:55:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:55:

CAGCGACGAC GCGTGCGCAA AGAGCG 26

( 2 ) INFORMATION FOR SEQ ID NO:56:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:56:

TAYGARGACG AGGTGTCCTT CCTGGACGTA CACAGCCGCT AYCAYAC 47

( 2 ) INFORMATION FOR SEQ ID NO:57:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:57:

GCGGCCATCC GCATCTACGA CCTGGG 26

( 2 ) INFORMATION FOR SEQ ID NO:58:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:58:

CRTAGGCCGT CGGGCGRCAR CACGGGT                                27

( 2 ) INFORMATION FOR SEQ ID NO:59:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

GCGCCGAAGG CCCAGGTCGT AGATGCG                                27

( 2 ) INFORMATION FOR SEQ ID NO:60:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

CGCTACTGCG CAGGCGCGTG CGARGCGGC                              29

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

CGCCGACAGC TCTTGCAGCG TRTGGTA                                27

( 2 ) INFORMATION FOR SEQ ID NO:62:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

GAGCTGGGCC TGGGCTACGC GTCCGACGAG                             30

( 2 ) INFORMATION FOR SEQ ID NO:63:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

GCGACGCGTA CCATGAGGCG CTGGAAGGCA GCGGCCCTG                   39

( 2 ) INFORMATION FOR SEQ ID NO:64:

( i ) SEQUENCE CHARACTERISTICS:
　　　　( A ) LENGTH: 30 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:64:

GACGGATCCG CATCACACGC ACGCGCACTC                                30

( 2 ) INFORMATION FOR SEQ ID NO:65:

( i ) SEQUENCE CHARACTERISTICS:
　　　　( A ) LENGTH: 29 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:65:

GACCATATGC CGGGGGCTCG GCCTTGTGG                                 29

( 2 ) INFORMATION FOR SEQ ID NO:66:

( i ) SEQUENCE CHARACTERISTICS:
　　　　( A ) LENGTH: 30 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:66:

GACGGATCCG CATCACACGC ACGCGCACTC.                               30

( 2 ) INFORMATION FOR SEQ ID NO:67:

( i ) SEQUENCE CHARACTERISTICS:
　　　　( A ) LENGTH: 26 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:67:

CAGCGACGAC GCGTGCGCAA AGAGCG                                    26

( 2 ) INFORMATION FOR SEQ ID NO:68:

( i ) SEQUENCE CHARACTERISTICS:
　　　　( A ) LENGTH: 34 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:68:

TAGCGGCTGT GTACGTCCAG GAAGGACACC TCGT                           34

( 2 ) INFORMATION FOR SEQ ID NO:69:

( i ) SEQUENCE CHARACTERISTICS:
　　　　( A ) LENGTH: 21 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:69:

AAAAATCGGG GGTGYGTCTT A    21

(2) INFORMATION FOR SEQ ID NO:70:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:70:

CATGCCTGGC CTACYTTGTC A    21

(2) INFORMATION FOR SEQ ID NO:71:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:71:

CTGGCGTCCC AMCAAGGGTC TTCG    24

(2) INFORMATION FOR SEQ ID NO:72:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:72:

GCCAGTGGTG CCGTCGAGGC GGG    23

(2) INFORMATION FOR SEQ ID NO:73:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:73:

GGCCCAGGAT GAGGCGCTGG AAGG    24

(2) INFORMATION FOR SEQ ID NO:74:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:74:

CCACTCCACT GCCTGAWATT CWACCCC 27

( 2 ) INFORMATION FOR SEQ ID NO:75:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:75:

CCATGTGATT ATCGACCATT CGGC 24

( 2 ) INFORMATION FOR SEQ ID NO:76:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

```
Ser Pro Asp Lys Gln Met Ala Val Leu Pro Arg Arg Glu Arg Asn Arg
 1               5                   10                  15
Gln Ala Ala Ala Ala Asn Pro Glu Asn Ser Arg Gly Lys Gly Arg Arg
                20                  25                  30
Gly Gln Arg Gly Lys Asn Arg Gly Cys Val Leu Thr Ala Ile His Leu
            35                  40                  45
Asn Val Thr Asp Leu Gly Leu Gly Tyr Glu Thr Lys Glu Glu Leu Ile
        50                  55                  60
Phe Arg Tyr Cys Ser Gly Ser Cys Asp Ala Ala Glu Thr Thr Tyr Asp
 65                  70                  75                  80
Lys Ile Leu Lys Asn Leu Ser Arg Asn Arg Arg Leu Val Ser Asp Lys
                85                  90                  95
Val Gly Gln Ala Cys Cys Arg Pro Ile Ala Phe Asp Asp Asp Leu Ser
                100                 105                 110
Phe Leu Asp Asp Asn Leu Val Tyr His Ile Leu Arg Lys His Ser Ala
            115                 120                 125
Lys Arg Cys Gly Cys Ile
        130
```

( 2 ) INFORMATION FOR SEQ ID NO:77:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

```
Ser Pro Asp Lys Gln Ala Ala Ala Leu Pro Arg Arg Glu Arg Asn Arg
 1               5                   10                  15
Gln Ala Ala Ala Ala Ser Pro Glu Asn Ser Arg Gly Lys Gly Arg Arg
                20                  25                  30
Gly Gln Arg Gly Lys Asn Arg Gly Cys Val Leu Thr Ala Ile His Leu
            35                  40                  45
```

```
                                       -continued
Asn Val Thr Asp Leu Gly Leu Gly Tyr Glu Thr Lys Glu Glu Leu Ile
    50              55              60

Phe Arg Tyr Cys Ser Gly Ser Cys Glu Ser Ala Glu Thr Met Tyr Asp
65              70              75                          80

Lys Ile Leu Lys Asn Leu Ser Arg Ser Arg Arg Leu Thr Ser Asp Lys
            85              90                          95

Val Gly Gln Ala Cys Cys Arg Pro Val Ala Phe Asp Asp Asp Leu Ser
        100             105             110

Phe Leu Asp Asp Asn Leu Val Tyr His Ile Leu Arg Lys His Ser Ala
        115             120             125

Lys Arg Cys Gly Cys Ile
        130
```

( 2 ) INFORMATION FOR SEQ ID NO:78:

( i ) SEQUENCE CHARACTERISTICS:
      ( A ) LENGTH: 134 amino acids
      ( B ) TYPE: amino acid
      ( D ) TOPOLOGY: linear ( i i ) MOLECULE TYPE: protein ( x i ) SEQUENCE DESCRIPTION: SEQ ID NO:78:

```
Ser Pro Asp Lys Gln Ala Ala Ala Leu Pro Arg Arg Glu Arg Asn Arg
1               5               10              15

Gln Ala Ala Ala Ala Ser Pro Glu Asn Ser Arg Gly Lys Gly Arg Arg
            20              25              30

Gly Gln Arg Gly Lys Asn Arg Gly Cys Val Leu Thr Ala Ile His Leu
        35              40              45

Asn Val Thr Asp Leu Gly Leu Gly Tyr Glu Thr Lys Glu Glu Leu Ile
    50              55              60

Phe Arg Tyr Cys Ser Gly Ser Cys Glu Ala Ala Glu Thr Met Tyr Asp
65              70              75                          80

Lys Ile Leu Lys Asn Leu Ser Arg Ser Arg Arg Leu Thr Ser Asp Lys
            85              90                          95

Val Gly Gln Ala Cys Cys Arg Pro Val Ala Phe Asp Asp Asp Leu Ser
        100             105             110

Phe Leu Asp Asp Ser Leu Val Tyr His Ile Leu Arg Lys His Ser Ala
        115             120             125

Lys Arg Cys Gly Cys Ile
        130
```